United States Patent
Boojamra et al.

(12)

(10) Patent No.: US 6,482,921 B1
(45) Date of Patent: Nov. 19, 2002

(54) URIDYL PEPTIDE ANTIBIOTIC (UPA) DERIVATIVES, THEIR SYNTHESIS AND USE

(75) Inventors: Constantine G. Boojamra; Rémy C. Lemoine, both of San Francisco; Scott Hecker, Los Gatos; Ving J. Lee, Los Altos; Roger Léger, San Francisco, all of CA (US)

(73) Assignee: Essential Therapeutics, Inc., Mountain View, CA (US)

( * ) Notice: Subject to any disclaimer, the term of this patent is extended or adjusted under 35 U.S.C. 154(b) by 0 days.

(21) Appl. No.: 09/330,503

(22) Filed: Jun. 11, 1999

Related U.S. Application Data
(60) Provisional application No. 60/117,911, filed on Jan. 28, 1999.

(51) Int. Cl.[7] .................................................. C07K 5/08

(52) U.S. Cl. ............................ 530/331; 514/17; 514/18; 514/19; 530/330; 536/23

(58) Field of Search .............................. 514/17, 18, 19; 530/331, 330; 536/23

(56) References Cited

FOREIGN PATENT DOCUMENTS

EP          0317292    *   5/1989

* cited by examiner

*Primary Examiner*—Christopher S. F. Low
*Assistant Examiner*—David Lukton
(74) *Attorney, Agent, or Firm*—Bingham McCutchen LLP; Bernard F. Rose

(57) ABSTRACT

The present invention relates to dihydro derivatives of the uridyl peptide antibiotics mureidomycin, pacidimycin and napsamycin which have antibiotic activity against a number of bacterial strains including strains resistant to current therapeutic antibiotics.

31 Claims, No Drawings

URIDYL PEPTIDE ANTIBIOTIC (UPA) DERIVATIVES, THEIR SYNTHESIS AND USE

RELATED APPLICATIONS

This application is related to and claims priority from U.S. Provisional Patent Application serial No. 60/117,911 filed Jan. 28, 1999 which is incorporated by reference as if fully set forth herein.

INTRODUCTION

The present invention relates to organic chemistry, medicinal chemistry, biochemistry, pharmacology and medicine. In particular, it relates to uridyl peptide antibiotic (UPA) derivatives, their synthesis and their use in the treatment of bacterial infection.

BACKGROUND OF THE INVENTION

The following is offered as background information only and In is not admitted to be, or to describe, prior art to the present invention.

Despite the emergence of new and potent antibiotics, e.g., beta-lactams, macrolides, quinolones, tetracyclines and aminoglycosides, the incidence of bacterial resistance to antibiotics continues to increase at an alarming rate. Furthermore, cross-resistance, the ability of a bacterium resistant to one antibiotic to resist other different antibiotic(s) is also on the rise. To combat these phenomena, there is a need not merely for new antibiotic compounds but for new classes of antibiotics which are sufficiently different in structure and mode of action from current antibiotics to decrease the rate at which resistance arises and to reduce the chances of cross-resistance.

The uridyl peptide antibiotics (UPAs) appear to be such a class of antibiotic compounds. In the first place, their chemical structures, shown below, are unique among current therapeutic antibiotics:

TABLE 1

Some Pacidamycins, Mureidomycins and Napsamycins

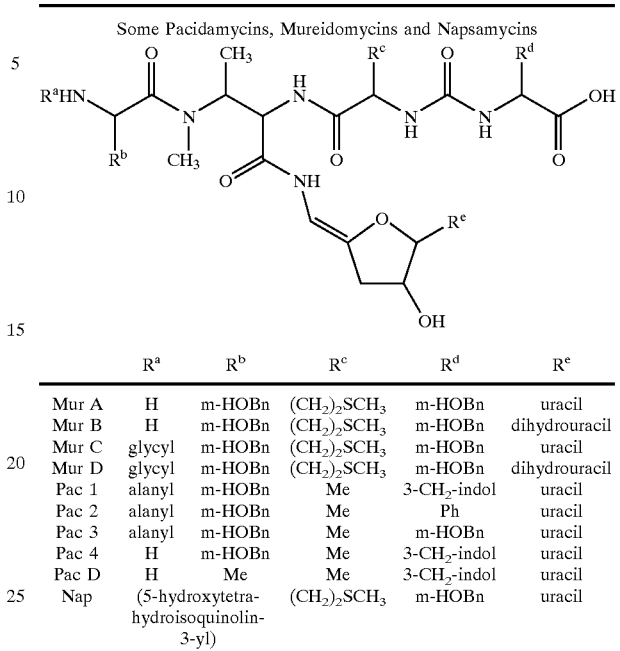

| | $R^a$ | $R^b$ | $R^c$ | $R^d$ | $R^e$ |
|---|---|---|---|---|---|
| Mur A | H | m-HOBn | $(CH_2)_2SCH_3$ | m-HOBn | uracil |
| Mur B | H | m-HOBn | $(CH_2)_2SCH_3$ | m-HOBn | dihydrouracil |
| Mur C | glycyl | m-HOBn | $(CH_2)_2SCH_3$ | m-HOBn | uracil |
| Mur D | glycyl | m-HOBn | $(CH_2)_2SCH_3$ | m-HOBn | dihydrouracil |
| Pac 1 | alanyl | m-HOBn | Me | 3-$CH_2$-indol | uracil |
| Pac 2 | alanyl | m-HOBn | Me | Ph | uracil |
| Pac 3 | alanyl | m-HOBn | Me | m-HOBn | uracil |
| Pac 4 | H | m-HOBn | Me | 3-$CH_2$-indol | uracil |
| Pac D | H | Me | Me | 3-$CH_2$-indol | uracil |
| Nap | (5-hydroxytetra-hydroisoquinolin-3-yl) | | $(CH_2)_2SCH_3$ | m-HOBn | uracil |

Mureidomycin = Mur;
Pacidamycin = Pac;
Napsamycins = Nap

Furthermore, the UPAs share a bacterial cellular target which is likewise unique among current antibiotics. That target is bacterial translocase I (phospho-N-acetylmuramyl-pentapeptide translocase), an enzyme that catalyzes the first reaction in the membrane-bound cycle of reactions in bacterial peptidoglycan biosynthesis, e.g., in *E. coli* the transfer of phospho-MurNAc-L-Ala-γ-D-Glu-m-DAP-D-Ala-D-Ala from UMP to a membrane bound carrier, undecaprenyl phosphate. There are other translocase inhibitors, such as tunicamycin (Compound 1) and amphomycin (Compound 2),

COMPOUND 1

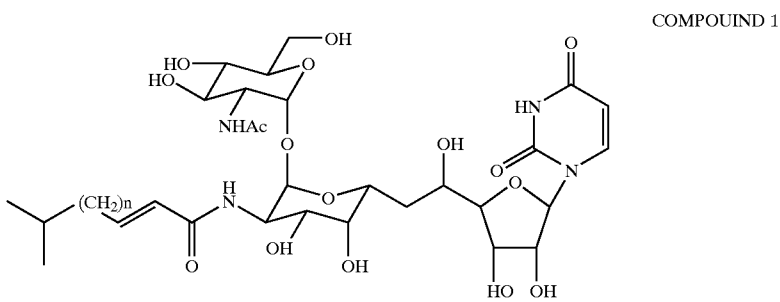

n = 8–11

COMPOUND 2

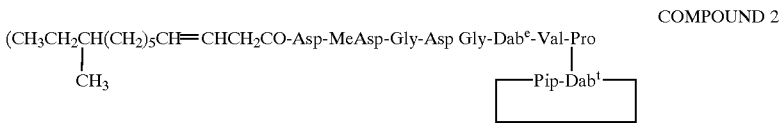

Asp=aspartic acid

Gly=glycine

Val=valine

Pro=proline

Dab$^e$=D-erythro-α,β-diaminobutyric acid

Dab$^t$=L-threo-α,β-diaminobutyric acid

Pip=D-pipecolic acid however, in addition to inhibiting bacterial translocase, these compounds also inhibit mammalian enzymes that catalyze the formation of lipid-linked saccharides through which membrane and secreted proteins are glycosylated which precludes their use as therapeutic antibiotics. On the other hand, the mureidomycins (and, it would be expected, the structurally similar pacidamycins napsamycins), while inhibiting bacterial translocase I similarly to tunicamycin and amphomycin, do not inhibit either bacterial or mammalian lipid-linked saccharide formation (Inukai, M., *Antimicrobial Agents and Chemotherapy*, 1992, 980–83). The UPAS, then, would appear to be excellent targets for the development of novel therapeutic antibiotics.

SUMMARY OF THE INVENTION

Our own efforts to develop novel therapeutic antibiotics to treat and prevent bacterial infections has resulted in the synthesis of dihydro derivatives of uridyl peptide antibiotics which are active against a variety of bacteria including, significantly, several species which are displaying resistance to current antibiotic therapies.

Thus, in one aspect the present invention relates generally to dihydro derivatives, and their physiologically acceptable salts and prodrugs, of uridyl peptide antibiotics. In addition, the present invention relates to the preparation of pharmaceutical compositions of the dihydro derivatives, and their physiologically acceptable salts and prodrugs, and the use of the compositions for the prevention and treatment of bacterial infections.

As used herein, "uridyl peptide antibiotic" refers to a compound having the core structure:

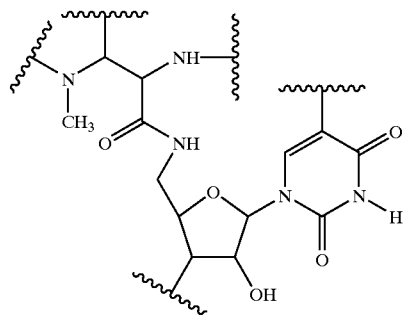

As used herein, "dihydro uridyl peptide antibiotic" refers to a compound having the core structure:

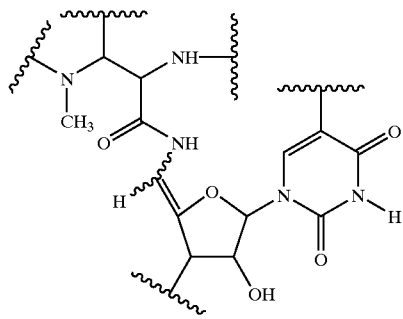

As used herein, "tetrahydro uridyl peptide antibiotic" refers to a compound having the core structure:

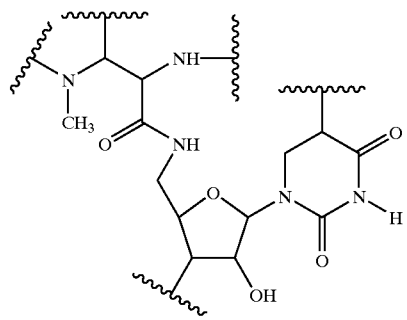

As used herein, "pharmaceutical composition" refers to a mixture of one or more of the compounds described herein, or physiologically acceptable salts or prodrugs thereof, with other chemical components, such as physiologically acceptable carriers and/or excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

An "excipient," as used herein, refers to an inert substance added to a pharmaceutical composition to further facilitate administration of a compound. Examples, without limitation, of excipients include calcium carbonate, calcium phosphate, various sugars and starches, cellulose derivatives, gelatin, vegetable oils and polyethylene glycols.

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water solubility is beneficial.

1. Chemistry

A. General structural features.

Thus, in one aspect, this invention relates to a compound having the chemical structure:

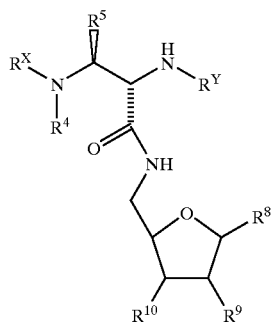

R[x] is selected from the group consisting of a first amino acid and a first polypeptide, the first amino acid or the first polypeptide being optionally substituted with one or more groups independently selected from the group consisting of alkyl, cycloalkyl, alkenyl, alkynyl, aryl, heteroaryl and heteroalicyclic.

R[y] is selected from the group consisting of a second amino acid and a second polypeptide, the second amino group or the second polypeptide being optionally substituted with one or more groups independently selected from the group consisting of alkyl, cycloalkyl, alkenyl, alkynyl, aryl, heteroaryl and heteroalicyclic.

The second amino acid or a terminal amino acid of the second polypeptide is linked through its α-amino nitrogen atom to an α-amino nitrogen atom of a third amino acid or a third polypeptide by a carbonyl group, the third amino acid or the third polypeptide being optionally substituted with one or more groups independently selected from the group consisting of alkyl, cycloalkyl, alkenyl, alkynyl, aryl, heteroaryl and heteroalicyclic.

R[4] and R[5] are independently selected from the group consisting of hydrogen, alkyl, cycloalkyl, alkenyl, alkynyl, aryl, heteroaryl and heteroalicyclic.

R[8] is uracil or dihydrouracil optionally substituted with a group selected from alkyl, cycloalkyl, alkenyl, alkynyl, aryl, heteroaryl, heteralicyclic, halo, cyano, nitro and —NRR'.

R[9] and R[10] are independently selected from the group consisting of hydrogen, hydroxy, alkoxy, mercapto, alkylthio, halo, cyano, and —NRR'.

R and R' are independently selected from the group consisting of hydrogen, alkyl, alkenyl, alkynyl, aryl, heteroaryl, heteroalicyclic, carbonyl, C-carboxy and O-carboxy.

As used herein, the term "alkyl" refers to a saturated aliphatic hydrocarbon including straight chain and branched chain groups. Preferably, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, and —NRR', R and R' being as defined above.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, adamantane, X cyclohexadiene, cycloheptane and, cycloheptatriene. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, mercapto, alkylthio, arylthio, cyano, halo, carbonyl, thiocarbonyl, carboxy, O-carbamyl, N-carbamyl, C-amido, N-amido, S-sulfonamido, N-sulfonamido, nitro and —NRR', with R and R' being as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl (a monocyclic aryl), naphthalenyl (a bicyclic aryl) and anthracenyl (a tricyclic aryl). The aryl group may be substituted or unsubstituted. When substituted, the substituted group(s) is preferably one or more selected from halo, trihalomethyl, alkyl, hydroxy, alkoxy, aryloxy, mercapto, alkylthio, arylthio, cyano, nitro, carbonyl, thiocarbonyl, C-carboxy, Q-carboxy, O-carbamyl, N-carbamyl, O-thiocarbamyl, N-thiocarbamyl, C-amido, N-amido, sulfinyl, sulfonyl, S-sulfonamido, N-sulfonamido, trihalomethanesulfonamido and —NRR', R and R' being as defined above.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituted group(s) is preferably one or more selected from alkyl, cycloalkyl, halo, trihalomethyl, hydroxy, alkoxy, aryl, aryloxy, mercapto, alkylthio, arylthio, cyano, nitro, carbonyl, thiocarbonyl, sulfonamido, carboxy, sulfinyl, sulfonyl, O-carbamyl, N-carbamyl, O-thiocarbamyl, N-thiocarbamyl, C-amido, N-amido, S-sulfonamido, N-sulfonamido and —NRR', R and R' being as defined above.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more selected from alkyl, cycloalkyl, aryl, halo, trihalomethyl, hydroxy, alkoxy, aryloxy, mercapto, alkylthio, arylthio, cyano, nitro, carbonyl, thiocarbonyl, carboxy, O-carbamyl, N-carbamyl, O-thiocarbamyl, N-thiocarbamyl, sulfinyl, sulfonyl, C-amido, N-amido, S-sulfonamido, N-sulfonamido and —NRR', R and R' being as defined above.

A "heteroaryl/aryl bicyclic" group refers to a group of general structure 1 wherein the "A" ring is aryl and the B ring is heteroaryl. The "A" and "B" rings are independently five or six member rings. The heteroaryl/aryl bicyclic is covalently bonded in a compound of this invention through the B ring.

Structure 1

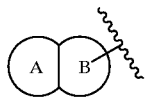

A "heteroalicylic/aryl bicyclic" group refers to a group of general structure 1 wherein the "A" ring is aryl and the "B" ring is heteroalicyclic. The heteroalicylic/aryl bicyclic group is covalently bonded in a compound of this invention through the "B" ring.

A "heteroaryl/heteroaryl bicyclic" group refers to a group general structure wherein the "A" ring and the "B" rings are heteroaryl. The heteroaryl/heteroaryl bicyclic group is covalently bonded in a compound of this invention through "B" ring.

A "heteroalicylic/heteroaryl bicyclic" group refers to a group of general structure 1 wherein the "A" ring is heteroaryl and the "B" ring is heteroalicyclic. The heteroalicylic/heteroaryl bicyclic group is covalently bonded in a compound of this invention through the "B" ring.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "mercapto" group refers to an —SH group.

An "alkylthio" group refers to both an S-alkyl and an —S-cycloalkyl group, as defined herein.

An "arylthio" group refers to both an —S-aryl and an —S-heteroaryl group, as defined herein.

A "carbonyl" group refers to a —C(=O)—R" group, where R" is selected from the group consisting of hydrogen, alkyl, cycloalkyl, aryl, heteroaryl (bonded through a ring carbon) and heteroalicyclic (bonded through a ring carbon), as these are defined herein.

An "aldehyde" group refers to a carbonyl group where R" is hydrogen.

A "thiocarbonyl" group refers to a —C(=S)—R" group, with R" as defined herein,

An "O-carboxy" group refers to a R"C(=O)O-group, with R" as defined herein.

A "C-carboxy" group refers to a —C(=O)OR" group with R" as defined herein.

An "acetyl" group refers to a —C(=O)CH₃ group.

A "carboxyalkyl" group refers to —(CH₂)$_r$C(=O)OR" wherein r is 1–6 and R" is as defined above.

A "carboxylic acid" group refers to a C-carboxy group in which R', is hydrogen.

A "halo" group refers to fluorine, chlorine, bromine or iodine.

A "trihalomethyl", group refers to a —CX₃ group wherein X is a halo group as defined above.

A "trihalomethanesulfonyl", group refers to a X₃CS(=O)₂-group with X as defined above.

A "cyano" group refers to a —C≡N group.

An "isocyanato" group refers to a —NCO group.

A "thiocyanato" group refers to a —CNS group.

An "isothiocyanato" group refers to a —NCS group.

A "sulfinyl" group refers to a —S(=O)—R" group, with R" as defined herein.

A "sulfonyl" group refers to a —S(=O)₂R" group, with R" as defined herein.

A "S-sulfonamido" group refers to a —S(=O)₂NRR' group, with R and R' as defined herein.

A "N-sulfonamido" group refers to a RS(=O)₂NH-group with R as defined herein.

A "trihalomethanesulfonamido" group refers to a X₃CS(=O)₂NH-group with X as defined herein.

An "O-carbamyl" group refers to a —OC(=O)NRR' group with R and R' as defined herein.

An "N-carbamyl" group refers to a ROC(=O)NH-group, with R as defined herein.

An "O-thiocarbamyl" group refers to a —OC(=S)—NRR' group with R and R' as defined herein.

An "N-thiocarbamyl", group refers to an ROC(=S)NH-group, with R as defined herein.

A "C-amido" group refers to a —C(=O)—NRR' group with R and R' as defined herein.

An "N-amido" group refers to a RC(=O)NH-group, with R as defined herein.

A "nitro" group refers to a —NO₂ group.

A "tert-butyl" group refers to a (CH₃)₃C— group.

An "isopropyl" group refers to a (CH₃)₂CH— group.

A "ureido" group refers to a —NHC(=O)NRR' with R and R' as defined herein.

A "amidino" group refers to a RR'NC(=NH)— group with R and R' as defined herein.

A "guanidino" group refers to a —NHC(=NH)NRR' with R and R' as defined herein.

An "ammonium" group refers to an —NHRR' group with R and R' as defined herein.

A "polypeptidyl" group refers to a group formed by the covalent bonding of the amino group of an α-amino acid with the carboxy group of another amino acid. A great many amino acids may be bonded to one another in this manner; i.e., a polypeptidyl group has the general formula:

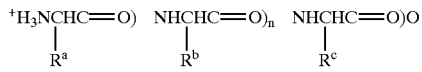

wherein $R^a$, $R^b$, and $R^c$, may be the same or different depending on the amino acid used. Of course, as the number of $R^b$'s increases with "n", each $R^b$ may be the same or different. If "n" is 0, then the polypeptide would be referred to as a "dipeptidyl", group; if "n" is 1, the molecule would be referred to as a "tripeptidyl," group; etc. As used herein, a "polypeptidyl" refers to a linear chain of amino acids wherein n is 3–18 (i.e., 5 to 20 amino acids linked head to tail); preferably a "polypeptide" of this invention is dipeptidyl, a tripeptidyl or a tetrapeptidyl group; most preferably, a polypeptidyl group of this invention is a dipeptidyl group. The amino acid on the left hand side of the above formula is referred to as the N-terminal amino acid residue and the amino acid on the right hand side is referred to as the C-terminal amino acid residue.

By "amino acid" is meant a compound selected from the group consisting of alanine, arginine, asparagine, cysteine, cystine, 3,5-dibromotyrosine, 3,5-diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine.

By "combined," when referring to two adjacent "R" groups herein is meant that the two "R" groups are covalently bonded to y each other so as to form a ring system. As used herein, the ring system may be heteroaryl, heteroalicyclic, heteroaryl/aryl bicyclic, heteroalicyclic/aryl bicyclic, heteroaryl/heteroaryl bicyclic or a heteroaryl/heteroalicyclic bicyclic.

A "uracil" group has the chemical structure:

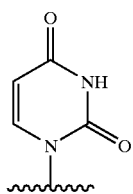

A "dihydrouracil" has the chemical structure:

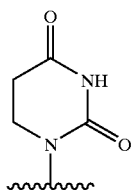

A "6-hydroxytetrahydroisoquinolin-3-yl" group has the chemical structure:

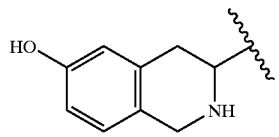

A "1-methyl-6-hydroxytetrahydroisoquinolin-3-yl", group has the chemical structure:

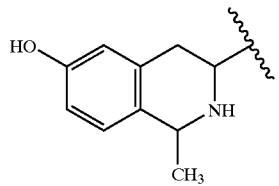

A "stereochemical configuration" refers to the three dimensional relationship of the substituents on an asymmetric carbon atom (a carbon atom with four different group attached to it). If a specific stereochemistry is not shown at a particular asymmetric carbon atom of a compound of this invention, unless expressly stated otherwise in the text the configuration at that carbon may be either R or S.

A compound of this invention that is capable of inhibiting the growth of bacteria is yet another aspect of this invention.

By "inhibiting the growth" is meant slowing, preferably stopping the proliferation of a bacterium as the result of the presence of a compound or compounds of this invention under conditions which normally would favor such growth in the absence of the compound or compounds. Preferably, such inhibition of growth or proliferation includes the destruction of individual bacteria.

A compound of this invention that is capable of selectively inhibiting the growth of bacteria is a further aspect of this invention.

By "selectively" is meant that the compound inhibits bacterial cellular processes while having no or very little effect on the cellular processes of a patient species. One way to measure the selectivity would be to compare the MIC (defined below) of a compound of this invention for cellular processes in a patient species with the MIC for inhibition of bacterial growth for the subject bacteria. A ratio of patient species MIC to bacterial MIC of from 10 to 10,000 would indicate selectivity; preferably the ratio would be from 100 to 10,000; most preferably from 1,000 to 10,000.

A compound of this invention that inhibits bacterial translocase I is yet another aspect of this invention.

That the bacteria which are inhibited by a compound of this invention are of the genus Pseudomonas, Eschericia, Staphylococcus, Streptococcus, Enterococcus, Mycobacteria or Haemophilus is a still further aspect of this invention.

B. Preferred structural features.

A preferred aspect of this invention relates to a compound having the chemical structure:

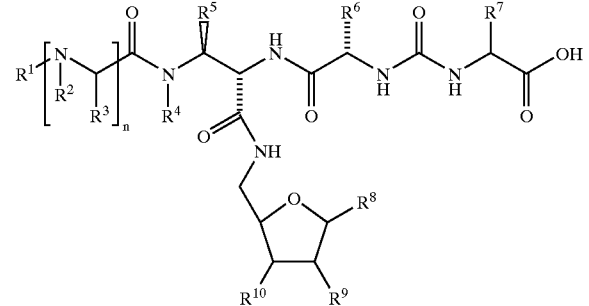

$R^1$ and $R^2$ are independently selected from the group consisting of hydrogen, alkyl, cycloalkyl, alkenyl, alkynyl, aryl, heteroaryl, heteroalicyclic, carbonyl, sulfonyl, trihalomethanesulfonyl, C-carboxy, O-carboxy, C-amido, cyano, hydroxy, alkoxy, —NRR', amino acid, polypeptidyl, combined with one another, a heteroaryl or a heteroalicyclic and, combined with $R^3$ a heteroaryl, a heteroalicyclic, a heteroaryl/aryl bicyclic, a heteroalicyclic/aryl bicyclic, a heteroaryl/heteroaryl bicyclic or a heteroalicyclic/heteroaryl bicyclic.

$R^3$ is selected from the group consisting of hydrogen, alkyl, cycloalkyl, alkenyl, alkynyl, aryl, heteroaryl, heteroalicyclic, C-carboxy, C-amido and, combined with $R^2$, a heteroaryl, a heteroalicyclic, a heteroaryl/aryl bicyclic, a heteroalicyclic/aryl bicyclic, a heteroaryl/heteroaryl bicyclic and a heteroalicyclic/heteroaryl bicyclic.

$R^4$ and $R^5$ are independently selected from the group consisting of hydrogen, alkyl, alkenyl, alkynyl, aryl and heteroaryl.

$R^6$ and $R^7$ are independently selected from the group consisting of hydrogen, alkyl, cycloalkyl, alkenyl, alkynyl, aryl, heteroaryl, heteroalicyclic, C-carboxy and C-amido.

$R^8$ is uracil or dihydrouracil optionally substituted with a group selected from the group consisting of alkyl, alkenyl, alkynyl, aryl, heteroaryl, heteroalicyclic, halo, cyano, nitro and —NRR'.

$R^9$ and $R^{10}$ are selected from the group consisting of hydrogen, halo, cyano, hydroxy, alkoxy, mercapto, alkylthio and —NRR'.

The variable "n" may be 0 or 1.

R and R' are independently selected from the group consisting of hydrogen, alkyl, cycloalkyl, alkenyl, alkynyl, aryl, carbonyl, sulfonyl, and, combined, a five-member or a six-member heteroalicyclic ring.

A further presently preferred embodiment of this invention is that n is 1 and $R^1$ and $R^2$ are independently selected from the group consisting of hydrogen, amino acid, dipeptidyl, tripeptide, tetrapeptide and, combined with $R^3$, a heteroalicyclic/aryl bicyclic or a heteroalicyclic/heteroaryl bicyclic.

It is also a presently preferred embodiment of this invention that $R^3$ is selected from the group consisting of hydrogen, lower alkyl, monocyclic aryl and bicyclic aryl.

It is presently preferred that $R^4$ and $R^5$ are independently selected from the group consisting of hydrogen and lower alkyl.

Another presently preferred embodiment of this invention is that $R^6$ and $R^7$ are independently selected from the group consisting of hydrogen, lower alkyl, monocyclic aryl and bicyclic aryl.

A further presently preferred embodiment of this invention is that $R^8$ is uracil or dihydrouracil optionally substituted with a group selected from the group consisting of lower alkyl, lower alkenyl, lower alkynyl, halo, hydroxy, alkoxy, mercapto and alkylthio.

Likewise, a presently preferred embodiment of this invention is that $R^9$ is selected from the group consisting of hydrogen, halo, hydroxy, alkoxy, mercapto and alkylthio.

Yet another presently preferred embodiment of this invention is that $R^{10}$ is selected from the group consisting of hydrogen and hydroxy.

A further preferred embodiment of this invention at present also is that n is 1 and $R^1$ and $R^2$ are independently selected from the group consisting of hydrogen, amino acid, dipeptidyl, and combined with $R^3$, a heteroalicyclic/aryl bicyclic.

Similarly, it is a further presently preferred embodiment of this invention that $R^3$ is selected from the group consisting of hydrogen;

lower alkyl optionally substituted with one or more groups selected from the group consisting of halo, cyano, nitro, hydroxy, lower alkoxy, mercapto, (lower alkyl)thio, —NRR', guanidino, amidino, ureido, C-carboxy, aryl optionally substituted with one or more group selected from the group consisting of
lower alkyl, trihalomethyl, lower alkoxy, (lower alkyl)thio, halo, hydroxy, mercapto, nitro, cyano and —NRR', heteroaryl optionally substituted with one or more groups selected from the group consisting of
lower alkyl, lower alkoxy, (lower alkyl)thio, halo, hydroxy, mecapto, nitro, cyano and —NRR', heteroaryl optionally substituted with one or more groups selected from the group consisting of lower alkyl, lower alkoxy, (lower alkyl)thio, halo, hydroxy, mercapto, nitro, cyano and —NRR'; and, combined with $R^2$ a six-member heteroalicyclic/aryl or heteroalicyclic/heteroaryl bicyclic.

A still further presently preferred embodiment of this invention is that $R^4$ and $R^5$ are independently selected from the group consisting of hydrogen and lower alkyl.

Another presently preferred embodiment of this invention is that $R^6$ and $R^7$ are independently selected from the group consisting of hydrogen;

lower alkyl optionally substituted with a one or more groups selected from the group consisting of halo, cyano, nitro, hydroxy, lower alkoxy,. mercapto, (lower alkyl)thio, amidino, guanidino, amidino, ureido, —NRR', C-carboxy, aryl optionally substituted with one or more group selected from the group consisting of
lower alkyl, trihalomethyl, lower alkoxy, (lower alkyl)thio, halo, hydroxy, mercapto, nitro, cyano and —NRR', and heteroaryl optionally substituted with one or more groups selected from the group consisting of
lower alkyl, (trihalomethyl), lower alkoxy, (lower alkyl)thio, halo, hydroxy, mercapto, nitro, cyano and —NRR', and, heteroaryl optionally substituted with one or more groups selected from the group consisting of lower alkyl, lower alkoxy, (lower alkyl)thio, halo, hydroxy, mercapto, nitro, cyano and —NRR'.

Yet another presently preferred embodiment of this invention is that $R^8$ is uracil or dihydrouracil optionally substituted with a group selected from the group consisting of hydrogen, lower alkyl, lower alkenyl and halo.

It is also a presently preferred embodiment of this invention that $R^9$ is selected from the group consisting of hydrogen, halo and hydroxy.

A further presently preferred embodiment of this invention is that $R^{10}$ is selected from the groups consisting of hydrogen and hydroxy.

A presently particularly preferred embodiment of this invention is that n is 1;

$R^1$ and $R^2$ are both hydrogen or $R^1$ is hydrogen and $R^2$ is combined with $R^3$ to give 6-hydroxyisoquinolin-3-yl or 1-methyl-6hydroxyisoquinoline-3-yl;

$R^3$ is selected from the group consisting of hydrogen;

lower alkyl, optionally substituted with a group selected from the group consisting of hydroxy, thichydroxy, lower alkyl alkoxy, lower alkyl alkylthio, halo, amino, —NRR' and aryl, optionally substituted with one or more groups selected from the group consisting of
lower alkyl, trihalomethyl, hydroxy, lower alkyl alkoxy, lower alkyl alkylthio, halo, nitro amino and —NRR'; and, combined with $R^2$, 6-hydroxyisoquinolin-3-yl or 1-methyl-6hydroxyisoquinolin-3-yl;

$R^4$ and $R^5$ are methyl;

$R^6$ is selected from the group consisting of
lower alkyl optionally substituted with a group selected from the group consisting of hydroxy, lower alkoxy, (lower alkyl)thio, halo,—NRR', cyclohexyl,
aryl, optionally substituted with one or more groups selected from the group consisting of
hydroxy, lower alkoxy, (lower alkyl)thio, halo, trihalomethyl, nitro, —NRR', and phenyl, and,
heteroaryl, optionally substituted with one or more groups selected from the group consisting of
hydroxy, lower alkoxy, (lower alkyl)thio, halo, trihalomethyl, nitro, —NRR', and phenyl;

$R^7$ is selected from the group consisting of
lower alkyl substituted with a group selected from the group consisting of
aryl optionally substituted with one or more groups selected from the group consisting of
hydroxy, lower alkoxy, (lower alkyl)thio, halo, trihalomethyl, nitro, —NRR' and phenyl,
heteroaryl optionally substituted with one or more groups selected from the group consisting of
hydroxy, lower alkoxy, (lower alkyl)thio, halo, trihalomethyl, nitro, —NRR' and phenyl, and
aryl, optionally substituted with one or more groups selected from the group consisting of hydroxy, lower alkoxy, (lower alkyl)thio, halo, trihalomethyl, nitro, —NRR' and phenyl;

$R^8$ is uracil or dihydrouracil;

$R^9$ is hydroxy;

$R^{10}$ is hydrogen; and,

R and R' are independently selected from the group consisting of hydrogen and lower alkyl.

It is another presently particularly preferred embodiment of this invention that an "aryl" group in any of the above embodiments is phenyl or naphthyl.

It is also a presently particularly preferred embodiment of this invention that a "heteroaryl" group in any of the above embodiments is selected from the group consisting of indol-3-yl, thien-2-yl, benzothien-3-yl, thiazol-4-yl, imidazol-2-yl and imidazol-4-yl.

It is also a presently preferred embodiment of this invention that n is 0 and $R^1$ is selected from the group consisting of lower alkyl substituted with one or more groups selected from the group consisting of —NRR', N-piperazinyl and an aryl group which is itself substituted with one or more groups selected from the group consisting of —NRR' and lower alkyl substituted with one or more —NRR' groups.

Table 2 shows additional presently preferred embodiment of this invention.

TABLE 2

| | $R^1$, $R^2$ | $R^3$ | $R^4$, $R^5$ | $R^6$ | $R^7$ | $R^8$ | $R^9$ | $R^{10}$ |
|---|---|---|---|---|---|---|---|---|
| 100 | H | PhCH₂— | —CH₃ | PhCH₂— | HO-C₆H₄-CH₂— | uracil | OH | H |
| 101 | H | (CH₃)₂CHCH₂— | —CH₃ | PhCH₂— | HO-C₆H₄-CH₂— | uracil | OH | H |
| 102 | H | H | —CH₃ | PhCH₂— | HO-C₆H₄-CH₂— | uracil | OH | H |
| 103 | H | 3-HO-C₆H₄-CH₂— | —CH₃ | —CH₃ | indol-3-yl-CH₂— | uracil | OH | H |
| 104 | H | H | —CH₃ | —CH₂CH₂SCH₃ | HO-C₆H₄-CH₂— | uracil | OH | H |
| 105 | H | 4-F-C₆H₄-CH₂— | —CH₃ | 4-F-C₆H₄-CH₂— | HO-C₆H₄-CH₂— | uracil | OH | H |
| 106 | H | PhCH₂— | —CH₃ | 4-F-C₆H₄-CH₂— | HO-C₆H₄-CH₂— | uracil | OH | H |
| 107 | H | (CH₃)₂CHCH₂— | —CH₃ | 4-F-C₆H₄-CH₂— | HO-C₆H₄-CH₂— | uracil | OH | H |
| 108 | H | (CH₃)₂CHCH₂— | —CH₃ | (CH₃)₂CHCH₂— | indol-3-yl-CH₂— | uracil | OH | H |
| 109 | H | H | —CH₃ | (CH₃)₂CHCH₂— | indol-3-yl-CH₂— | uracil | OH | H |

TABLE 2-continued

| | R¹, R² | R³ | R⁴, R⁵ | R⁶ | R⁷ | R⁸ | R⁹ | R¹⁰ |
|---|---|---|---|---|---|---|---|---|
| 110 | H | 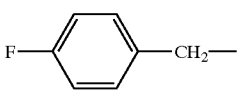 4-F-C₆H₄-CH₂— | —CH₃ | —CH₂CH₂SCH₃ | 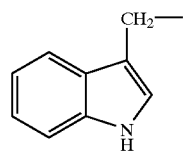 indol-3-yl-CH₂— | uracil | OH | H |
| 111 | H | 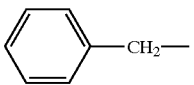 C₆H₅-CH₂— | —CH₃ | —CH₂CH₂SCH₃ | 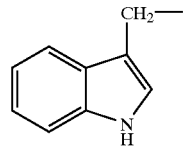 indol-3-yl-CH₂— | uracil | OH | H |
| 112 | H | H | —CH₃ | —CH₂CH₂SCH₃ | 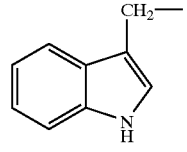 indol-3-yl-CH₂— | uracil | OH | H |
| 113 | H | 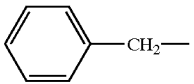 C₆H₅-CH₂— | —CH₃ | 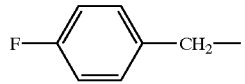 4-F-C₆H₄-CH₂— | 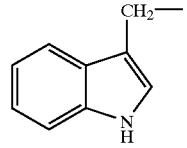 indol-3-yl-CH₂— | uracil | OH | H |
| 114 | H | 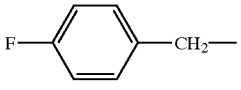 4-F-C₆H₄-CH₂— | —CH₃ | 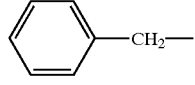 C₆H₅-CH₂— | 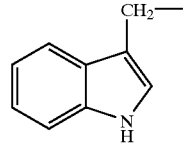 indol-3-yl-CH₂— | uracil | OH | H |
| 115 | H | —CH₃ | —CH₃ | —CH₂CH₂SCH₃ | 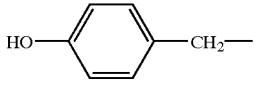 4-HO-C₆H₄-CH₂— | uracil | OH | H |
| 116 | H | H | —CH₃ | 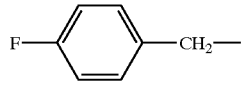 4-F-C₆H₄-CH₂— | 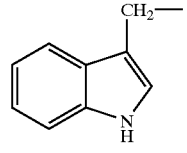 indol-3-yl-CH₂— | uracil | OH | H |
| 117 | H | (CH₃)₂CHCH₂— | —CH₃ | 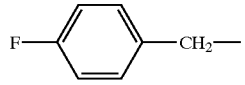 4-F-C₆H₄-CH₂— | 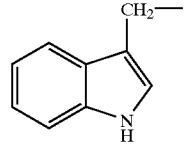 indol-3-yl-CH₂— | uracil | OH | H |
| 118 | H | 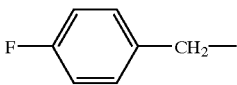 4-F-C₆H₄-CH₂— | —CH₃ | 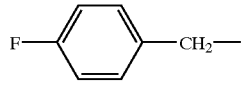 4-F-C₆H₄-CH₂— | 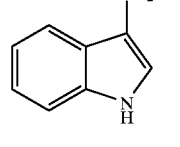 indol-3-yl-CH₂— | uracil | OH | H |
| 119 | H | —CH₃ | —CH₃ | 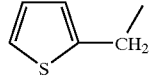 thien-2-yl-CH₂— | 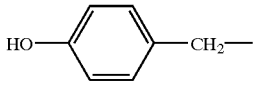 4-HO-C₆H₄-CH₂— | uracil | OH | H |

TABLE 2-continued
| | R¹, R² | R³ | R⁴, R⁵ | R⁶ | R⁷ | R⁸ | R⁹ | R¹⁰ |
|---|---|---|---|---|---|---|---|---|
| 120 | H | H | —CH₃ | (CH₃)CHCH₂— | 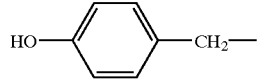 | uracil | OH | H |
| 121 | H | H | —CH₃ | —CH₃ | 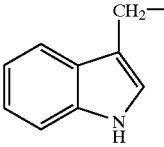 | uracil | OH | H |
| 122 | H | —CH₃ | —CH₃ | 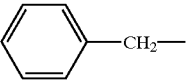 | 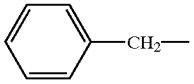 | uracil | OH | H |
| 123 | H | H₂N(CH₂)₄C(=O)— | —CH₃ | 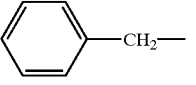 | 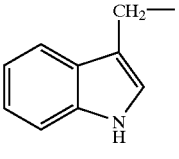 | uracil | OH | H |
| 124 | H | H₂N(CH₂)₄C(=O)— | —CH₃ | 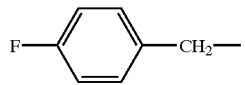 | 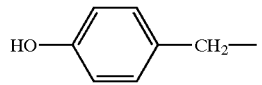 | uracil | OH | H |
| 125 | H | —CH₃ | —CH₃ | 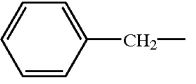 | 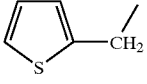 | uracil | OH | H |
| 126 | H | —CH₃ | —CH₃ | 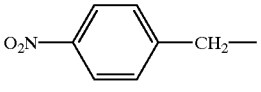 | 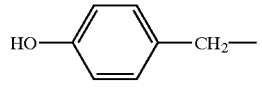 | uracil | OH | H |
| 127 | H | — | —CH₃ | 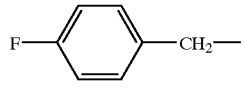 | 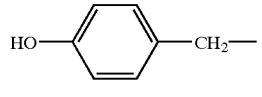 | uracil | OH | H |
| 128 | H | H | —CH₃ | 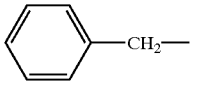 | 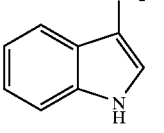 | uracil | OH | H |
| 129 | H | H | —CH₃ | 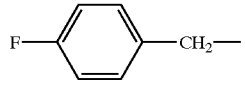 | 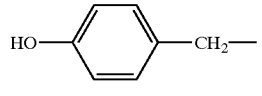 | uracil | OH | H |
| 130 | H | —CH₃ | —CH₃ | 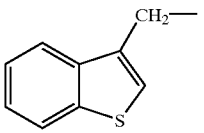 | 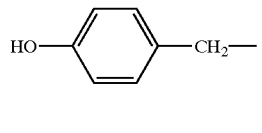 | uracil | OH | H |
| 131 | H | 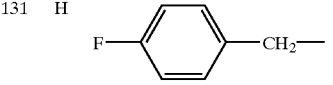 | —CH₃ | 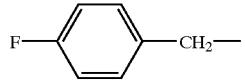 | 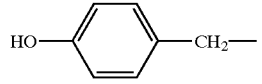 | uracil | OH | H |

TABLE 2-continued

| | R¹, R² | R³ | R⁴, R⁵ | R⁶ | R⁷ | R⁸ | R⁹ | R¹⁰ |
|---|---|---|---|---|---|---|---|---|
| 132 | H | —CH₃ | —CH₃ | 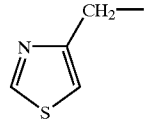 (thiazol-4-ylmethyl) | 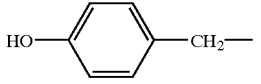 (4-hydroxybenzyl) | uracil | OH | H |
| 133 | H | —CH₃ | —CH₃ | 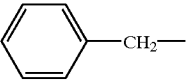 (benzyl) | 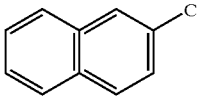 (naphthalen-2-ylmethyl) | uracil | OH | H |
| 134 | H | —CH₃ | —CH₃ | 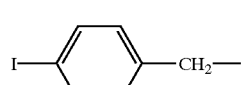 (4-iodobenzyl) | 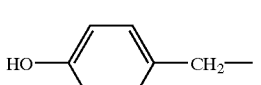 (4-hydroxybenzyl) | uracil | OH | H |
| 135 | H | —CH₃ | —CH₃ | 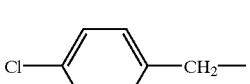 (4-chlorobenzyl) | 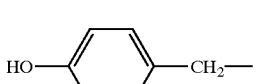 (4-hydroxybenzyl) | uracil | OH | H |
| 136 | H | —CH₃ | —CH₃ | 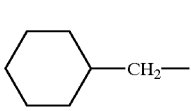 (cyclohexylmethyl) | 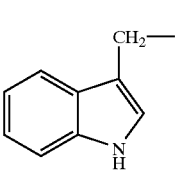 (indol-3-ylmethyl) | uracil | OH | H |
| 137 | H | —CH₃ | —CH₃ | 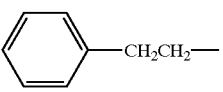 (phenethyl) | 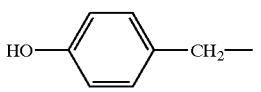 (4-hydroxybenzyl) | uracil | OH | H |
| 138 | H | —CH₃ | —CH₃ | 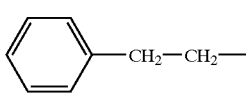 (3-phenylpropyl) | 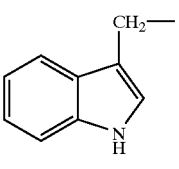 (indol-3-ylmethyl) | uracil | OH | H |
| 139 | H | —CH₃ | —CH₃ | 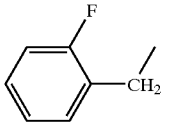 (2-fluorobenzyl) | 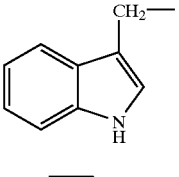 (indol-3-ylmethyl) | uracil | OH | H |
| 140 | H | —CH₃ | —CH₃ | 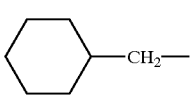 (cyclohexylmethyl) | 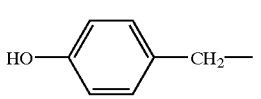 (4-hydroxybenzyl) | uracil | OH | H |
| 141 | H | —CH₃ | —CH₃ | 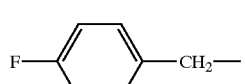 (4-fluorobenzyl) | 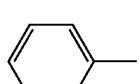 (phenyl) | uracil | OH | H |
| 142 | H | —CH₃ | —CH₃ | 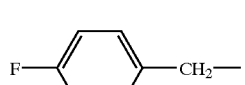 (4-fluorobenzyl) | 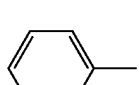 (phenyl) | uracil | OH | H |
| 143 | H | —CH₃ | —CH₃ | 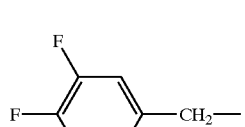 (3,4-difluorobenzyl) | 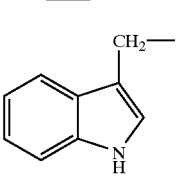 (indol-3-ylmethyl) | uracil | OH | H |

TABLE 2-continued

| | $R^1$, $R^2$ | $R^3$ | $R^4$, $R^5$ | $R^6$ | $R^7$ | $R^8$ | $R^9$ | $R^{10}$ |
|---|---|---|---|---|---|---|---|---|
| 144 | H | —CH$_3$ | —CH$_3$ | 3,4-difluorobenzyl | 4-hydroxybenzyl | uracil | OH | H |
| 145 | H | —CH$_3$ | —CH$_3$ | 4-(trifluoromethyl)benzyl | 4-hydroxybenzyl | uracil | OH | H |
| 146 | H | —CH$_3$ | —CH$_3$ | 4-(trifluoromethyl)benzyl | 1H-indol-3-ylmethyl | uracil | OH | H |
| 147 | H | H$_2$N(CH$_2$)$_4$— | —CH$_3$ | benzyl | 1H-indol-3-ylmethyl | uracil | OH | H |
| 148 | H | —CH$_3$ | —CH$_3$ | H$_2$N(CH$_2$)$_4$— | 1H-indol-3-ylmethyl | uracil | OH | H |
| 149 | H | —CH$_3$ | —CH$_3$ | benzyl | 1H-imidazol-4-ylmethyl | uracil | OH | H |
| 150 | H | PhCH$_2$OCH$_2$— | —CH$_3$ | benzyl | 4-hydroxybenzyl | uracil | OH | H |
| 151 | H | — | —CH$_3$ | benzyl | 1H-indol-3-ylmethyl | uracil | OH | H |
| 152 | H | —CH$_3$ | —CH$_3$ | 2-naphthylmethyl | 4-hydroxybenzyl | uracil | OH | H |
| 153 | H | —CH$_3$ | —CH$_3$ | 2-naphthylmethyl | 1H-indol-3-ylmethyl | uracil | OH | H |
| 154 | H | —CH$_3$ | —CH$_3$ | benzyl | 1H-indol-3-ylmethyl | uracil | OH | H |

TABLE 2-continued
| | R¹, R² | R³ | R⁴, R⁵ | R⁶ | R⁷ | R⁸ | R⁹ | R¹⁰ |
|---|---|---|---|---|---|---|---|---|
| 155 | H | —CH₃ | —CH₃ | 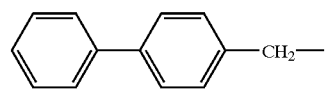 | 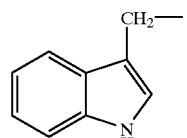 | uracil | OH | H |
| 156 | H | 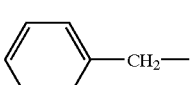 | —CH₃ | 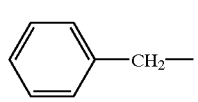 | 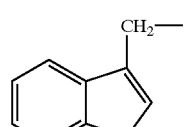 | uracil | OH | H |
| 157 | H | —CH₃ | —CH₃ | 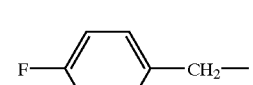 | 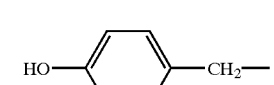 | uracil | OH | H |
| 158 | H | —CH₃ | —CH₃ | 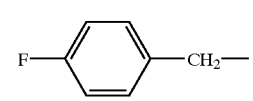 | 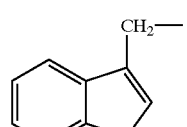 | uracil | OH | H |
| 159 | H | (CH₃)₂CHCH₂— | —CH₃ | 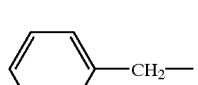 | 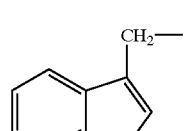 | uracil | OH | H |
| 160 | H | —CH₃ | —CH₃ | 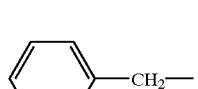 | 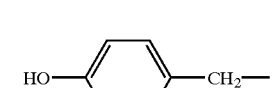 | uracil | OH | H |
| 161 | H | —CH₃ | —CH₃ | (CH₃)₂CHCH₂— | 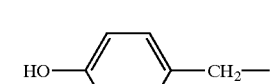 | uracil | OH | H |
| 162 | H | —CH₂CH₂SCH₃ | —CH₃ | —CH₂CH₂SCH₃ | 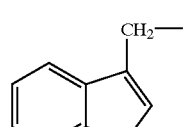 | uracil | OH | H |
| 163 | H | 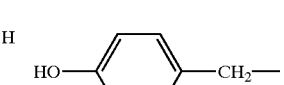 | —CH₃ | 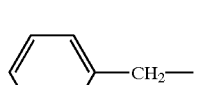 | 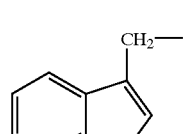 | uracil | OH | H |
| 164 | H | —CH₃ | —CH₃ | 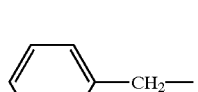 | 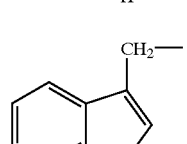 | uracil | OH | H |

TABLE 2-continued
| | R¹, R² | R³ | R⁴, R⁵ | R⁶ | R⁷ | R⁸ | R⁹ | R¹⁰ |
|---|---|---|---|---|---|---|---|---|
| 165 | H | — | —CH₃ | —CH₃ | 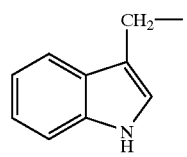 | uracil | OH | H |
| 166 | H | —CH₃ | —CH₃ | (CH₃)₂CHCH₂— | 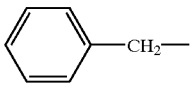 | uracil | OH | H |
| 167 | H | —CH₃ | —CH₃ | —CH₂CH₂SCH₃ | 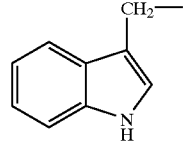 | uracil | OH | H |
| 168 | H | —CH₂CH₂SCH₃ | —CH₃ | —CH₃ | 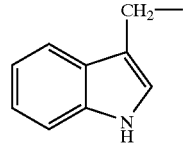 | uracil | OH | H |
| 169 | H | —CH₃ | —CH₃ | (CH₃)₂CH— | 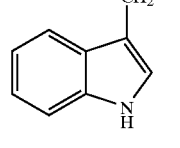 | uracil | OH | H |
| 170 | H | —CH₃ | —CH₃ | (CH₃)₂CHCH₂— | 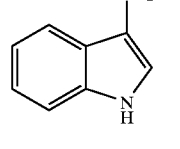 | uracil | OH | H |
| 171 | H | D—CH₃ | —CH₃ | —CH₃ | 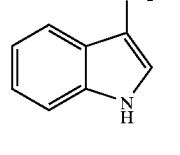 | uracil | OH | H |
| 172 | H | —CH₃ | —CH₃ | —CH₃ | 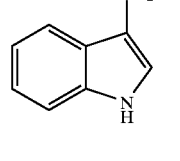 | uracil | OH | H |
| 34 | H | —CH₃ | —CH₃ | —CH₃ | 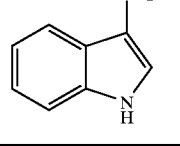 | uracil | OH | H |

A further presently preferred embodiment of this invention is a method for the synthesis of a compound of this invention comprising reacting hydrogen gas in the presence of a catalytic reducing agent in a solvent at ambient temperature with a compound having the chemical structure:

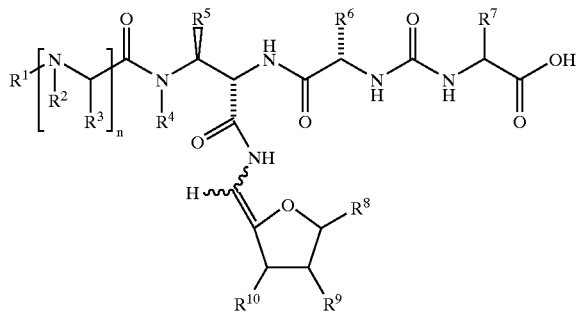

wherein, $R^1$ and $R^2$ are independently selected from the group consisting of hydrogen, alkyl, cycloalkyl, aryl, heteroaryl, heteroalicyclic, carbonyl, C-carboxy, O-carboxy, C-amido, cyano, hydroxy, alkoxy, —NRR', amino acid, polypeptidyl, combined with one another, a heteroaryl or a heteroalicyclic and, combined with $R^2$ a heteroaryl, a heteroalicyclic, a heteroaryl/aryl bicyclic, a heteroalicyclic/aryl bicyclic, a heteroaryl/heteroaryl bicyclic or a heteroalicyclic/heteroaryl bicyclic; $R^3$ is selected from the group consisting of hydrogen, alkyl, cycloalkyl, aryl, heteroaryl, heteroalicyclic, C-carboxy, C-amido and, combined with $R^2$, a heteroaryl, a heteroalicyclic, a heteroaryl/aryl bicyclic, a heteroalicyclic/aryl bicyclic, a heteroaryl/heteroaryl bicyclic and a heteroalicyclic/heteroaryl bicyclic;

$R^4$ and $R^5$ are independently selected from the group consisting of hydrogen, alkyl, aryl and heteroaryl;

$R^6$ and $R^7$ are independently selected from the group consisting of hydrogen, alkyl, cycloalkyl, alkenyl, alkynyl, aryl, heteroaryl, heteroalicyclic, C-carboxy and C-amido;

$R^8$ is uracil or dihydrouracil optionally substituted with a group selected from the group consisting of alkyl, aryl, heteroaryl, heteroalicyclic, halo, cyano, nitro and —NRR';

$R^9$ and $R^{10}$ are independently selected from the group consisting of hydrogen, halo, cyano, hydroxy, alkoxy and —NRR';

n is 0 or 1; and,

R and R' are independently selected from the group consisting of hydrogen, alkyl, cycloalkyl, aryl, carbonyl and, combined, a five-member or a six-member heteroalicyclic ring.

As used herein, a "solvent" refers to a protic or an aprotic solvent; preferably it is an aprotic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. Examples of protic solvents include, without limitation, water and alcohols.

An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride, chlorform and carbon tetrachloride. Examples of polar aprotic solvents are tetrahydrofuran, dimethylsulfoxide and dimethylformamide.

In a presently preferred embodiment of this invention, the solvent is a polar aprotic solvent, preferably dimethylformamide.

The reaction may be carried out at atmospheric pressure or at increased pressures. By "increased pressure" is meant any pressure above atmospheric pressure. In a presently preferred embodiment of this invention, the reaction is performed at atmospheric pressure.

By "ambient temperature" is meant the temperature of the reaction solution in the absence of any external heating.

"Catalytic reducing agents" as used herein refers to agents which catalyze the addition of hydrogen to unsaturated (i.e., containing double or triple bonds) compounds and are well known to those skilled in the art. Examples, without limitation, of such reagents are Palladium on carbon (Pd/C), platinum on carbon (Pt/C) and Raney Nickel (Ra—Ni). The presently preferred catalytic reducing agent is 10% Pd/C.

3. Biochemistry/Pharmacotherapy

A pharmaceutical composition comprising a compound of this invention and a pharmaceutically acceptable carrier and/or excipient is yet another presently preferred embodiment of this invention.

A method for inhibiting the growth of bacteria comprising contacting said bacteria with a compound, salt or prodrug of a compound of this invention, is a further presently preferred embodiment of this invention.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

The term "contacting" as used herein refers to bringing a compound of this invention and a target bacteria strain together in such a manner that the compound can affect the growth of the bacteria. Such "contacting" can be accomplished "in vitro," i.e., in a test tube, a petri dish or the like. In a test tube, contacting may involve only a compound and a bacterial strain of interest or it may involve whole cells. Cells may also be maintained or grown in cell culture dishes and contacted with a compound in that environment. In this context, the ability of a particular compound to affect a disorder related to the particular bacterial strain; i.e., the MIC of the compound, defined below, can be determined before use of the compounds in vivo with more complex living organisms is attempted. For cells outside the organism, multiple methods exist, and are well-known to those skilled in the art, to get the bacterial strain in contact with the compounds including, but not limited to, direct cell microinjection and numerous transmembrane carrier techniques.

It is a preferred embodiment of this invention that the Is bacteria which are inhibited by a compound of this invention are selected from the group consisting of genus Pseudomonas, Escherichia, Streptococcus, Staphylococcus, Mycobacteria, Enterococcus and Haemophilus.

A method for treating a bacterial infection in a patient in need of such treatment comprising administering a therapeutically effective amount of a compound, salt or prodrug of a compound of this invention to the patient is a further presently preferred embodiment of this invention.

As used herein, the terms "treat", "treating" or "treatment" refer to a method of alleviating or abrogating a bacteria-caused infection and/or its attendant symptoms.

A "bacterial infection" refers to the multiplication of infection-causing bacteria in the body of a patient.

As used herein, "administer," "administering" or "administration" refers to the delivery of a compound, salt or prodrug of the present invention or of a pharmaceutical composition containing a compound, salt or prodrug of this invention to a patient in a manner suitable for the treatment of a bacterial infection.

A "patient" refers to any higher organism that is susceptible to bacterial infections. Examples of such higher organisms include, without limitation, mice, rats, rabbits, dogs, cats, horses, cows, pigs, sheep, fish and reptiles. Preferably, "patient" refers to a human being.

The term "therapeutically effective amount" as used herein refers to that amount of the compound being administered which will relieve to some extent one or more of the symptoms of the bacterial infection being treated. Preferably, a therapeutically effective amount is an amount sufficient to cure the infection. By "curing" is meant that the symptoms of active infection are eliminated including the elimination of excessive numbers of viable bacterial involved in the infection.

A method for preventing a bacterial infection in a patient comprising administering to said patient a prophylactically effective amount of a compound, salt or prodrug of a compound of this invention is a further presently preferred embodiment of this invention.

The term "prophylactically effective amount" means an amount of a compound or compounds of this invention sufficient to prevent the establishment of a clinically significant population of bacteria in a patient; that is, an amount capable of establishing an infection. Preferably, a prophylactically effective amount is that amount which prevents the establishment of any population of the target bacteria.

Another presently preferred embodiment of this invention that the bacterial infection which is treated with a compound, salt or prodrug of this invention consists of a bacterial infection caused by a bacteria selected from genus Pseudomonas, Escherichia, Staphylococcus, Streptococcus, Enterococcus, Mycobacteria and Haemophilus.

Likewise, it is a presently preferred embodiment of this invention that the bacterial infection which is treated with a compound, salt or prodrug of this invention is a bacterial infection caused by *P. aeruginosa, E. coli, M. fortuitum, M. tuberculosis* and *H. influenzae*.

In another presently preferred embodiment of this invention, the bacterial infection being treated or prevented is selected from the group consisting of wound infection, burn lesion infection, urinary tract infection, enteritis, cystitis, peritonitis, gasterointestinal infection, colitis, pneumonia, strep throat, scarlet fever, impetigo, rheumatic fever, endocarditis, tuberculosis, bacterial meningitis, conjunctivitis, upper respiratory infection and endocarditis.

Finally, it is a presently preferred embodiment of this invention that the patient to be treated with a compound, salt or prodrug of this invention is a human.

DETAILED DESCRIPTION OF THE INVENTION

1. The Compounds

The increasing occurrence of multi-resistant bacterial I- infections in both nosocomial and community settings has given rise to the need for novel therapies to treat such infections. Strategies to this end have included modification of existing classes of antibiotics, addition of agents to potentiate existing antibiotics in resistant organisms, and the identification of new classes of antibiotics with novel modes of action that are not cross-resistant with old classes. With regard to this last approach, two structurally related subsets of the uridyl peptide antibiotics (UPAs), the pacidamycins and the mureidomycins (see table 1), have demonstrated in vivo bioavailability. Furthermore, the mureidomycins have also shown in vivo efficacy against *P. aeruginosa*. The mode of action of the mureidomycins have been shown to be inhibition of the bacterial enzyme translocase I, an integral part of cell-wall biosynthesis in most Gram-positive and Gram-negative bacteria. Translocase I in not the target of any S agents in current clinical use and for this reason, is an attractive target. Furthermore, β-lactam- and fluoroquinolone-resistant strains of *P. aeruginosa* have been shown to remain sensitive to mureidomycin. In addition, unlike other translocase inhibitors such as tunicamycin and amphomycin, which also target mammalian enzymes, the pacidamycins and mureidomycins appear to be specific for their bacterial targets.

While these antibiotics are the only compounds presently documented to possess selective activity against *Pseudomonas aeruginosa*, such a limited spectrum of activity is generally not As of great utility in a clinical setting where broad-spectrum empiric therapy is often necessary. Mureidomycins, however, have been shown to also be a potent inhibitor of translocase enzyme in *E. coli* (Inukai, M., *Antimicrobial Agents and Chemotherapy*, 1993, 980 983) suggesting that broader spectrum antibiotic compounds based on the mureidomycin (and, it would be expected, the related pacidamycin and napsamycin) structures ought to be achievable. The naturally-occurring pacidamycins and mureidomycins also suffer from the additional limitation that, while *P. aeruginosa* is initially very susceptible to these compounds, resistance tends to develop quite rapidly (frequency ~$10^{-6}$). We therefore undertook the synthesis of the compounds of this invention, i.e., dihydro mureidomycin, pacidamycin and napsamycin derivatives, to address these issues.

Central to our approach to the synthesis of UPA derivatives was our discovery that hydrogenation of naturally-occurring pacidamycin D gave the corresponding dihydro derivative that not only displayed the antibacterial spectrum of pacidamycin D but was also an inhibitor of *E. coli* translocase. Forced hydrogenation gave the tetrahydro derivative of pacidamycin D in which not only the exocyclic double bond but the endocyclic double bond of the uracil moiety was reduced as well. These compounds also inhibited translocase I and exhibited antibacterial activity.

The general synthetic scheme employed to prepare the compounds of this invention is described below. It will be appreciated by those skilled in the art that other synthetic pathways for forming the compounds of the invention are available and that the following is offered by way of example and not limitation.

Prior to embarking on the total synthesis of dihydro derivatives of the UPAs, i.e., the compounds of this invention, it was necessary to determine the absolute stereochemistry of all the chiral centers in the naturally occurring molecule. To accomplish this, three assumptions were made. First, that the stereochemistry at the 1'-ribose center is identical to that of uridine. Second, that the stereochemistry of the 2'-hydroxyl group is also the same as that of uridine. Third, that the C-terminal amino acid residue is (S), an assumption predicated on actual studies performed but not presented herein.

A pacidamycin was hydrolyzed according to a literature procedure for mureidomycins (Isono, F., et al., *J. Antibiot.* (Tokyo), 1989, 42:667–73). The 3-methylamino-2-aminobutyric acid obtained in the hydrolysis was isolated by size-exclusion chromatography and the NMR coupling constant, $J_{H\alpha-H\beta}$, was found to be 4.4 Hz in 2N DCl in $D_2O$. A minor component having a $J_{H\alpha-H\beta}$ of 2.8 Hz was also present and appeared to be a diasteriomer of the major component. The major diasteriomer was surmised to be that derived from the pacidamycin since re-subjection of the mixture to the hydrolysis conditions caused equilibration to nearly a 1:1 mixture of the two components. In view of literature studies on the analogous 2,3-diaminobutyric acid (Hausmann, W. K., *J. Antibiot.* (Tokyo), 1969, 22:207–10), the stereochemistry was determined, based on the coupling constant, to be either (2S,3S) or (2R,3R).

Azetidinone 7 was prepared according to the method of Miller, et al. using some of the modifications of Floyd, et al. (Miller, et al., *J. Am. Chem. Soc.,* 1980, 102:7026–7032; Floyd, et al., *J. Org. Chem.,* 1982, 47:5160–5167). The azetidinone ring of 7 was hydrolyzed using NaOH to give compound 8. The N-methyl group was introduced by reductive amination with formaldehyde to give 9 (Scheme 1). Compound 9 was deprotected by hydrogenation at 50 psi to provide compound 10. Compound 10 was further deprotected by removal of the Boc (butoxycarbonyl) group and the resulting 3-methylamino-2-aminobutyric acid 11 showed an identical $^1H$ NMR spectrum when mixed together with the sample isolated from the natural product, thus confirming the initial assignment of relative stereochemistry.

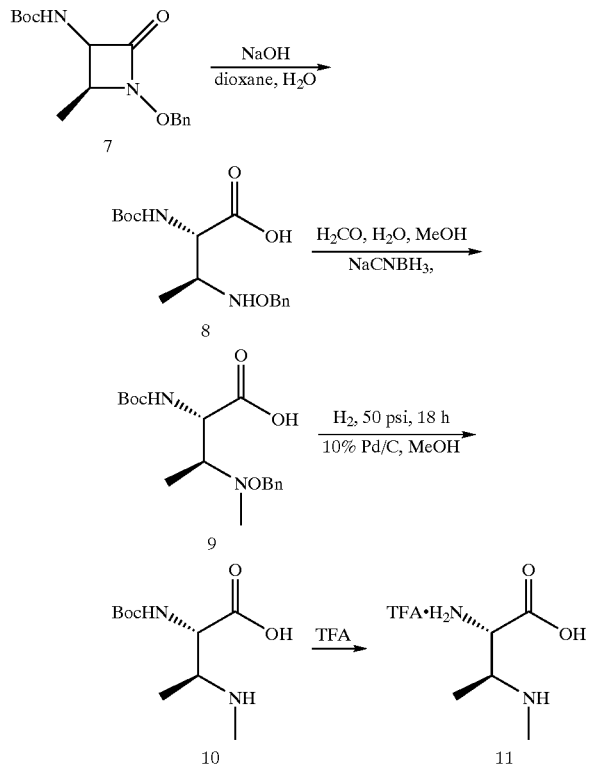

SCHEME 1

The synthetic (2S,3S)- and (2R,3R)-3-methylaminobutyric acids were separated on HPLC (Hypersil ODS column, 5 μm particle size) using a chiral mobil phase (4 mM N,N-dipropyl-L-alanine, 2 mM $Cu(OAc)_2$, pH 5). Injection of the natural 3-methylaminobutyric acid obtained from acid hydrolysis of a pacidamycin under the same conditions showed a peak with the same retention time as the (2S,3S) 3-methylaminobutyric acid. Co-injections with both synthetic samples confirmed the (2S,3S) absolute stereochemistry.

Compound 12 (Scheme 2) was obtained according to a literature procedure (Hakimelahi, C. H., et al., *Tetrahedron Lett.,* 1981, 22:5243). The free hydroxyl group was activated for radical reduction using thiocarbonyldiimidazole. Radical reduction was performed using azacyclohexylcarbonitrile as the initiator and tributyltin hydride as reducing agent, to give compound 13. The 5'-silyl ether was then selectively removed using 80% acetic acid in $H_2O$ to give compound 14. Compound 14 was treated with p-tosyl chloride and the resulting tosylate 15 was converted to azide 16. Compound 16 afforded the desired nucleoside 18 upon deprotection with TBAF and reduction with 1,3-propanedithiol.

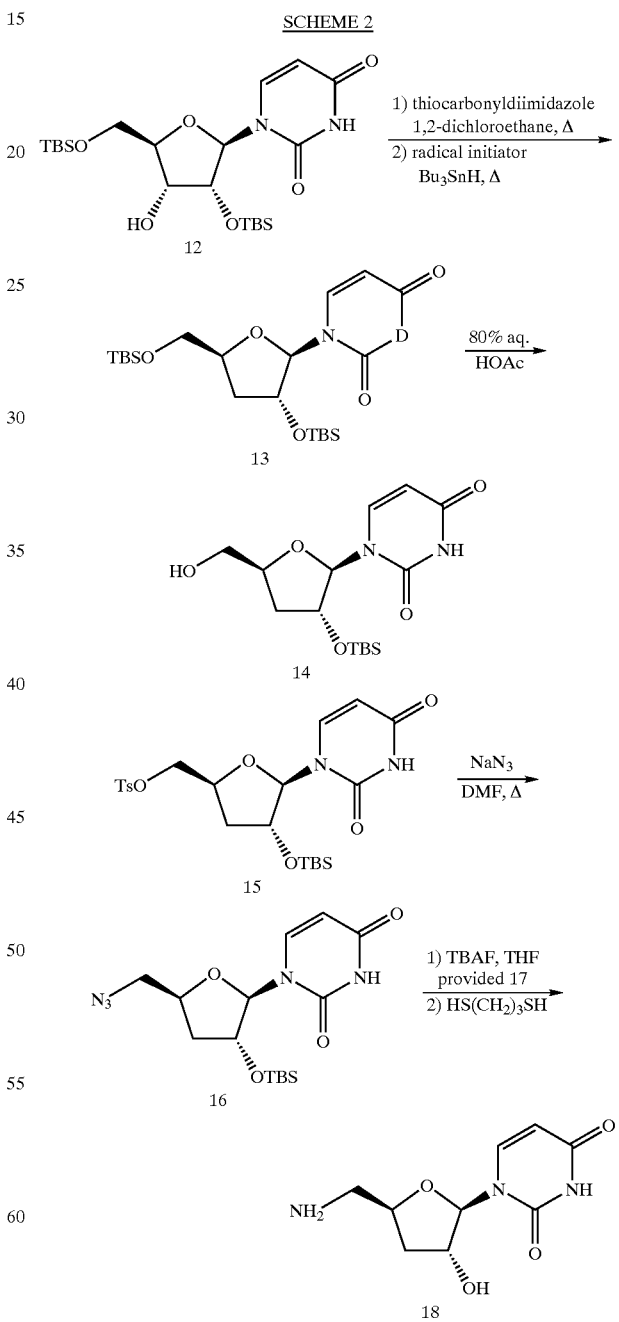

SCHEME 2

Compound 19 (Scheme 3) was prepared according to literature procedures (Corey, E. J., *J. Org. Chem.,* 1984, 49:4735). The stereochemistry at the 4' center was removed concomitantly with deoxygenation at the 3' site in a base-mediated elimination step. The optimized procedure involved trapping the resulting free alcohol as its tert-butyldimethylsilyl ether before isolation. The desired stereochemistry (R) at the 4' center was obtained by hydrogenation directed to the top face of the molecule by the bulky silyl ether protecting group. The desired stereoisomer was obtained in a 9:1 ratio relative to the undesired stereoisomer, which was removed during recrystallization of 21. Quick treatment with 90% TFA in $CH_2Cl_2$ selectively deprotected the carboxylic acid, which was then subjected to a two-step activation/reduction sequence affording alcohol 22. Nitrogen functionality was introduced by tosylation of 22 followed by azide displacement, yielding compound 24. The silyl ether was removed under standard conditions, and, finally, azide reduction using neat 1,3-propanedithiol was employed to give pure 26 after an extractive purification.

SCHEME 3

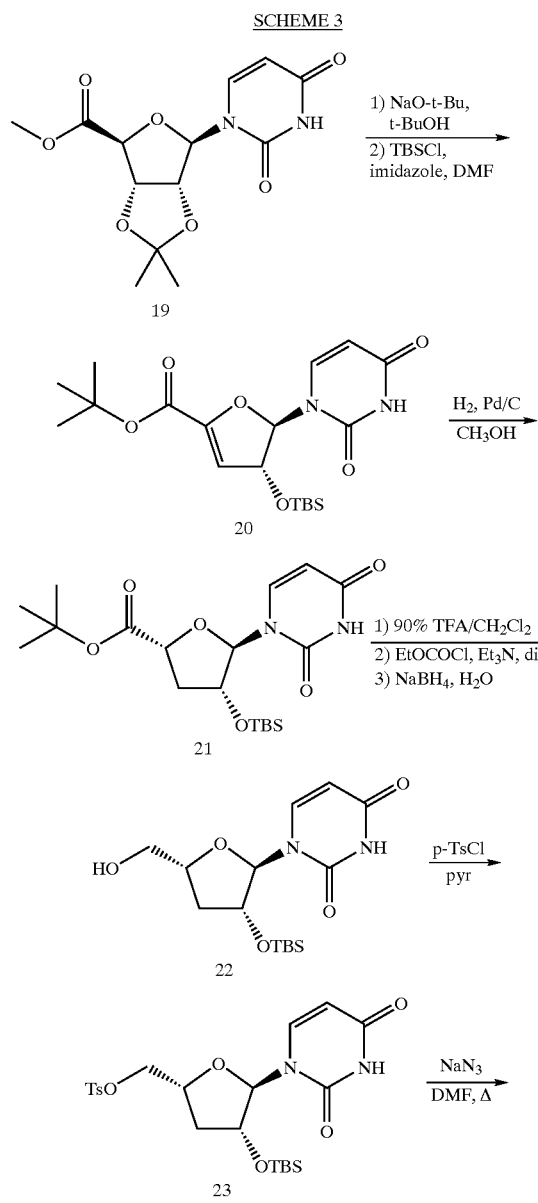

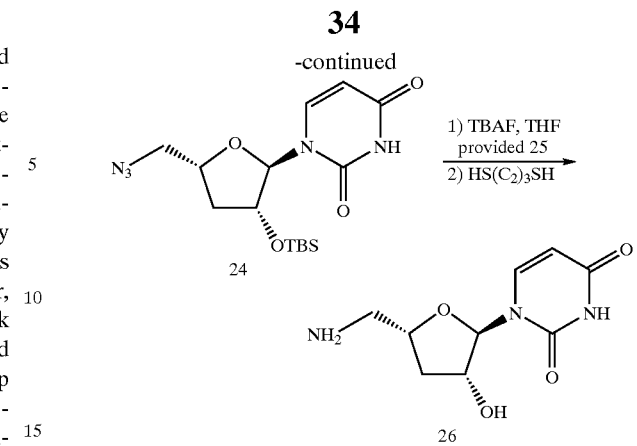

The urea portion of the target molecule was prepared according to the method of Majer and Randad (*J. Org. Chem.*, 1994, 59: 1937–1938). H-Ala-OBn (O-benzyl) and H-Trp-OtBu (o-t-butyl) were condensed with triphosgene and the resulting unsymmetrical urea was debenzylated by hydrogenation at 1 atm. The resulting carboxylic acid was esterified under standard conditions to give the pentafluorophenyl ester 29 (Scheme 4).

SCHEME 4

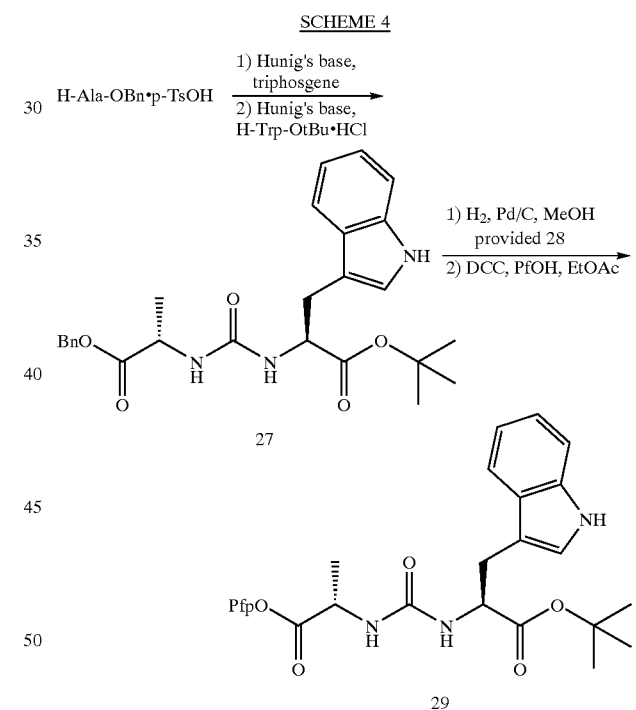

The (2S,3S)-3-methylamino-2-(tert-butoxyformamido) butyric acid was coupled with the pentafluorophenyl ester of Fmoc-L-alanine (Scheme 5). The resulting dipeptide 30 was activated as its pentafluorophenyl ester under standard conditions and coupled with aminonucleoside 26 providing compound 31. The Boc group of compound 31 was removed and the resulting amine was coupled with 29 by stirring for 8 h in DMF, thus completing the synthesis of a fully protected dihydropacidamycin. The tert-butyl ester protecting group was removed by treatment with TFA. Finally, cleavage of the Fmoc group and subsequent HPLC purification provided compound 34 which displayed comparable biological activity to dihydropacidamycin D.

SCHEME 5

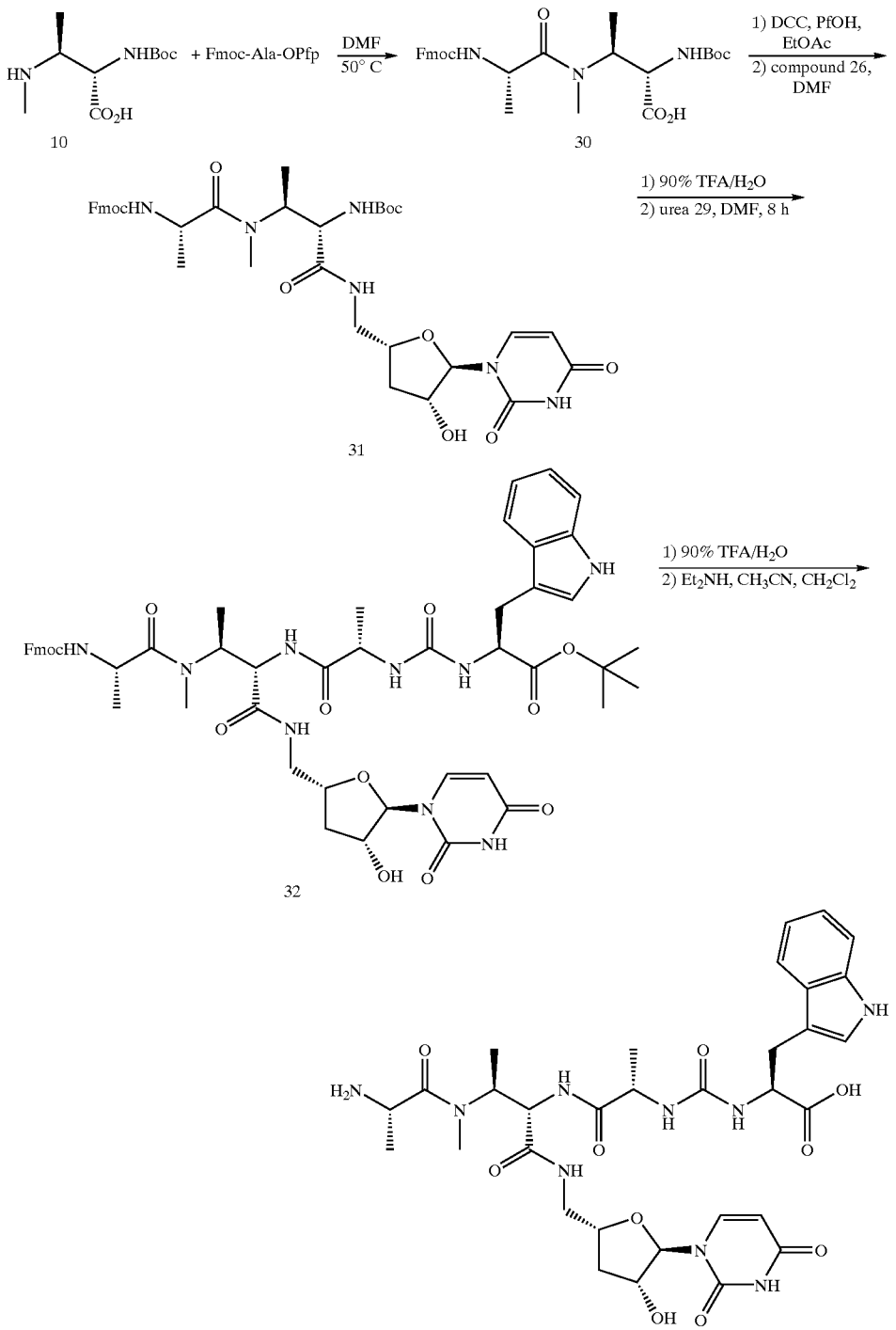

2. Pharmaceutical Compositions and Use

A compound of the present invention, a prodrug thereof or a physiologically acceptable salt of either the compound or its prodrug, can be administered as such to a patient or it can be administered in pharmaceutical compositions in which the foregoing materials are mixed with suitable carriers or excipient (s). Techniques for formulation and administration of drugs may be found in "Remington's Pharmacological Sciences," Mack Publishing Co., Easton, Pa., latest edition.

Routes of Administration

As used herein, "administer" or "administration" refers to the delivery of a compound, salt or prodrug of the present invention or of a pharmaceutical composition containing a compound, salt or prodrug of this invention to a patient in a manner suitable for the prevention or treatment of a bacterial infection.

Suitable routes of administration may include, without limitation, oral, rectal, transmucosal or intestinal administration or intramuscular, subcutaneous, intramedullary, intrathecal, direct intraventricular, intravenous, intraperitoneal, intranasal, or intraocular injections. The preferred routes of administration are oral and parenteral.

Compositions/Formulations

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks, solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methylcellulose, hydroxypropylmethylcellulose sodium carboxymethylcellulose, and/or polyvinylpyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, on without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmaceutically acceptable oil), with ion exchange resins, or as a sparingly soluble derivative such as, without limitation, a sparingly soluble salt.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days, Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the compounds of this invention may be provided as physiologically acceptable salts wherein the claimed compound may form the negatively or the positively charged species. Examples of salts in which the compound forms the positively charged moiety include, without limitation, ammonium salts such as the hydrochloride, sulfate, carbonate, lactate, tartrate, maleate and succinate. The nitrogen atom of the ammonium group is a nitrogen atom contained within the structure of a compound of this invention. Salts in which a compound of this invention forms the negatively charged species include, without limitation, the sodium, potassium, calcium and magnesium salts formed by the reaction of a carboxylic acid group contained within the structure of a compound of this invention with an appropriate base (e.g., sodium hydroxide (NaOH), potassium hydroxide (KOH), calcium hydroxide (Ca(OH)$_2$), etc.)

Dosage

Pharmaceutical compositions suitable for use in the present invention include compositions wherein the active ingredients are contained in an amount sufficient to achieve the intended purpose, i.e., the treatment or prevention of bacterial infection.

More specifically, a therapeutically effective amount means an amount of compound effective to prevent, alleviate or ameliorate symptoms of infection, preferably by directly or indirectly eliminating the causal bacteria.

Determination of a therapeutically effective amount is well within the capability of those skilled in the art, especially in light of the detailed disclosure provided herein.

The proper dosage will depend on such things as the severity and course of the infection, previous therapy, the patient's health status, his or her response to the drugs, etc., all of which are well within the knowledge, expertise and judgment of the treating physician.

In general, however, a suitable effective dose of a compound of this invention will be in the range of 0.1 to 1000 milligram (mg) per recipient per day, preferably in the range of 1 to 100 mg per day. The desired dosage may be administered in one dose or, preferably, in two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 250 mg/kg of patient body weight, between one and four times per day.

Once improvement of the patient's conditions has occurred, a maintenance dose may be administered if desired by the treating physician. Subsequently, the dosage or the frequency of administration, or both, can be reduced, as a function of the response of the patient, to a level at which the improved condition is retained. When the symptoms have been alleviated to the desired level, treatment can cease. Patients may, however, require intermittent treatment on a long-term basis upon any recurrence of the disease symptoms.

As well as being useful to treat patients with an on-going infection, the compounds of this invention may be used in a prophylactic manner. That is, compositions containing the compounds of the invention are administered to a patient susceptible to or otherwise at risk of a particular infection. In this use, the precise amounts again depend on the patient's state of health, weight, and the like.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition.

4. Synthesis

It will be appreciated by those skilled in the art that there are numerous approaches to the synthesis of the complex compounds of this invention. Thus, the following synthetic procedures are presented by way of example only and are not to be construed as limiting the scope of this invention in any manner whatsoever.

Dihydropacidamycin D (Compound 3)

In 8 mL of DMF was dissolved pacidamycin D (25 mg, 0.035 mmol). The solution was purged with $N_2$ and 25 mg of 10% Pd/C was added. The reaction was stirred vigorously with a magnetic Liz stirrer under 1 atmosphere of hydrogen and the progress of the reaction was monitored by mass spectrometry. When there was no longer any starting material present, the mixture was purged for 5 min with $N_2$ and the catalyst removed by filtration. The resulting residue was purified on a semi-preparative C-18 HPLC column with UV detection at 260 nm (flow rate 10 mL/min, 0–100% acetonitrile in 0.1% aq. TFA ramped over 20 min). Lyophilization of the product containing fractions provided 1.8 mg of the desired compound 3 as the white TFA salt (0.0022 mmol, 6% yield).

Mass calculated for $C_{32}H_{43}N_9O_{10}$: 713.3; mass found (M–H)$^-$: 712. Mass spectral analysis of the product indicated that it contained approximately 40% of the tetrahydrogenated product.

Tetrahydropacidamycin D (Compound 4)

The procedure employed was identical to that for dihydropacidmycin D, except that hydrogenation was continued until all pacidamycin D (100 mg, 0.14 mmol) and dihydropacidamycin D were consumed, as determined by mass spectrometry. HPLC purification as above provided 5.2 mg of the desired compound 4 as the white TFA salt (0.0063 mmol, 5% yield).

Mass calculated for $C_{32}H_{45}N_9O_{10}$: 715.3; mass found (M–H)$^-$: 714.

Dihydropacidamycin 1 (Compound 5)

The procedure for hydrogenation of pacidamycin 1 (21 mg, 0.024 mmol) was identical to that for pacidmycin D. As before, reaction completion was determined by mass spectral analysis. HPLC purification gave 2.0 mg of the desired compound 5 as the white TFA salt (0.0023 mmol, 10% yield).

Mass calculated for $C_{41}H_{52}N_{10}O_{12}$ : 876.4; mass found (M–H)$^-$: 875.

Dihydropacidamycin 4 (Compound 6)

The procedure for the hydrogenation of pacidamycin 4 (95 mg, 0.12 mmol) was identical to that for dihydropacidamycin D, except that completion was determined by NMR instead of mass spectrometry. HPLC purification gave 25 mg of 6 as the white TFA salt (0.031 mmol, 26% yield).

Mass calculated for $C_{38}H_{47}N_{19}O_{11}$: 805.3; mass found $(M-H)^-$: 806.

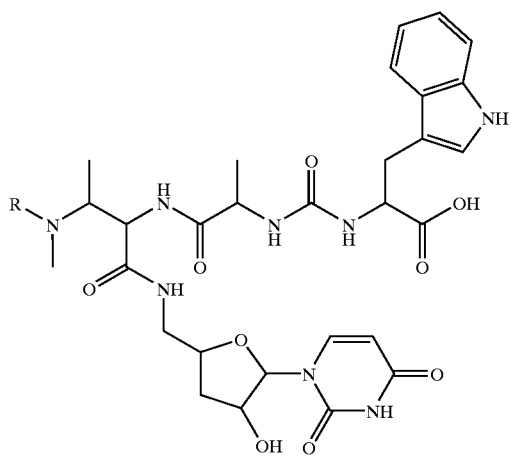

Compound 3   R = alanyl
Compound 5   R = alanyl-m-tyrosyl
Compound 6   R = m-tyrosyl

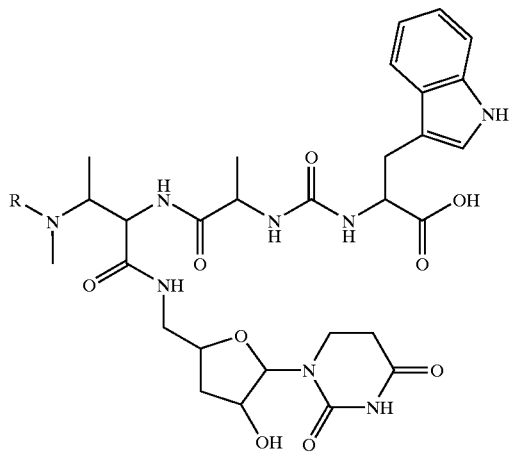

Compound 4   R = alanyl

Benzyl (2S,3S)-3-benzyloxyamino-2-(tert-butoxyformamido)butyric Acid (Compound 8)

To a solution of (3S,4S)-1-benzyloxyamino-3-N-tert-butyloxycarbonyl-4-methyl-2-azetidinone (Compound 7, Miller, M. J., et al., *J. Am. Chem. Soc.,* 1980, 102:7026–32; Floyd, D. M., et al., *J. Org. Chem.,* 1982, 47:5160–67) (5.635 g, 18.4 mmol), which was prepared using a mesylate-displacement mediated N—C(4) bond closure instead of a diethyl azodicarboxylate triphenylphosphine-mediated ring closure, in 35 mL 1:1 water/dioxane, at ambient temperature, was added dropwise a 1M solution of sodium hydroxide (18.4 mL, 18.4 mmol) over 1 hour. One-half hour after addition was completed, 0.15 additional equivalent (2.8 mmol) of sodium hydroxide was added and the solution was stirred for an additional hour to ensure completion of the reaction. The reaction mixture was then concentrated to ¼ volume in vacuo. The aqueous mixture was acidified to pH 1 with 1M hydrochloric acid and then extracted with ethyl acetate. The organic layer was washed with 10% sodium bicarbonate and water. The combined organic layers were dried over anhydrous sodium sulfate, filtered and evaporated in vacuo to afford 5.94 g of (2S,3S)-3-benzyloxyamino-2-(tert-butoxyformamido)butyric acid 8 (quantitative yield).

$^1$H NMR (400 MHz, $CD_3OD$) δ0.98 (d, 3, J=6.8), 1.42 (s, 3), 3.49 (dq, 1, J=6.8; 4.4), 4.57 (bs, 1), 4.64 (d, 1, J=11.6), 4.68 (d, 1, J=11.6), 7.35 (m, 5).

IR (KBr pellet, $cm^{-1}$) 3600–2400, 2305, 1715, 1500, 1368, 1265, 1163, 1023, 740.

Mass calculated for $C_{16}H_{24}N_2O_5$: 324.17; mass found for $(M-H)^-$: 323.1.

(2S,3S)-3-((Benzyloxy)methylamino)-2-(tert-butoxyformamido)butyric Acid (Compound 9)

To a solution of (2S,3S)-3-(benzyloxyamino)-2-(tert-butoxyformamido)butyric acid 8 (8.5 g, 26.2 mmol) in 70 mL methanol was added, at 0° C., sodium cyanoborohydride (1.65 g, 26.2 mmol) over 15 minutes, followed by addition of 37 wt % aqueous formaldehyde (1.92 mL, 25.7 mmol) over 0.5 hour. The reaction was allowed to warm to ambient temperature and then stirred for 4 hours before being concentrated in vacuo. The residue was taken in 200 mL water and the solution was basified with potassium carbonate. The aqueous solution was washed with ether, acidified to pH 2 with 1M hydrochloric acid and then extracted with ethyl acetate. The organic layers were then washed with water, dried over anhydrous sodium sulfate, filtered and evaporated in vacuo to afford 8.51 g of (2S,3S)-3-((benzyloxy)methylamino)-2-(tert-butoxyformamido)butyric acid 9 (96% yield).

1H NMR (400 MHz, $CD_3OD$) δ1.08 (d, 3, J=6.8), 1.42 (s, 9), 2.56 (s, 3), 3.13 (dq, 1, J=6.8; 4.8), 4.50 (d, 1, J=4.8), 4.62 (s, 2), 7.26 (m, 5).

IR (KBr pellet, $cm^{-1}$) 3500–2400, 2305, 1715, 1500, 1368, 1265, 1164, 1023, 747.

Mass calculated for $C_{17}H_{26}N_2O_4$: 338.18; mass found for $(M-H)^-$: 337.2.

(2S,3S)-3-Methylamino-2-(tert-butoxyformamido) butyric Acid (Compound 10)

A solution of (2S,3S)-3-((benzyloxy)methylamino)-2-(tert-butoxyformamido)butyric acid 9 (2.4 g, 14.8 mmol) in 20 mL methanol was added under nitrogen to a suspension of 10% palladium on charcoal (0.6 g, 25 wt %) in 20 mL methanol in a Parr hydrogenator flask. The mixture was placed on the Parr hydrogenator and hydrogenated at 50 psi for 18 hours. The catalyst was removed by filtration and the filtrate evaporated in vacuo. The residue was then lyophilized, affording 1.55 g of (2S,3S)-3-methylamino-2-(tert-butoxyformamido)butyric acid 10 as a white solid (95% yield).

$^1$H NMR (400 MHz, $CD_3OD$) δ1.26 (d, 3, J=6.8), 1.48 (s, 9), 2.76 (s, 3), 3.72 (dq, 1, J=6.8; 4.0), 4.66 (bs, 1).

IR (KBr pellet, $cm^{-1}$) 3600–2500, 2344, 1702, 1676, 1524, 1203, 1056, 722.

Mass calculated for $C_{10}H_{20}N_2O_4$: 232.14; mass found for $(M+H)^+$: 233.2, $(M+Na)^+$: 255.1.

1-[3'-Deoxy-2',5'-di-(tert-butyldimethylsilyloxy)-β-D-ribofuranosyl)uracil (Compound 13)

To a solution of 2',5'-di-tert-butyldimethylsilyloxy-uridine (Hakimelahi, C. H., *Tetrahedron Lett.,* 1981, 22:5243) 12 (10.69 g, 22.6 mmol) in 80 mL of dichloroethane was added thiocarbonyldiimidazole (8.00 g, 45.2 mmol) in one portion. The resulting mixture was heated at reflux under nitrogen for 1.5 hours, cooled to ambient temperature and quenched by addition of 50 mL of water. The phases were separated and the aqueous layer was extracted with dichloromethane. The combined organic layers were washed with cold 1M aqueous hydrochloric acid, saturated aqueous sodium bicarbonate, and brine. The organic extracts were dried over anhydrous sodium sulfate and concentrated in vacuo. The residue was used in the next reaction without further purification.

To a solution of the thiocarbonyl compound in 100 mL of degassed (three freeze-pump-thaw cycles) xylene was added azacyclohexylcarbonitrile (3.0 g, 2.3 mmol) followed by tributyltin hydride (12 mL, 45 mmol). The reaction mixture was heated at reflux for 3 hours and then concentrated in vacuo. The residue was purified by silica gel chromatography (eluant: hexane/chloroform 2/1 to 1/5 followed by hexanes/ethyl acetate 3/1) to give 6.12 g of 1-[3'-deoxy-2', 5'-di-(tert-butyldimethylsilyloxy)-β-D-ribofuranosyl]uracil 13 (59% yield).

1H NMR (CDCl$_3$, 400 MHz) δ0.12 (s, 6), 0.91 (s, 18), 1.71 (dd, 1, J=12.8, 4.0), 2.00–2.07 (m, 1), 3.72 (d, 1, J=12.0), 4.17(d, 1, J=12.0), 4.35 (d, 1, J=4.0), 4.47–4.50 (m, 1), 5.63 (d, 1, J=8.0), 5.71 (s, 1), 8.15 (d, 1, J=8.0), 9.57 (bs, 1).

1-[3'-Deoxy-2'-(tert-butyldimethylsilyloxy)-β-D-ribofuranosyl]uracil (Compound 14)

A solution of 1-[3'-deoxy-2',5'-di-(tert-butyldimethylsilyloxy)-β-D-ribofuranosyl]uracil 13 (6.8 g, 15 mmol) in 200 mL 80% aqueous acetic was stirred at ambient temperature, under nitrogen, for 24 hours and then concentrated in vacuo. The residue was purified by silica gel chromatography (eluant: hexane/ethyl acetate 1/1 followed by neat ethyl acetate) to give 3.32 g of 1-[3'-deoxy-2'-tert-butyldimethylsilyloxy-β-D-ribofuranosyl]uracil 14 (yield 65%) and 1-[3'-deoxy-β-D-ribo-furanosyl]uracil (2.0 g, 30%).

1H NMR(CDCl$_3$, 400 MHz) δ0.09 (s, 3), 0.14 (s, 3), 0.90 (s, 9), 1.80–1.85 (dd, 1, J=12.8; 5.6), 2.05–2.11 (m, 1), 3.75 (dd, 1, J=12.0, 4.0), 4.1 (1, dd, J=12.0, 1.6), 4.47–4.50 (1, m), 4.51–4.54 (1, m), 5.64 (s, 1), 5.68 (d, 1, J=8.0), 7.89 (d, 1, J=8.0), 8.99 (bs, 1).

1-[5'-Azido-3',5'-dideoxy-2'-(tert-butyldimethylsilyloxy)-β-D-ribofuranosyl]uracil (Compound 16)

To a solution of 1-[3'-deoxy-2'-(tert-butyldimethylsilyloxy)-β-D-ribofuranosyl]uracil 14 (0.45 g, 1.3 mmol) in 7 mL of pyridine was added tosyl chloride (0.75 g, 3.9 mmol) in one portion. The resulting mixture was stirred under nitrogen overnight during which time it slowly warmed to ambient temperature. The reaction mixture was then quenched by addition of ice. The reaction mixture was partitioned between water and dicholoromethane. The aqueous layer was extracted with dichloromethane and the organic extracts were washed with aqueous 1 N hydrochloric acid and with brine. The combined organic layers were dried over anhydrous sodium sulfate and concentrated in vacuo. The residue was used in the next reaction without further purification.

To a solution of the crude tosylate 15 (0.69 g, 1.4 mmol) in 8 mL DMF was added lithium azide (0.20 g, 4.1 mmol). The resulting mixture was stirred under nitrogen at 40° C. for 2 hours and then at ambient temperature overnight. The reaction mixture then was diluted with ethyl acetate and washed with water. The organic layer was dried over anhydrous sodium sulfate and concentrated in vacuo. The residue was purified by silica gel chromatography (eluant: hexane/ethyl acetate 1/1) to give 0.401 g of 1-[5'-azido-3',5'-dideoxy-2'-(tert-butyldimethylsilyloxy)-β-D-ribofuranosyl]uracil 16 (yield 83%).

$^1$H NMR (CD$_3$OD, 400 MHz) δ0.10 (s, 3), 0.15 (s, 3), 0.90 (s, 9), 1.85–1.89 (m, 1), 1.91–1.94 (m, 1), 3.67 (dd, 1, J=13.6; 4.0), 3.83 (dd, 1, J=13.6; 3.2), 4.40–4.53 (m, 1), 4.53–4.57 (m, 1) , 5.69 (s, 1), 5.75 (d, 1, J=8.0), 7.66 (d, 1, J=8.0), 9.3 (bs, 1).

1-[5'-Azido-3',5'-dideoxy-β-D-ribofuranosyl]uracil (Compound 17)

To a solution of 1-[5'-azido-3',5'-dideoxy-2'-(tert-butyldimethylsilyloxy)-β-D-ribofuranosyl]uracil 16 (0.474 g, 1.29 mmol) in 10 ml of tetrahydrofuran was added tetrabutylammonium fluoride 1M in tetrahydrofuran (1.5 mL, 1.5 mmol) in one portion. The resulting mixture was stirred under nitrogen for 30 minutes and then concentrated in vacuo. The residue was purified by silica gel chromatography (eluant: ethyl acetate) to give 0.27 g of 1-[5'-azido-3',5'-dideoxy-β-D-ribofuranosyl]uracil 17 (84% yield).

$^1$H NMR (CD$_3$OD, 400 MHz) δ1.94–1.99 (m, 1), 2.02–2.10 (m, 1), 3.56 (dd, 1, J=13.6; 5.2), 3.69 (dd, 1, J=13.6; 3.6), 4.37–4.40 (m, 1), 4.47–4.51 (m, 1), 5.70 (d, 1, J=8.0), 5.75 (d, 1, J=2.0), 7.73 (d, 1, J=8.0).

1-[5'-Amino-3',5'-dideoxy-β-D-ribofuranosyl]uracil (Compound 18)

To a solution of 1-[5'-azido-3',5'-dideoxy-β-D-ribofuranosyl]uracil 17 (0.37 g, 1.5 mmol) in 15 mL methanol was added 1,3-propanedithiol (1.5 mL, 0.15 mmol) in one portion. The resulting mixture was stirred for five days at ambient temperature. The reaction mixture was then concentrated in vacuo. The residue was dissolved in water and washed with dichloromethane. The aqueous layer was concentrated in vacuo to give 0.31 g of 1-[5'-amino-3',5'-dideoxy-β-D-ribofuranosyl]uracil (93% yield).

$^1$H NMR (CD$_3$OD, 300 MHz) δ1.95–2.03 (m, 1), 2.05–2.12 (m, 1), 2.95–3.06 (m, 2), 4.45–4.96 (m, 2), 5.79 (d, 1, J=8.1), 5.82 (d, 1, J=1.8), 7.78 (d, 1, J=8.1).

Tert-Butyl (4R,5R)-4-(tert-butyldimethylsiloxy)-5-uracil-4,5-dihydro-2-furoate (Compound 20)

To a solution of tert-butyl 2',3'-O-isopropylideneuridine-5'-carboxylate (Corey, E. J., et al., J. Org. Chem., 1984, 49:4735) 19 (2.53 g, 7.47 mmol) in 50 mL 2-methyl-2-propanol (dried over 4A° molecular sieves) was added, with rapid stirring, potassium tert-butoxide (1.68 g, 14.9 mmol). As soon as all of the potassium tert-butoxide was dissolved, glacial acetic acid it was added dropwise until the pH of the solution was 7.5–8. The resulting mixture was concentrated in vacuo to a yellow crude solid which was held under vacuum for one hour. To the residue in 30 mL dimethylformamide was added imidazole (2.54 g, 7.47 mmol) followed by tert-butyldimethylsilyl chloride (5.63g, 36.3 mmol). The reaction mixture was stirred at ambient temperature under nitrogen for 1 hour and then evaporated in vacuo with heating to no greater than 45° C. The residue was partitioned in a separatory funnel between 200 mL of 0.5 N aqueous hydrochloric acid and 200 mL of hexanes/ethyl acetate (3.5:1). The organic layer was washed with 1N aqueous hydrochloric acid, saturated aqueous sodium bicarbonate and brine. The organic layer was dried over anhydrous magnesium sulfate and concentrated in vacuo. The residue was recrystallized from boiling hexane/ethyl acetate to give 2.39 g of tert-butyl-(4R,5R)-4-(tert-butyldimethylsiloxy)-5-uracil-4,5-dihydro-2-furoate 20 (yield 78%).

¹H NMR (CDCl₃, 300 MHz) δ0.11 (s, 3), 0.13 (s, 3), 0.91 (s, 9), 1.55 (s, 9), 5.08 (app t, 1, J=2.9), 5.77 (dd, 1, J=8.1; 2.4), 5.93 (d, 1, J=2.7), 6.27 (d, 1, J=3.0), 7.04 (d, 1, J=8.1), 8.34 (bs, 1).

¹³C NMR (CD₃OD, 101 MHz) δ4.7, 18.0, 25.6, 28.0, 79.9, 83.5, 94.5, 103.5, 111.2, 139.5, 149.5, 151.2, 158.1, 162.9.

IR (KBr, cm⁻¹): 2956, 2932, 1700, 1638, 1460, 1373, 1258, 1128, 1077, 841, 780.

Tert-Butyl (2R,4R,5R)-4-(tert-butyldimethylsiloxy)-5-uracil-tetrahydro-2-furoate (Compound 21)

To a solution of tert-butyl (4R,5R)-4-(tert-butyldimethylsiloxy)-5-uracil-4,5-dihydro-2-furoate 20 (2.10 g, 5.12 mmol) in 100 mL methanol, purged for 10 minutes with a stream of nitrogen by cannula needle positioned at fs the bottom of the flask, was added 10% Pd/C (0.40 g). The resulting suspension was purged with nitrogen for an additional 10 minutes and then purged with hydrogen (1 atm) for 10 min. The resulting mixture was stirred under hydrogen (1 atm) for an additional 30 minutes and then again purged with nitrogen for 10 minutes. The Pd/C was removed by filtration through a pad of Celite and the filtrate was concentrated in vacuo to give a crude white solid composed of a 9/1 mixture of the desired product and its diastereomer at the 4'-center. The residue was recrystallized in boiling ethyl acetate/hexanes (the hexanes being added to turbidity) to give 1.80 g of pure tert-butyl (2R,4R,5R)-4-(tert-butyldimethylsiloxy)-5-uracil-tetrahydro-2-furoate 21 (yield 85%).

¹H NMR (CDCl₃, 400 MHz) δ0.09 (s, 3), 0.11 (s, 3), 0.89 (s, 9), 1.50 (s, 9), 2.21–2.27 (m, 1), 2.39–2.46 (m, 1), 4.55 (m, 1), 4.78 (dd, 1, J=8.8; 4.4), 5.71 (dd, 1, J=8.0; 2.4), 5.75, (d, 1, J=2.0), 7.21 (d, 1, J=8.0), 8.53 (bs, 1).

IR (KBr, cm⁻¹): 3150, 3048, 2955, 2860, 1750, 1687, 1624, 1458, 1377, 1255, 1166, 1111, 1079, 838, 810, 777.

1-[3'-Deoxy-2'-(tert-butyldimethylsiloxy)-α-L-arabinofuranosyl]uracil (Compound 22)

A solution of tert-butyl (2R,4R,5R)-4-(tert-butyldimethyl-siloxy)-5-uracil-tetrahydro-2-furoate 21 (1.80 g, 4.36 mmol) in 10 mL of 90% trifluoroacetic acid in dichloromethane was stirred at ambient temperature for 5–10 minutes and then concentrated in vacuo to a clear oil. The residue was co-evaporated from 1:1 dichloromethane/toluene and then from a mixture of 1:1 methanol/toluene. The product was used in the next step without further purification.

To a solution of the free carboxylic acid (47.0 mg, 0.131 mmol) described above in 5 mL of tetrahydrofuran is added at 0° C. ethyl chloroformate (49.7 mg, 43.8 μl, 0.459 mmol) followed by triethylamine (21.4 mg, 29.4 μL, 0.211 mmol). The resulting mixture was stirred at ambient temperature for 2 hours and then recooled to 0° C. In one portion, sodium borohydride (35 mg, 0.917 mmol) was added with rapid stirring followed by dropwise addition of water over 0.5 hour to dissolve the sodium borohydride. The resulting mixture was stirred at 0° C. for 1 hour and then concentrated in vacuo. The residue was partitioned between ethyl acetate and water. The layers were separated and the organic layer washed with 1N aqueous hydrochloric acid, saturated aqueous sodium bicarbonate and brine. The organic layer was dried over anhydrous magnesium sulfate, filtered and evaporated in vacuo. The residue was purified by silica gel chromatography (eluant: hexanes/ethyl acetate (1/1 to 3:1)) to give 44.8 mg of 1-[3'-deoxy-2'-(tert-butyldimethylsiloxy)-α-L-arabino]furanosyl]uracil 22 (yield 100%).

¹H NMR (CDCl₃, 300 MHz) δ0.14 (s, 3), 0.18 (s, 3), 0.91 (s, 9), 1.89 (ddd, 1, J=14.0; 3.6, 2.4), 2.19 (ddd, 1, J=14.1; 8.8, 5.4), 3.77–3.78 (m, 2), 4.56–4.58 (m, 1), 4.62–4.67 (m, 1), 5.60 (d, 1, J=1.2), 5.73 (d, 1, J=8.1), 7.27 (d, 1, J=8.1).

IR (neat, cm⁻¹): 3400, 3196, 2953, 2931, 2857, 1685(s), 1462, 1387, 1263, 1121, 837, 779.

1-[5'-O-(4-Toluenesulfonyl)-3'-deoxy-2'-(tert-butyldimethylsilyloxy)-α-L-arabinofuranosyl]uracil (Compound 23)

To a solution of 1-[3'-deoxy-2'-(tert-butyldimethylsiloxy)-α-L-arabinofuranosyl]uracil 22 (42.1 mg, 0.123 mmol) in 2 mL of pyridine was added at ambient temperature 4-toluenesulfonyl chloride (141 mg, 0.738 mmol). The resulting mixture was stirred at ambient temperature for 25 hours under nitrogen and then partitioned between 50 mL of ethyl acetate and 50 mL of water. The layers were separated and the organic layer was washed with 1N aqueous hydrochloric acid, saturated aqueous sodium bicarbonate and brine. The organic layer was dried over u anhydrous magnesium sulfate and concentrated in vacuo. The residue was purified by silica gel chromatograpy (eluant: ethyl acetate/hexanes (1/2 to 2/1)) to give 54.8 mg of 1-[5'-O-(4-toluenesulfonyl)-3'-deoxy-2'-(tert-butyldimethylsilyloxy)-α-L-arabinofuranosyl]uracil 23 (yield 90%).

¹H NMR (CDCl₃, 400 MHz) δ0.07 (s, 3), 0.11 (s, 3), 0.84 (s, 9), 1.85 (m, 1), 2.11–2.18 (m, 1), 2.46 (s, 3), 4.12 (dd, 1, J=10.4; 4.8), 4.23 (dd, 1, J=10.41; 6.8), 4.48–4.49 (m, 1), 4.68–4.74 (m, 1), 5.55 (s, 1), 5.70 (d, 1, J=7.6), 7.16 (d, 1, J=8.0), 7.36 (d, 2, J=8.0), 7.82 (d, 2, J=7.6), 8.18 (bs, 1).

1-[5'-Azido-3',5'-dideoxy-2'-(tert-butyldimethylsilyloxy)-α-L-arabinofuranosyl]uracil (Compound 24)

To a solution of 1-[5'-O-(4-toluensulfonyl)-3'-deoxy-2'-(tert-butyldimethylsilyloxy)-α-arabinofuranosyl]uracil 23 (46.8 mg, 0.0942 mmol) in 3 mL of dimethylformamide was added sodium azide (75 mg, 1.2 mmol) in one portion. The resulting mixture was heated at 90° C. for 5 minutes, stirred at 50° C. for 5 hours and then evaporated in vacuo. The residue was partioned between water and ethyl acetate. The layers were separated and the organic layer was washed with saturated aqueous sodium bicarbonate and brine. The organic layer was dried over anhydrous magnesium sulfate and concentrated in vacuo. The residue was purified by silica gel chromatography (eluant: hexanes/ethyl acetate 1/1) to give 29.5 mg of 1-[5'-azido-3',5'-dideoxy-2'-(tert-butyldimethylsilyloxy)-α-L-arabinofuranosyl]uracil 24 (yield 85%).

¹H NMR (400 MHz, CD₃OD): δ0.12 (s, 3), 0.17 (s, 3), 0.91 (s, 9), 1.87 (ddd, 1, J=13.6; 3.6, 3.2), 2.16–2.23 (m, 1H), 3.38 (dd, 1, J=12.8; 4.4), 3.64 (dd, 1, J=12.8; 7.2), 4.56–4.58 (m, 1), 4.59–4.65 (m, 1), 5.68 (s, 1), 5.73 (d, 1, J=8.0), 7.23 (d, 1, J=8.0), 8.78 (bs, 1)

1-[5'-Amino-3',5'-dideoxy-α-L-arabinofuranosyl]uracil (Compound 25)

To a solution of 1-[5'-azido-3',5'-dideoxy-2'-(tert-butyldimethylsilyloxy)-α-L-arabinofuranosyl]uracil 24 (29.5 mg, 0.080 mmol) in 5 mL of tetrahydrofuran was added tetrabutyl-ammonium fluoride (1M in tetrahydrofuran, 0.0964 mmol, 96 μL). The resulting mixture was stirred at ambient temperature for 1 hour and then evaporated in vacuo. The residue was purified by silica gel chromatography (eluant: ethyl acetate) to give 16.9 mg of 1-[5'-amino-3',5'-dideoxy-α-L-arabinofuranosyl]uracil 25 (yield 83%).

$^1$H NMR (400 MHz, CD$_3$OD): δ1.88 (ddd, 1, J=13.2; 6.2, 5.0), 2.30–2.37 (m, 1), 3.40 (dd, 1, J=13.2; 4.0), 3.51 (dd, 1, J=13.2; 6.8), 4.48–4.51 (m, 1), 4.62–4.65 (m, 1), 5.68 (d, 1, J=8.0), 5.76 (d, 1, J=3.2), 7.58 (d, 1, J=8.0).

$^{13}$C NMR (CD$_3$OD, 101 MHz) δ36.1, 56.0, 76.3, 81.6, 95.1, 102.6, 142.5, 152.3, 166.3.

1-[5'-Amino-3',5'-dideoxy-α-L-arabinofuranosyl] uracil (Compound 26)

To a solution of 1-[5'-amino-3',5'-dideoxy-α-L-arabinofuranosyl]uracil 25 (16.0 mg. 0.0667 mmol) in 50 μL methanol was added 1 mL 1,3-propanedithiol. The resulting mixture was stirred at ambient temperature for 4 days and then concentrated in vacuo. The residue was partitioned between water and dichloromethane. The layers were separated and the aqueous layer was washed with dichloromethane. The aqueous layer was then lyophilized to give 9.0 mg of 1-[5'-amino-3',5'-dideoxy-α-L-arabinofuranosyl] uracil 26 (yield 60%).

$^1$H NMR (400 MHz, CD$_3$OD): δ1.8 (ddd, 1, J=13.8; 4.8; 3.8), 2.33 (ddd, 1, J=13.8; 8.4; 6.2), 2.81 (dd, 1, J=13.2, 6.0), 2.90 (dd, 1, J=13.2; 3.6), 4.41 (ddd, 1, J=6.0; 3.6; 2.0), 4.54–4.59 (m, 1), 5.68 (d, 1, J=8), 5.74 (d, 1, J=2.0), 7.55 (d, 1, J=8.4).

$^{13}$C NMR (CD$_3$OD, 101 MHz) δ36.2, 46.3, 76.5, 83.8, 95.7, 102.4, 142.2, 152.4, 166.6.

IR (KBr, cm$^{-1}$): 3174, 1688, 1630, 1503, 1458, 1265, 1100, 815.

General Procedure for the Synthesis of UPAs: Synthesis of Compound 34

(2s,3s)-N$^2$-[(tert-Butoxy)carbonyl]-N$^3$-[N-[fluoren-9-ylmethoxycarbonyl]-L-alanyl]-N$^3$-methyldiaminobutyramide (Compound 30)

A solution of 9-fluorenylmethyloxycarbonyl-L-alanine pentafluorophenyl ester (0.48 g, 1.03 mmol) and of (2S,3S)-3-methylamino-2-(tert-butoxyformamido)butyric acid 10 (0.2 g, 0.861 mmol) in 10 mL of dimethylformamide was stirred at 50–55° C. for 14 hours. The reaction mixture was then evaporated in vacuo and the residue purified by flash-chromatography on silica gel (eluant: ethyl acetate/dichloromethane/methanol/acetic acid (1/0/0/0 to 1/1/0/0 to 6/4/0.1/01) to give 0.344 g of 30 (yield 77%).

$^1$H NMR (300 MHz, CD$_3$OD) δ1.31 (d, 3, J=6.9), 1.39 (d, 3, J=6. 9), 1.55 (s, 9), 3.12 (s, 3), 4.0–4.70 (m, 5), 5.02 (m, 1), 7.3–7.6 (m, 4), 7.75 (m, 2), 7.89 (m, 2).

IR (KBr pellet, cm$^{-1}$): 3600–2500, 1716, 1502, 1422, 1265, 1162, 896, 748.

Mass calculated for C$_{28}$H$_{35}$N$_3$O$_7$: 525.25; mass found for (M−H): 524.3. Any other dipeptide combinations are prepared and purified in the same way from the corresponding Fmoc-protected amino acid and (2S,3S)-3-methylamino-2-(tert-butoxyformamido)butyric acid 10.

1-[5'-(2S,3S)-N$^2$-[(tert-Butoxy)carbonyl]-N$^3$-[N-[fluoren-9-ylmethoxycarbonyl]-L-alanyl]-N$^3$-methyl-diaminobutyramido]-3',5'-dideoxy-α-L-arabinofuranosyl]uracil (Compound 31)

At 0° C., a solution of pentafluorophenol (0.0087 g, 0.0472 mmol) in 0.25 mL of ethyl acetate was added to a solution of (2S,3S)-N$^2$-[(tert-butoxy)carbonyl]-N$^3$-[N-[fluoren-9-ylmethoxyl-carbonyl]-L-alanyl]-N$^3$-methyl-diaminobutyramide 30 (0.025 g, 0.0476 mmol) in 0.25 mL ethyl acetate followed by dicyclohexylcarbodiimide (0.0098 g, 0.0475 mmol). The resulting mixture was stirred at 0° C. for 1 hour and then for 0.5 hour at ambient temperature. The reaction mixture was re-cooled to 0° C. and filtered through cotton (rinsed once with 2 mL of cold ethyl acetate). The filtrate was evaporated in vacuo and the residue was taken up in 0.25 mL of dimethylformamide to which 1-[5'-amino-3', 5'-dideoxy-α-L-arabinofuranosyl]uracil 26 (0.009 g, 0.0396 mmol) is added. The resulting mixture was stirred at 50–55° C. for 16 hours. The reaction mixture was then evaporated and the residue purified by flash-chromatography on silica gel (eluant: dichloromethane/ethyl acetate/methanol (1/0/0 to 6/4/0 to 6/4/0.1 to 6/4/0.2 to 6/4/0.3 to 6/4/0.4 to 6/4/0.5 to 6/4/0.6 to 6/4/0.7) to give 0.0132 mg of 31 (yield 45%).

IR (KBr pellet, cm$^{-1}$): 3500–2600, 1711, 1682, 1625, 1421, 1265, 1165, 896, 741.

Any other nucleosyl dipeptide combinations may be prepared and purified in the same manner from the corresponding pentafluorophenol ester-activated dipeptide and 1-[5'-amino-3'5'-dideoxy-β-D-ribofuranosyl]uracil 18 or 1-[5'-amino-3',5'-dideoxy-α-L-arabinofuranosyl]uracil 26.

1-[5'-((2S,3S)-N$^2$-(N-((1S)-1-(tert-Butoxycarbonyl)-2-indol-3-ylethyl)carbamoyl)-L-alanyl)-N$^3$-(N-((fluoren-9-ylmethoxy)-carbonyl)-L-alanyl)-N$^3$-methyl-2,3-diaminobutyramido)-3',5'-dideoxy-α-L-arabinofuranosyl]uracil (Compound 32)

A solution of 1-[5-(2S,3S)-N$^2$-[(tert-butoxy)carbonyl]-N$^3$-[N-[fluoren-9-ylmethoxylcarbonyl]-L-alanyl]-N$^3$-methyl-diaminobutyramido]-3,5,dideoxy-α-L-arabinofuranosyl]uracil 31 (0.0132 g, 0.018 mmol) in 1 mL of trifluoroacetic acid/water (9/1) was stirred at ambient temperature for 1 hour. The reaction mixture, diluted with 2 mL of methanol and 2 mL of toluene, was evaporated in vacuo and then co-evaporated with 2 mL of toluene. The residue was dissolved in 0.25 mL of a di-isopropylethylamine solution in dimethylformamide prepared by diluting 28 μL di-isopropylethylamine in 2 mL dimethylformamide. N-[[(1S)-1-L-(pentafluorophenoxy)) carbonyl]ethyl]carbamoyl]-L-tryptophane, tert-butyl ester 29 (0.020 g, 0.0369 mmol) was added and the resulting mixture was stirred at 50–55° C. for 14 hours. The reaction mixture was evaporated in vacuo and the residue was purified by flash-chromatography on silica gel (eluant:dichloromethane/ethyl acetate/methanol/acetic acid (1/0/0/0 to 6/4/0/0 to 6/4/0.5/0.1 to 6/4/0.75/0.1 to 6/4/1/0.1) to give 0.0175 g of 1-[5-((2S,3S)-N$^2$-(N-((1S)-1-(tert-butoxycarbonyl)-2-indol-3-ylethyl)carbamoyl)-L-alanyl)-N$^3$-(N-((fluoren-9-ylmethoxy)carbonyl)-L-alanyl)-N$^3$-methyl-2,3-diaminobutyramido)-3,5-dideoxy-α-L-arabinofuranosyl]uracil 32 (yield>95%). Mass calculated for C$_{51}$H$_{61}$N$_9$O$_{12}$: 991.44; mass found for (M+H)$^+$: 992.5, (M+Na)$^+$: 1014.5.

IR (KBr pellet, cm$^{-1}$): 3600–2900, 1676, 1685, 1544, 1456, 1261, 1206, 1153, 1102, 743.

1-[5'-[(2S,3S)-N$^2$-[N-[[(1S)-1-Carboxy-2-indol-3-ylethyl]carbomoyl]-L-alanyl]-N$^3$-L-alanyl-N$^3$-methyl-2,3-diaminobutyramidol-3',5'-dideoxy-α-L-arabinofuranosyl]uracil (Compound 34)

A solution of 1-[5-[[(2S,3S)-N$^2$-[N-[[(1S)-1-(tert-butoxycarbonyl)-2-indol-3-ylethyl]carbamoyl]-L-alanyl]-N$^3$-[N-[(fluoren-9-ylmethoxylcarbonyl)-L-alanyl]-N$^3$- methyl-2,3-diaminobutyramido]-3,5-dideoxy-α-L-arabinofuranosyl]uracil 32 (0.0175 g, 0.018 mmol) in 1 mL of trifluoroacetic acid/water/ethanedithiol(9/1/0.1) was stirred at ambient temperature for 2.5 hours. The reaction mixture, diluted with 2 mL methanol and 2 mL toluene, was evaporated in vacuo and then co-evaporated with 2 mL toluene. The residue was used directly in the next step without further purification.

Mass calculated for $C_{47}H_{53}N_9O_{12}$: 935.38; mass found for (M–H)⁻: 934.8.

A solution of the above residue (0.018 mmol, theor.) in 2 mL diethylamine/acetonitrile/dichloromethane/water (50/23/23/4) was stirred at ambient temperature for 2 hours. The precipitate was removed by filtration and rinsed once with 2 mL dichloromethane. The solid was re-dissolved in 5 mL methanol/water 1/1 and the solution was evaporated in vacuo. The residue was then taken up in 1 mL water and filtered through a nylon filter. The filter was rinsed once with 1 mL of water and the filtrates combined and evaporated in vacuo. The residue, taken up in 1 mL water was filtered through a $C_{18}$ Analtech Spice Sample Preparation Cartridge. The cartridge was rinsed twice with 1 mL water and twice with 1 mL acetonitrile/water (1/1). The filtrate was evaporated in vacuo and the residue, taken up in 1 mL water, was filtered through a nylon filter. The filter was rinsed twice with 2 mL of water. Compound 34 was purified by HPLC on a semi-preparative $C_{18}$ column (eluant: acetonitrile/0.1% trifluoroacetic acid in water (0/100 to 70/30) in 20 minutes, 10 mL/minute, detection 260 nm, injections of 0.5 mL of the filtrate). The combined pure fractions were evaporated in vacuo and the residue, taken up in 1 mL water was filtered through a Rainin Nylon Filter unit(0.3 U/13 mm). The filter was rinsed twice with 1 mL of water and the filtrate was lyophilized to afford 0.0046 g of 1-[5-((2S,3S)-$N^2$-(2-indol-3-ylethyl)carbamoyl)-L-alanyl)-$N^3$-L-alanyl)-$N^3$-methyl-2,3-diaminobutyramido)-3,5-dideoxy-α-L-arabinofuranosyl]uracil 34 (yield 36% over 4 steps).

Mass calculated for $C_{32}H_{43}N_9O_{10}$ 713.31; mass found for (M+H)⁺714.4.

IR (KBr pellet, cm⁻¹): 3600–2500, 2363, 1685, 1655, 1560, 544, 1204.

Any other deprotected UPA combinations may be prepared and purified in the same manner using the corresponding protected nucleosyl tetrapeptide.

N-[[(1S)-1-[(Benzyloxy)carbonyl]ethyl]carbamoyl]-L-tryptophane, tert-butyl Ester (Compound 27)

(Majer, et al., J. Org. Chem., 1994, 59:1937–38).

A solution of L-alanyl benzyl ester 4-toluenesulfonic acid salt (2.0 9, 5.89 mmol) and diisopropylethylamine (1.12 mL, 6.45 mmol) in 20 mL of dichloromethane was added dropwise, at ambient temperature, to a solution of triphosgene (0.582 9, 1.96 mmol) in 100 mL dichloromethane. The resulting mixture was stirred at ambient temperature for 5 minutes at which time a solution of L-tryptophane tert-butyl ester, hydrochloride salt (1.75 g, 5.89 mmol) and diisopropylethylamine (1.12 mL, 6.45 mmol) in 10 mL of dichloromethane was added. The resulting mixture was stirred at ambient temperature for 30 minutes and then washed sequentially with 1M hydrochloric acid, 10% anhydrous sodium bicarbonate and brine. The combined organic layers were dried over anhydrous sodium sulfate, filtered and evaporated in vacuo. The residue is purified by flash-chromatography on silica gel (eluant: hexanes/ethyl acetate (8/2 to 6/4)) to afford 2.41 g of N-[[(1S)-1-[(benzyloxy) carbonyl]ethyl]carbamoyl]-L-tryptophane, tert-butyl ester 27 (yield 88%).

¹³C NMR (CDCl₃, 101 MHz) δ175.00, 172.08, 156.93, 135.85, 135.30, 128.46, 128.42, 128.18, 128.05, 127.64, 123.39, 121.70, 119.03, 118.76, 111.21, 109.65, 81.81, 67.10, 53.80, 48.52, 27.88, 18.82.

Mass calculated for $C_{26}H_{31}N_3O_5$: 462.23; mass found for (M+Na)⁺:488.2.

Any other protected urea combinations may be prepared and purified in the same manner using the corresponding protected amino acids.

N-[(1S)-1-Carboxyethyl]carbamoyl]-L-tryptophane, Tert-butyl Ester (Compound 28)

A solution of N-[[(1S)-1-(benzyloxy)carbonyl]ethyl]-carbamoyl]-L-tryptophane, tert-butyl ester 27 (2.4 g, 5.15 mmol) in 10 mL methanol (+10 mL methanol to rinse) was added under nitrogen to a suspension of 10% palladium on charcoal (0.24 g, 20 wt. %) in 20 mL methanol. The flask was then flushed with hydrogen (1 atm) and the mixture was vigorously stirred at ambient temperature under hydrogen (1 atm) for 5 hours. The catalyst was removed by filtration and rinsed with methanol. The filtrate was evaporated in vacuo and the residue was purified by flash-chromatography on silica gel(eluant: hexanes/ethyl acetate/acetic acid (1/1/0.01 to 1/2/0.01)) to give 1.5 g of N-[[(1S)-1-carboxyethyl]carbamoyl]-L-tryptophane, tert-butyl ester 28 (yield 78%).

¹H NMR (CDCl₃, 400 MHz) δ8.70 (s, 1), 7.53 (d, 1, J=7.2), 7.30–7.15 (m, 3), 7.11 (t, 1, J=7.2), 7.05 (t, 1, J=7.2), 6.89 (d, 1, J=2), 5.87 (d, 1, J=7.6), 5.71 (bs, 1), 4.67 (bd, 1, J=6.4), 4.30 (bt, 1, J=6), 3.16 (m, 2), 1.38 (s, 9), 1.20 (d, 3, J=7.2).

¹³C NMR (CDCl₃, 101 MHz) δ177.12, 173.18, 158.24, 136.28, 129.24, 128.44, 127.70, 125.51, 123.81, 122.01, 119.34, 118.83, 111.57, 82.83, 54.38, 49.16, 28.13, 17.92.

IR (KBr pellet, cm⁻¹): 3600–2400, 1723, 1639, 1561, 1458, 1155, 743.

Mass calculated for $C_{19}H_{25}N_3O_5$: 375.18; mass found for (M–H)⁻: 373.6, (2M–H)⁻: 749.7.

Any other urea combinations may be prepared and purified in the same manner using the corresponding protected ureas.

N-[(1S)-1-[(Pentafluorophenoxy))carbonyl]ethyl]carbamoyl]-L-tryptophane, Tert-butyl Ester (Compound 29)

At 0° C., a solution of pentafluorophenol (0.4 g, 2.17 mmol) in 2 mL ethyl acetate was added to a solution of N-[[(1S)-1-carboxyethyl]carbamoyl]-L-tryptophane, tert-butyl ester 28 (0.75 g, 2 mmol) in 20 mL of ethyl acetate, followed by dicyclohexylcarbodiimide (0.45 g, 2.18 mmol). The resulting mixture was stirred at 0° C. for 1 hour and then for 0.5 hour at ambient temperature. The reaction mixture was re-cooled to 0° C. and filtered through cotton (which was rinsed once with 2 mL of cold ethyl acetate). The filtrate and rinse were combined and evaporated in vacuo and to give 0.85 g (yield 92%) of N-[[(1S)-1-[(pentafluorophenoxy))carbonyl]ethyl]carbamoyl]-L-tryptophane, tert-butyl ester 29.

Any other pentafluorophenol-ester-activated urea combinations may be prepared and purified in the same manner using the corresponding ureas.

The following compounds were prepared in the same way as compound 34 using the starting materials indicated. The structures of the ureas PFP-O-AA₁-NHCONH-AA₂-(O-t-Bu) are abbreviated as AA₁/AA₂ ureas.

1-[5'-[(2S,3S)-$N^2$-[N-[[(1S)-1-Carboxy-4-hydroxyphenethyl]carbamoyl]-L-phenylalanyl]-$N^3$-L-phenylalanyl-$N^3$-methyl-2,3-diaminobutyramido]-3',5'-dideoxy-α-L-arabinofuranosyl]uracil (Compound 100)

Compound 100 was prepared using Fmoc-L-phenylalanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tyrosine urea.

Mass calculated for $C_{42}H_{50}N_8O_{11}$: 842.36; mass found $(M+H)^+$: 843.4.

1-[5'-[(2S,3S)-$N^2$-[N-[[(1S)-1-Carboxy-4-hydroxyphenethyl]carbamoyl]-L-phenylalanyl]-$N^3$-L-leucyl-$N^3$-methyl-2,3-diaminobutyramido]-3',5'-dideoxy-α-L-arabinofuranosyl]uracil (Compound 101)

Compound 101 was prepared using Fmoc-L-leucine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tyrosine urea.

Mass calculated for $C_{39}H_{52}N_8O_{11}$: 808.37; mass found $(M+H)^+$: 809.5.

1-[5'-[(2S,3S)-$N^2$-[N-[[(1S)-1-Carboxy-4-hydroxyphenethyl]carbamoyl]-L-phenylalanyl]-$N^3$-glycyl-$N^3$-methyl-2,3-diaminobutyramido]-3',5'-dideoxy-α-L-arabinofuranosyl]uracil (Compound 102)

Compound 102 was prepared using Fmoc-glycine, (2S,3s)-3-methylamino-2-(tert-butoxyformamido)butyric acid 10, 1-[5'-amino-3',5'-dideoxy-α-L-arabinofuranosyl]uracil 26 and L-phenylalanine/L-tyrosine urea.

Mass calculated for $C_{35}H_{44}N_8O_{11}$: 752.31; mass found $(M+H)^+$: 753.4.

1-[5'-[(2S,3S)-$N^2$-[N-[[(1S)-1-Carboxy-2-indol-3-ylethyl]carbamoyl]-L-alanyl]-$N^3$-L-3-hydroxyphenylalanyl-$N^3$-methyl-2,3-diaminobutyramidol-3',5'-dideoxy-α-L-arabinofuranosyl]uracil (Compound 103)

Compound 103 was prepared using Fmoc-L-3-hydroxyphenylalanine, (2S,3S)-3-methylamino-2-(tert-butoxyformamido)butyric acid 10, 1-[5'-amino-3',5'-dideoxy-α-L-arabinofuranosyl]uracil 26 and N-[(1S)-1-((pentafluorophenoxy))-carbonyl]ethyl]carbamoyl]-L-tryptophane, tert-butyl ester 29.

Mass calculated for $C_{37}H_{45}N_9O_{11}$: 791.33; mass found $(M+H)^+$: 792.4.

1-[5'[(2S,3S)-$N^2$-(N-[[(1S)-1-Carboxy-4-hydroxyphenethyl]carbamoyl]-L-methionyl]-$N^3$-glycyl-$N^3$-methyl-2,3-diaminobutyramidol-3',5'-dideoxy-α-L-arabinofuranosyl]uracil (Compound 104)

Compound 104 was prepared using Fmoc-glycine, (2S,3S)-3-methylamino-2-(tert-butoxyformamido)butyric acid 10, 1-[5'-amino-3',5-dideoxy-α-L-arabinofuranosyl]uracil 26 and L-methionine/L-tyrosine urea.

Mass calculated for $C_{31}H_{44}N_8O_{11}S$: 736.28; mass found $(M+H)^+$: 737.4.

1-[5'[(2S,3S)-$N^2$-[N-[[(1S)-1-Carboxy-4-hydroxyphenethyl]carbamoyl]-L-4-fluorophenylalanyl]-$N^3$-L-4-fluorophenylalanyl-$N^3$-methyl-2,3-diaminobutyramido]-3',5'-dideoxy-α-L-arabinofuranosyl]uracil (Compound 105)

Compound 105 was prepared using Fmoc-L-4-fluorophenylalanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{42}H_{48}F_2N_8O_{11}$: 878.89; mass found $(M+H)^+$: 879.9.

1-[5'[(2S,3S)-$N^2$-[N-[[(1S)-1-Carboxy-4-hydroxyphenethyl]carbamoyl]-L-4-fluorophenylalanyl)-$N^3$-L-phenylalanyl-$N^3$-methyl-2,3-diaminobutyramido]-3',5'-dideoxy-β-L-arabinofuranosyl]uracil (Compound 106)

Compound 106 was prepared using Fmoc-L-phenylalanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{41}H_{47}FN_8O_{11}$: 846.33; mass found $(M+H)^+$: 847.9.

1-[5'[(2S,3S)-$N^2$-[N-[[(1S)-1-Carboxy-4-hydroxyphenethyl]carbamoyl]-L-4-fluorophenylalanyl]-$N^3$-L-leucyl-$N^3$-methyl-2,3-diaminobutyramido]-3',5'-dideoxy-α-L-arabinofuranosyl]uracil (Compound 107)

Compound 107 was prepared using Fmoc-L-leucine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{39}H_{51}FN_8O_{11}$: 826.37; mass found $(M+H)^+$: 827.5.

1-[5'[(2S,3S)-$N^2$-[N-[[(1S)-1-Carboxy-2-indol-3-ylethyl]carbamoyl]-L-leucyl]-$N^3$-L-leucyl-$N^3$-methyl-2,3-diaminobutyramido]-3',5'-dideoxy-α-L-arabinofuranosyl]uracil (Compound 108)

Compound 108 was prepared using Fmoc-leucine, (2S,3S)-3methylamino-2-(tert-butoxyformamido)-butyric acid 10, 1-[51-amino-3',5'-dideoxy-α-L-arabinofuranosyl]uracil 26 and L-leucine/L-tryptophane urea.

Mass calculated for $C_{38}H_{55}N_9O_{10}$: 797.41; mass found $(M+H)^+$: 798.5.

1-[5'-[(2S,3S)-$N^2$-[N-[[(1S)-1-Carboxy-2-indol-3-ylethyl]carbamoyl]-L-leucyl]-$N^3$-glycyl-$N^3$-methyl-2,3-diaminobutyramidol-3',5'-dideoxy-α-L-arabinofuranosyl]uracil (Compound 109)

Compound 109 was prepared using Fmoc-glycine, (2S,3S)-3-methylamino-2-(tert-butoxyformamido)butyric acid 10, 1-[5'-amino-3',5'-dideoxy-α-L-arabinofuranosyl]uracil 26 and L-leucine/L-tryptophane urea.

Mass calculated for $C_{34}H_{47}N_9O_{10}$: 741.34; mass found $(M+H)^+$: 742.5.

1-[5'-[(2S,3S)-$N^2$-[N-[[(1S)-1-Carboxy-2-indol-3-ylethyl]carbamoyl]-L-methionyl]-$N^3$-L-4-fluorophenylalanyl-$N^3$-methyl-2,3-diaminobutyramido]-3',5'-dideoxy-α-L-arabinofuranosyl]uracil (Compound 110)

Compound 110 was prepared using Fmoc-L-4-fluorophenylalanine, (2S,3S)-3-methylamino-2-(tert-butoxyformamido)butyric acid 10, 1-[5'-amino-3',5'-dideoxy-α-L-arabinofuranosyl]uracil 26 and L-methionine/L-tryptophane urea.

Mass calculated for $C_{40}H_{50}N_9O_{10}FS$: 867.33; mass found $(M-H)^-$: 866.4.

1-[5'-[(2S,3S)-N²-[N-([(1S)-1-Carboxy-2-indol-3-ylethyl]carbamoyl]-L-methionyl]-N³-L-phenylalanyl-N³-methyl-2,3-diaminobutyramido]-3',5'-dideoxy-α-L-arabinofuranosyl]uracil (Compound 111)

Compound 111 was prepared using Fmoc-L-phenylalanine, (2S,3S)-3-methylamino-2-(tert-butoxyformamido)butyric acid 10, 1-[5'-amino-3',5'-dideoxy-α-Larabinofuranosyl]uracil 26 and L-methionine/L-tryptophane urea.

Mass calculated for $C_{40}H_{51}N_9O_{10}S$: 849.35; mass found (M−H)⁻: 848.1.

1-[5'-[(2S,3S)-N²-[N-[[(1S)-1-Carboxy-2-indol-3-ylethyl]carbamoyl]-L-methionyl]-N³-glycyl-N³-methyl-2,3-diaminobutyramido]-3',5'-dideoxy-α-L-arabinofuranosyl]uracil (compound 112)

Compound 112 was prepared using Fmoc-glycine, (2S,3S)-3-methylamino-2-(tert-butoxyformamido)butyric acid 10, 1-[5'-amino-3',5'-dideoxy-α-L-arabinofuranosyl]uracil 26 and L-methionine/L-tryptophane urea.

Mass calculated for $C_{33}H_{45}N_9O_{10}S$: 759.30; mass found (M−H)⁻: 758.4.

1-[5'-[(2S,3S)-[N-[[(1S)-1-Carboxy-2-indol-3-ylethyl]carbamoyl]-L-4-fluorophenylalanyl]-N³-L-phenylalanyl-N³-methyl-2,3-diaminobutyramido]-3',5'-dideoxy-α-L-arabinofuranosyl]uracil (Compound 113)

Compound 113 was prepared using Fmoc-L-phenylalanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tryptophane urea.

Mass calculated for $C_{44}H_{50}FN_9O_{10}$: 883.37; mass found (M−H)⁻: 882.4.

1-[5'-((2S,3S)-N²-[N-[[(1S)-1-Carboxy-2-indol-3-ylethyl]carbamoyl]-L-phenylalanyl]-N³-L-4-fluorophenylalanyl-N³-methyl-2,3-diaminobutyramidol-3',5'-dideoxy-α-L-arabinofuranosyl]uracil (Compound 114)

Compound 114 was prepared using Fmoc-L-4-fluorophenylalanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tryptophane urea.

Mass calculated for $C_{44}H_{50}FN_9O_{10}$: 883.37; mass found: no molecular peak observed.

1-[5'[(2S,3S)-N³-L-Alanyl-N²-[N-[[(1S)-1-carboxy-4-hydroxyphenethyl)-carbamoyl]-L-methionyl]-N³-methyl-2,3-diaminobutyramido]-3',5'-dideoxy-α-L-arabinofuranosyl]uracil (Compound 115)

Compound 115 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-methionine/L-tyrosine urea.

Mass calculated for $C_{32}H_{46}N_8O_{11}S$: 750.30; mass found (M+H)⁺: 751.4.

1-[5'-[(2S,3S)-N²-[N-[[(1S)-1-Carboxy-2-indol-3-ylethyl)carbamoyl]-L-4-fluorophenylalanyl]-N³-glycyl-N³-methyl-3-diaminobutyramido]-3',5'-dideoxy-α-L-arabinofuranosyl]uracil (Compound 116)

Compound 116 was prepared using Fmoc-glycine, (2S,3S)-3-methylamino-2-(tert-butoxyformamido)butyric acid 10, 1-[5'-amino-3',5'-dideoxy-(-L-arabinofuranosyl]uracil 26 and L-4-fluorophenylalanine/L-tryptophane urea.

Mass calculated for $C_{37}H_{44}FN_9O_{10}$: 793.32; mass found (M−H)⁻: 792.0.

1-[5'-[(2S,3S)-N²-[N-[[(1S)-1-Carboxy-2-indol-3-ylethyl]carbamoyl]-L-4-fluorophenylalanyl]-N³-L-leucyl-N³-methyl-2,3-diaminobutyramido]-3',5'-dideoxy-α-L-arabinofuranosyl]uracil (Compound 117)

Compound 117 was prepared using Fmoc-L-leucine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tryptophane urea.

Mass calculated for $C_{41}H_{52}FN_9O_{10}$: 849.38; mass found (M−H)⁻: 848.2.

1-[5'-(2S,3S)-N²-[N-[[(1S)-1-Carboxy-2-indol-3-ylethyl]carbamoyl]-L-4-fluorophenylalanyl]-N³-L-4-fluorophenylalanyl-N³-methyl-2,3-diaminobutyramido]-3',5'-dideoxy-α-L-arabinofuranosyl]uracil (Compound 118)

Compound 118 was prepared using Fmoc-L-4-fluorophenylalanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tryptophane urea.

Mass calculated for $C_{44}H_{49}F_2N_9O_{10}$: 901.36; mass found (M+H)⁺: 902.0.

1-[5-[(2S,3S)-N³-L-Alanyl-N²-[N-[[(1S)-1-carboxy-4-hydroxyphenethyl]carbamoyl]-L-3-(2-thienyl)alanyl]-N³-methyl-2,3-diaminobutyramido]-3',5'-dideoxy-α-L-arabinofuranosyl]uracil (Compound 119)

Compound 119 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-3-(2-thienyl)alanine/L-tyrosine urea as the starting materials.

Mass calculated for $C_{34}H_{44}N_8O_{11}S$: 772.28; mass found (M+H)⁺: 773.6.

1-[5'-[(2S,3S)-N²-[N-[[(1S)-1-Carboxy-4-hydroxyphenethyl]carbamoyl]-L-leucyl)-N³-glycyl-N³-methyl-2,3-diaminobutyramidol-3',5'-dideoxy-α-L-arabinofuranosyl]uracil (Compound 120)

Compound 120 was prepared using Fmoc-glycine. (2S,3S)-3-methylamino-2-(tert-butoxyformamido)butyric acid 10, 1-[5'-amino-3',5'-dideoxy-α-L-arabinofuranosyl]uracil 26 and L-leucine/L-tyrosine urea.

Mass calculated for $C_{32}H_{46}N_8O_{11}$: 718.33; mass found (M+H)⁺: 719.4.

1-[5'1-[(2S,3S)-N²-[N-[[(1S)-1-Carboxy-2-indol-3-ylethyl)carbamoyl]-L-alanyl]-N³-glycyl-N³-methyl-2,3-diaminobutyramido]-3',5'-dideoxy-α-L-arabinofuranosyl]uracil (Compound 121)

Compound 121 was prepared using Fmoc-glycine, (2S,3S)-3-methylamino-2-(tert-butoxyformamido)butyric acid 10, 1-[5'-amino-3',5'-dideoxy-α-L-arabinofuranosyl]uracil 26 and L-alanine/L-tryptophane urea.

Mass calculated for $C_{31}H_{41}N_9O_{10}$: 699.30; mass found (M−H)⁻: 698.4.

1-[5'-[[(2S,3S)-N³-L-Alanyl-N²-[N-[[(1S)-1-carboxy-phenethyl]carbamoyl]-L-phenylalanyl]-N³-methyl-2,3-diaminobutyramido]-3',5'-dideoxy-α-L-arabinofuranosyl]uracil (Compound 122)

Compound 122 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-phenylalanine urea.

Mass calculated for $C_{36}H_{46}N_8O_{10}$: 750.33; mass found (M+H)⁺: 751.4.

1-[5'-[(2S,3S)-N³-(5-Aminopentanoyl)-N²-[N-[[(1S)-1-carboxy-2-indol-3-ylethyl]carbamoyl]-L-phenylalanyl]-N³-methyl-2,3-diaminobutyramido]-3',5'-dideoxy-α-L-arabinofuranosyl]uracil (Compound 123)

Compound 123 was prepared using Fmoc-5-aminopentanoic acid, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tryptophane urea.

Mass calculated for $C_{40}H_{51}N_9O_{10}$: 817.37; mass found (M+H)⁺: 818.7.

1-[5'-[(2S,3S)-N³-(5-Aminopentanoyl)-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 124)

Compound 124 was prepared using Fmoc-5-aminopentanoic acid, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{38}H_{49}FN_8O_{11}$: 812.35; mass found (M+H)⁺: 813.6.

1-[5'-[(2S,3S)-N³-L-Alanyl-N²-[N-[[(1S)-1-carboxy-2-(2-thienyl) ethyl]carbamoyl]-L-phenylalanyl]-N³-methyl-2,3-diaminobutyramido]-3',5'-dideoxy-α-L-arabinofuranosyl]uracil (Compound 125)

Compound 125 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-3-(2-thienyl)alanine urea.

Mass calculated for $C_{34}H_{44}N_8O_{10}S$: 756.29; mass found (M+H)⁺: 757.5.

1-[5'-[(2S,3S)-N³-L-Alanyl-N²-[N-[[(1S)-1-carboxy-4-hydroxyphenethyl]carbamoyl]-L-4-nitrophenylalanyl]-N³-methyl-2,3-diaminobutyramido]-3',5'-dideoxy-α-L-arabinofuranosyl]uracil (Compound 126)

Compound 126 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-4-nitrophenylalanine/L-tyrosine urea.

Mass calculated for $C_{36}H_{45}N_9O_{13}$: 811.33; mass found (M+H)⁺: 812.4.

1-[5'-[(2S,3S)-N²-[N-[[(1S)-1-carboxy-4-hydroxyphenethyl)carbamoyl]-L-4-fluorophenylalanyl]-N³-methyl-2,3-diaminobutyramido]-3',5'-dideoxy-α-L-arabinofuranosyl]uracil (Compound 127)

Compound 127 was prepared using (2S,3S)-3-methyl-3-allyloxycarbonyl-amino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{33}H_{40}FN_7O_{10}$: 713.28; mass found (M+H)⁺: 714.4.

1-[5'-[(2S,3S)-N²-[N-[[(1S)-1-Carboxy-2-indol-3-ylethyl]carbamoyl]-L-phenylalanyl]-N³-glycyl-N³-methyl-2,3-diaminobutyramido]-3',5'-dideoxy-α-L-arabinofuranosyl]uracil (Compound 128)

Compound 128 was prepared using Fmoc-glycine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tryptophane urea.

Mass calculated for $C_{37}H_{45}N_9O_{10}$: 775.33; mass found (M+H)⁺: 776.4.

1-[5'-[(2S,3S)-N²-[N-[[(1S)-1-Carboxy-4-hydroxyphenethyl)-L-4-fluorophenylalanyl]-N³-glycyl-N³-methyl-2,3-diaminobutyramido]-3',5'-dideoxy-α-L-arabinofuranosyl]uracil (Compound 129)

Compound 129 was prepared using Fmoc-glycine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{35}H_{43}FN_8O_{11}$: 770.30; mass found (M+H)⁺: 771.4.

1-[5'-[(2S,3S)-N³-L-Alanyl-N²-[N-[[(1S)-1-carboxy-4-hydroxyphenethyl]carbamoyl]-L-benzothienylalanyl]-N³-methyl-2,3-diaminobutyramidol-3',5'-dideoxy-α-L-arabinofuranosyl]uracil (Compound 130)

Compound 130 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-benzothienylalanine/L-tyrosine urea.

Mass calculated for $C_{38}H_{46}N_8O_{11}S$: 822.30; mass found (M+H)⁺: 823.0.

1-[5'-[(2S,3S)-N³-3-Aminobenzoyl-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 131)

Compound 131 was prepared using Fmoc-3-aminobenzoic acid, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{41}H_{47}FN_8O_{11}$: 846.33; mass found (M+H)⁺: 847.4.

1-[5'-[(2S,3S)-N³-L-Alanyl-N²-[N-[[(1S)-1-carboxy-4-hydroxyphenethyl]carbamoyl]-L-thiazolylalanyl]-N³-methyl-2,3-diaminobutyramido]-3',5'-dideoxy-α-L-arabinofuranosyl]uracil (Compound 132)

Compound 132 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and the L-thiazolylalanine/L-tyrosine urea.

Mass calculated for $C_{33}H_{43}N_9O_{11}S$: 773.28; mass found (M−H)⁻: 772.6.

1-[5'-[(2S,3S)-N³-L-Alanyl-N²-[N-[[(1S)-1-carboxy-2-naphthalenethyl]carbamoyl]-L-phenylalanyl]-N³-methyl-2,3-diaminobutyramido]-3',5'-dideoxy-α-L-arabinofuranosyl]uracil (Compound 133)

Compound 133 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-2-naphthylalanine urea.

Mass calculated for $C_{40}H_{48}N_8O_{10}$: 800.35; mass found $(M+H)^+$: 801.4.

1-[5'-[(2S,3S)-N³-L-Alanyl-N²-[N-[[(1S)-1-carboxy-4-hydroxyphenethyl]carbamoyl]-L-4-iodophenylalanyl]-N³-methyl-2,3-diaminobutyramido]-3',5'-dideoxy-α-L-arabinofuranosyl]uracil (Compound 134)

Compound 134 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-4-iodophenylalanine/L-tyrosine urea.

Mass calculated for $C_{36}H_{45}IN_8O_{11}$: 892.22; mass found $(M-H)^-$: 891.3.

1-[5'-[(2S,3S)-N³-L-Alanyl-N²-[N-[[(1S)-1-carboxy-4-hydroxyphenethyl]carbamoyl]-L-4-chlorophenylalanyl]-N³-methyl-2,3-diaminobutyramido]-3',5'-dideoxy-α-L-arabinofuranosyl]uracil (Compound 135)

Compound 135 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-4-chlorophenylalanine/L-tyrosine urea.

Mass calculated for $C_{36}H_{45}ClN_8O_{11}$: 801.3; mass found $(M-H)^-$: 800.4.

1-[5-(2S 3S)-N³-L-Alanyl-N²-[N-[[(1S)-1-carboxy-2-indol-3-ylethyl]carbamoyl]-L-cyclohexylalanyl]-N³-methyl-2,3-diaminobutyramido]-3',5'-dideoxy-α-L-arabinofuranosyl]uracil (Compound 136)

Compound 136 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-cyclohexylalanine/L-tryptophane urea.

Mass calculated for $C_{38}H_{53}N_9O_{10}$: 795.39. Mass found $(M+H)^+$: 796.5.

1-[5'-[(2S,3S)-N³-L-Alanyl-N²-[N-[[(1S)-1-carboxy-4-hydroxyphenethyl]carbamoyl]-L-homophenylalanyl]-N³-methyl-2,3-diaminobutyramido]-3',5'-dideoxy-α-L-arabinofuranosyl]uracil (Compound 137)

Compound 137 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-homophenylalanine/L-tyrosine urea.

Mass calculated for $C_{37}H_{48}N_8O_{11}$: 780.34; mass found $(M+H)^+$: 781.4.

1-[5'-[(2S,3S)-N³-L-Alanyl-N²-[N-[[(1S)-1-carboxy-2-indol-3-ylethyl]carbamoyl]-L-homophenylalanyl]-N³-methyl-2,3-diaminobutyramido]-3',5'-dideoxy-α-L-arabinofuranosyl]uracil (Compound 138)

Compound 138 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-homophenylalanine/L-tryptophane urea.

Mass calculated for $C_{39}H_{49}N_9O_{10}$: 803.36; mass found $(M+H)^+$: 804.4.

1-[5'-[(2S,3S)-N³-L-Alanyl-N²-[N-[[(1S)-1-carboxy-2-indol-3-ylethyl]carbamoyl]-L-2-fluorophenylalanyl]-N³-methyl-2,3-diaminobutyramido]-3',5'-dideoxy-α-L-arabinofuranosyl]uracil (Compound 139)

Compound 139 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-2-fluorophenylalanine/L-tryptophane urea.

Mass calculated for $C_{38}H_{46}FN_9O_{10}$: 807.33; mass found $(M-H)^-$: 806.3.

1-[5'-[(2S,3S)-N³-L-Alanyl-N²-[N-[[(1S)-1-carboxy-4-hydroxyphenethyl]carbamoyl]-L-2-fluorophenylalanyl]-N³-methyl-2,3-diaminobutyramido]-3',5'-dideoxy-α-L-arabinofuranosyl]uracil (Compound 140)

Compound 140 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-2-fluorophenylalanine/L-tyrosine urea.

Mass calculated for $C_{36}H_{45}FN_8O_{11}$: 784.32; mass found $(M-H)^-$: 783.4.

1-[5'-[(2S,3S)-N³-L-Alanyl-N²-[N-[[α(R,S)-1-carboxy-phenmethyl]carbamoyl]-L-4-fluorophenylalanyl]-N³-methyl-2,3-diaminobutyramido]-3',5'-dideoxy-α-L-arabinofuranosyl]uracil (Compound 141)

Compound 141 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-phenylglycine urea.

Mass calculated for $C_{35}H_{43}FN_8O_{10}$: 754.31; mass found $(M-H)^-$: 752.8.

1-[5'-[(2S,3S)-N³-L-Alanyl-N²-[N-[[α(S,R)-1-carboxy-phenmethyl]carbamoyl]-L-4-fluorophenylalanyl]-N³-methyl-2,3-diaminobutyramidol-3',5'-dideoxy-α-L-arabinofuranosyl]uracil (Compound 142)

Compound 142 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-phenylglycine urea.

Mass calculated for $C_{35}H_{43}FN_8O_{10}$: 754.31; mass found $(M-H)^-$: 752.8.

1-[5'-[(2S,3S)-N³-L-Alanyl-N²-[N-[[(1S)-1-carboxy-2-indol-3-ylethyl]carbamoyl]-L-(3,4)-difluorophenylalanyl]-N³-methyl-2,3-diaminobutyramido]-3',5'-dideoxy-α-L-arabinofuranosyl]uracil (Compound 143)

Compound 143 was prepared using Fmoc-L-alanine, (2S,3s)-3-methylamino-2-(tert-butoxyformamido)butyric acid 10 1-[5'-amino-3',5'-dideoxy-α-L-arabinofuranosyl]uracil 26 and L-(3,4)-difluorophenylalanine/L-tryptophane urea.

Mass calculated for $C_{38}H_{45}F_2N_9O_{10}$: 825.33; mass found $(M-H)^-$: 823.9.

1-[5'-[(2S,3S)-N³-L-Alanyl-N²-[N-[[(1S)-1-carboxy-4-hydroxyphenethyl]carbamoyl]-L-(3,4)-difluorophenylalanyl]-N³-methyl-2,3-diaminobutyramido)-3',5'-dideoxy-α-L-arabinofuranosyl]uracil (Compound 144)

Compound 144 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-(3,4)-difluorophenylalanine/L-tyrosine urea.

Mass calculated for $C_{36}H_{44}F_2N_8O_{11}$: 802.30; mass found $(M-H)^-$: 800.8.

1-[5'-[(2S,3S)-N³-L-Alanyl-N²-[N-[[(1S)-1-carboxy-
4-hydroxyphenethyl]carbamoyl]-L-4-
(trifluoromethyl)phenylalanyl]-N³-methyl-2,3-
diaminobutyramido]-3',5'-dideoxy-α-L-
arabinofuranosyl]uracil (Compound 145)

Compound 145 was prepared using Fmoc-L-alanine, (2S, 3S)-3-methylamino-2-(tert-butoxyformamido)butyric acid 10, 1-[5'-amino-3',5'-dideoxy-α-L-arabinofuranosyl]uracil 26 and L-4-trifluoromethylphenylalanine/L-tyrosine urea.

Mass calculated for $C_{37}H_{45}F_3N_8O_{11}$: 834.32; mass found (M+H)⁺: 835.5.

1-[5'-[(2S,3S)-N³-L-Alanyl-N²-[N-[[(1S)-1-carboxy-
2-indol-3-ylethyl]carbamoyl]-L-4-(trifluoromethyl)
phenylalanyl]-N³-methyl-2,3-diaminobutyramido]-
3',5'-dideoxy-α-L-arabinofuranosyl]uracil
(Compound 146)

Compound 146 was prepared using Fmoc-L-alanine, (2S, 3S)-3-methylamino-2-(tert-butoxyformamido)butyric acid 10, 1-[5'-amino-3',5'-dideoxy-(-L-arabinofuranosyl]uracil 26 and L-4-(trifluoromethyl)phenylalanine/L-tryptophane urea.

Mass calculated for $C_{39}H_{46}F_3N_9O_{10}$: 857.33; mass found (M–H)⁻: 856.0.

1-[5'-[(2S,3S)-N²-[N-[[(1S)-1-Carboxy-2-indol-3-
ylethyl]carbamoyl]-L-phenylalanyl]-N³-L-lysinyl-
N³-methyl-2,3-diaminobutyramido]-3',5'-dideoxy-α-
L-arabinofuranosyl]uracil (Compound 147)

Compound 147 was prepared using Fmoc-L-lysine(Boc), (2S,3S)-3-methylamino-2-(tert-butoxyformamido)butyric acid 10, 1-[5'-amino-3',5'-dideoxy-α-L-arabinofuranosyl] uracil 26 and the L-phenylalanine/L-tryptophane urea.

Mass calculated for $C_{41}H_{54}N_{10}O_{10}$: 846.4; mass found (M–H)⁻: 845.0.

1-[5'-[(2S,3S)-N³-L-Alanyl-N²-[N-[[(1S)-1-carboxy-
2-indol-3-ylethyl]carbamoyl]-L-lysinyl]-N³-methyl-
2,3-diaminobutyramido]-3',5'-dideoxy-α-L-
arabinofuranosyl]uracil (Compound 148)

Compound 148 was prepared using Fmoc-L-alanine, (2S, 3S)-3-methylamino-2-(tert-butoxyformamido)butyric acid 10, 1-[5'-amino-3',5'-dideoxy-α-L-arabinofuranosyl]uracil 26 and L-lysine/L-tryptophane urea.

Mass calculated for $C_{35}H_{51}N_{10}O_{10}$: 771.38; mass found (M–H)⁻: 770.1.

1-[5'-[(2S,3S)-N³-L-Alanyl-N²-[N-[[(1S)-1-carboxy-
5-imidazylethyl]carbamoyl]-N³-methyl-2,3-
diaminobutyramido]-3',5'-dideoxy-α-L-
arabinofuranosyl]uracil (Compound 149)

Compound 149 was prepared using Fmoc-L-alanine, (2S, 3S)-3-methylamino-2-(tert-butoxyformamido)butyric acid 10, 1-[5'-amino-3',5'-dideoxy-α-L-arabinofuranosyl]uracil 26 and pentafluorophenyl L-phenylalanine/L-histidine urea.

Mass calculated for $C_{33}H_{44}N_{10}O_{10}$: 740.32; mass found (M+H)⁺: 740.8.

1-[5'-[(2S,3S)-N³-(L-O-Benzylserinyl)-N²-[N-
[[(1S)-1-carboxy-4-hydroxyphenethyl]carbamoyl]-
L-phenylalanyl]-N³-methyl-2,3-
diaminobutyramido]-3',5'-dideoxy-α-L-
arabinofuranosyl]uracil (Compound 150)

Compound 150 was prepared using Fmoc-L-O-benzylserine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tyrosine urea.

Mass calculated for $C_{43}H_{52}N_8O_{12}$: 872.37; mass found (M+H)⁺: 873.4.

1-[5'-[(2S,3S)-N²-[N-[[(1S)-1-Carboxy-2-indol-3-
ylethyl]carbamoyl]-L-phenylalanyl]-N³-methyl-2,3-
diaminobutyramido]-3',5'-dideoxy-α-L-
arabinofuranosyl]uracil (Compound 151)

Compound 151 was prepared using (2S,3S)-3-methylamino-2-(tert-butoxyformamido)butyric acid 10, 1-[5'-amino-3,5'-dideoxy-α-L-arabinofuranosyl]uracil 26 and L-phenylalanine/L-tryptophane urea.

Mass calculated for $C_{35}H_{42}N_8O_9$: 718.31; mass found (M+H)⁺: 719.4.

1-[5'-[(2S,3S)-N³-L-Alanyl-N²-[N-[[(1S)-1-carboxy-
4-hydroxyphenethyl)carbamoyl]-L-3-(2-naphthyl)
alanyl]-N³-methyl-2,3-diaminobutyramido]-3',5'-
dideoxy-α-L-arabinofuranosyl]uracil (Compound
152)

Compound 152 was prepared using Fmoc-L-alanine, (2S, 3S)-3-methylamino-2-(tert-butoxyformamido)butyric acid 10, 1-[5'-amino-3',5'-dideoxy-α-L-arabinofuranosyl]uracil 26 and L-3-(2-naphthyl)alanine/L-tyrosine urea.

Mass calculated for $C_{40}H_{48}N_8O_{11}$: 816.34; mass found (M+H)⁺: 817.4.

1-[5'-[(2S,3S)-N³-L-Alanyl-N²-[N-[[(1S)-1-carboxy-
2-indol-3-ylethyl]carbamoyl]-L-3-(2-naphthyl)
alanyl]-N³-methyl-2,3-diaminobutyramidol-3',5'-
dideoxy-α-L-arabinofuranosyl]uracil (Compound
153)

Compound 153 was prepared using Fmoc-L-alanine, (2S, 3S)-3-methylamino-2-(tert-butoxyformamido)butyric acid 10, 1-[5,-amino-3',5'-dideoxy-α-L-arabinofuranosyl]uracil 26 and L-3-(2-naphthyl)alanine/L-tryptophane urea.

Mass calculated for $C_{42}H_{49}N_9O_{10}$: 839.36; mass found (M+H)⁺: 840.4.

1-[5'-[(2S,3S)-N³-L-Alanyl-N²-[(2R)-2-benzyl-N-
[(1S)-1-carboxy-2-indol-3-ylethyl]succinimoyl]-N³-
methyl-2,3-diaminobutyramido]-3',5'-dideoxy-α-L-
arabinofuranosyl]uracil (Compound 154)

Compound 154 was prepared using Fmoc-L-alanine, (2S, 3S)-3-methylamino-2-(tert-butoxyformamido)butyric acid 10, 1-[5'-amino-3',5'-dideoxy-α-L-arabinofuranosyl]uracil 26 and pentafluorophenyl (1S)-succinate/L-tryptophane dipeptide.

Mass calculated for $C_{40}H_{52}N_8O_{10}$: 804.38; mass found (M+H)⁺: 805.7.

1-[5'-[(2S,3S)-N³-L-Alanyl-N²-[N-[[(1S)-1-carboxy-
2-indol-3-ylethyl)carbamoyl]-L-4-biphenylalanyl]-
N³-methyl-2,3-diaminobutyramidol-3',5'-dideoxy-α-
L-arabinofuranosyl]uracil (Compound 155)

Compound 155 was prepared using Fmoc-L-alanine, (2S, 3S)-3-methylamino-2-(tert-butoxyformamido)butyric acid 10, (5'-amino-3',5'-dideoxy-α-L-arabinofuranosyl]uracil 26 and L-4-biphenylalanine/L-tryptophane urea.

Mass calculated for $C_{44}H_{51}N_9O_{10}$: 865.37; mass found (M+H)⁺: 866.3.

1-[5'-[(2S,3S)-N²-[N-[[(1S)-1-Carboxy-2-indol-3-
ylethyl]carbamoyl]-L-phenylalanyl]-N³-L-
phenylalanyl-N³-methyl-2,3-diaminobutyramido]-3',
5'-dideoxy-α-L-arabinofuranosyl]uracil (Compound
156)

Compound 156 was prepared using Fmoc-L-phenylalanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tryptophane urea.

Mass calculated for $C_{44}H_{51}N_9O_{10}$: 865.37; mass found (M+H)$^+$: 866.3.

1-[5'-[(2S,3S)-N$^3$-L-Alanyl-N$^2$-[N-[[(1S)-1-carboxy-4-hydroxyphenethyl]carbamoyl]-L-4-fluorophenylalanyl]-N$^3$-methyl-2,3-diaminobutyramido]-3',5'-dideoxy-α-L-arabinofuranosyl]uracil (Compound 157)

Compound 157 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tyrosine urea.

Mass calculated for $C_{36}H_{45}FN_8O_{11}$: 784.32; mass found (M+H)$^+$: 785.6.

1-[5'-[(2S,3S)-N$^3$-L-Alanyl-N$^2$-[N-[[(1S)-1-carboxy-2-indol-3-ylethyl]carbamoyl]-L-4-fluorophenylalanyl]-N$^3$-methyl-2,3-diaminobutyramidol-3',5'-dideoxy-α-L-arabinofuranosyl]uracil (Compound 158)

Compound 158 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-4-fluorophenylalanine/L-tryptophane urea.

Mass calculated for $C_{38}H_{46}FN_9O_{10}$: 807.31; mass found (M+H)$^+$: 808.1.

1-[5'-[(2S,3S)-N$^2$-[N-[[(1S)-1-Carboxy-2-indol-3-ylethyl]carbamoyl]-L-phenylalanyl]-N$^3$-L-leucyl-N$^3$-methyl-2,3-diaminobutyramido]-3',5'-dideoxy-α-L-arabinofuranosyl]uracil (Compound 159)

Compound 159 was prepared using Fmoc-L-leucine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tryptophane urea.

Mass calculated for $C_{41}H_{53}N_9O_{10}$: 831.39; mass found (M+H)$^+$: 832.6.

1-[5$^1$-[(2S,3S)-N$^3$-L-Alanyl-N$^2$-[N-[[(1S)-1-carboxy-4-hydroxyphenethyl]carbamoyl]-L-phenylalanyl]-N$^3$-methyl-2,3-diaminobutyramido-3',5'-dideoxy-α-L-arabinofuranosyl]uracil (Compound 160)

Compound 160 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tyrosine urea.

Mass calculated for $C_{36}H_{46}N_8O_{11}$: 766.33; mass found (M+H)$^+$: 767.1.

1-[5'-[(2S,3S)-N$^3$-L-Alanyl-N$^2$-[N-[[(1S)-1-carboxy-4-hydroxyphenethyl)carbamoyl]-L-leucyl]-N$^3$-methyl-2,3-diaminobutyramido]-3',5'-dideoxy-α-L-arabinofuranosyl]uracil (Compound 161)

Compound 161 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-leucine/L-tyrosine urea.

Mass calculated for $C_{33}H_{48}N_8O_{11}$: 732.34; mass found (M+H)$^+$: 733.1.

1-[5'-[(2S,3S)-N$^2$-[N-[[(1S)-1-Carboxy-2-indol-3-ylethyl]carbamoyl]-L-methionyl]-N$^3$-L-methionyl-N$^3$-methyl-2,3-diaminobutyramido]-3',5'-dideoxy-α-L-arabinofuranosyl]uracil (Compound 162)

Compound 162 was prepared using Fmoc-L-methionine, ((2S,3S)-3-methylamino-2-(tert-butoxyformamido)butyric acid 10, 1-[5'-amino-3',5'-dideoxy-α-L-arabinofuranosyl]uracil 26 and L-methionine/L-tryptophane urea.

Mass calculated for $C_{36}H_{51}N_9O_{10}S_2$: 833.32; mass found (M+H)$^+$: 834.0.

1-[5'-[(2S,3S)-N$^2$-[N-[[(1S)-1-Carboxy-2-indol-3-ylethyl]carbamoyl]-L-phenylalanyl]-N$^3$-L-tyrosyl-N$^3$-methyl-2,3-diaminobutyramido]-3',5'-dideoxy-α-L-arabinofuranosyl]uracil (Compound 163)

Compound 163 was prepared using Fmoc-L-tyrosine, (2S,3S)-3-methylamino-2-(tert-butoxyformamido)butyric acid 10, 1-[5'-amino-3',5'-dideoxy-α-L-arabinofuranosyl]uracil 26 and L-phenylanine/L-tryptophane urea.

Mass calculated for $C_{44}H_{51}N_9O_{11}$: 881.37; mass found (M−H)$^-$: 880.1.

1-[5'-[(2S,3S)-N$^3$-L-Alanyl-N$^2$-[N-[[(1S)-1-carboxy-2-indol-3-ylethyl]carbamoyl]-L-phenylalanyl]-N$^3$-methyl-2,3-diaminobutyramido]-3',5'-dideoxy-α-L-arabinofuranosyl]uracil (Compound 164)

Compound 164 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-phenylalanine/L-tryptophane urea.

Mass calculated for $C_{38}H_{47}N_9O_{10}$: 789.34; mass found (M+H)$^+$: 790.4.

1-[5'-[(2S,3S)-N$^2$-[N-[[(1S)-1-Carboxy-2-indol-3-ylethyl]carbamoyl]-L-alanyl]-N$^3$-methyl-2,3-diaminobutyramido]-3',5'-dideoxy-α-L-arabinofuranosyl]uracil (Compound 165)

Compound 165 was prepared using (2S,3S)-3-methylamino-2-(tert-butoxyformamido)butyric acid 10, 1-[5'-amino-3',5'-dideoxy-α-L-arabinofuranosyl]uracil 26 and N-[(1S)-1-[(pentafluorophenoxy))carbonyl]ethyl]carbamoyl]-L-tryptophane, tert-butyl ester 29.

Mass calculated for $C_{29}H_{38}N_8O_9$: 642.29; mass found (M+H)$^+$: 643.3.

1-[5'-[(2S,3S)-N$^3$-L-Alanyl-N$^2$-[N-([(1S)-1-carboxy-phenethyl]carbamoyl]-L-leucinyl]-N$^3$-methyl-2,3-diaminobutyramido]-3',5'-dideoxy-α-L-arabinofuranosyl]uracil (Compound 166)

Compound 166 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-leucine/L-phenylalanine urea.

Mass calculated for $C_{34}H_{50}N_8O_9$: 714.37; mass found (M+H)$^+$: 715.3.

1-[5'-[(2S,3S)-N$^3$-L-Alanyl-N$^2$-[N-[[(1S)-1-carboxy-2-indol-3-ylethyl]carbamoyl]-L-methionyl]-N$^3$-methyl-2,3-diaminobutyramido]-3',5'-dideoxy-α-L-arabinofuranosyl]uracil (Compound 167)

Compound 167 was prepared using Fmoc-L-alanine, (2S,3S)-3-methylamino-2-(tert-butoxyformamido)butyric acid 10, 1-[5'-amino-3',5'-dideoxy-α-L-arabinofuranosyl]uracil 26 and L-methionine/L-tryptophane urea.

Mass calculated for $C_{34}H_{47}N_9O_{10}S$: 773.31; mass found (M−H)$^-$: 771.7.

1-[5'-[(2S,3S)-N$^2$-[N-[[(1S)-1-Carboxy-2-indol-3-ylethyl]carbamoyl]-L-alanyl]-N$^3$-L-methionyl-N$^3$-methyl-2,3-diaminobutyramido]-3',5'-dideoxy-α-L-arabinofuranosyl]uracil (Compound 168)

Compound 168 was prepared using Fmoc-L-methionine, (2S,3S)-3-methylamino-2-(tert-butoxyformamido)butyric acid 10, 1-[5'-amino-3',5'-dideoxy-α-L-arabinofuranosyl] uracil 26, N-[(1S)-1-[(pentafluorophenoxy))-carbonyl] ethyl]carbamoyl]-L-tryptophane, tert-butyl ester 29.

Mass calculated for $C_{34}H_{47}N_9O_{10}S$: 773.31; mass found $(M+H)^+$: 774.6.

1-[5'-[(2S,3S)-N³-L-Alanyl-N²-[N-[[(1S)-1-carboxy-2-indol-3-ylethyl]carbamoyl]-L-valinyl]-N³-methyl-2,3-diaminobutyramido]-3',5'-dideoxy-α-L-arabinofuranosyl]uracil (Compound 169)

Compound 169 was prepared using Fmoc-L-alanine, (2S, 3S)-3-methylamino-2-(tert-butoxyformamido)butyric acid 10, 1-[5'-amino-3',5'-dideoxy-α-L-arabinofuranosyl]uracil 26 and L-valine/L-tryptophane urea.

Mass calculated for $C_{34}H_{47}N_9O_{10}$: 741.34; mass found $(M+H)^+$: 742.0.

1-[5'-[(2S,3S)-N³-L-Alanyl-N²-[N-[[(1S)-1-carboxy-2-indol-3-ylethyl]carbamoyl]-L-leucinyl]-N³-methyl-2,3-diaminobutyramido]-3',5'-dideoxy-α-L-arabinofuranosyl]uracil (Compound 170)

Compound 170 was prepared using Fmoc-L-alanine, (2S, 3S)-3-methylamino-2-(tert-butoxyformamido)butyric acid 10, 1-[5'-amino-3',5'-dideoxy-α-L-arabinofuranosyl]uracil 26 and L-leucine/L-tryptophane urea.

Mass calculated for $C_{35}H_{49}N_9O_{10}$: 755.5; mass found $(M+H)^+$: 756.4.

1-[5'-[(2S,3S)-N³-D-Alanyl-N²-[N-[[(1S)-1-carboxy-2-indol-3-ylethyl]carbamoyl]-L-alanyl]-N³-methyl-2,3-diaminobutyramido]-3',5'-dideoxy-α-L-arabinofuranosyl]uracil (Compound 171)

Compound 171 was prepared using Fmoc-D-alanine, (2S, 3S)-3-methylamino-2-(tert-butoxyformamido)butyric acid 10, 1-[5'-amino-3',5'-dideoxy-α-L-arabinofuranosyl]uracil 26 and N-[(1S)-1-[(pentafluorophenoxy))-carbonyl]ethyl] carbamoyl]-L-tryptophane, tert-butyl ester 29.

Mass calculated for $C_{32}H_{43}N_9O_{10}$: 713.31; mass found $(M+H)^+$: 714.4.

1-[5'-[(2S,3S)-N³-L-Alanyl-N²-[N-[[(1S)-1-carboxy-2-indol-3-ylethyl]carbamoyl]-L-alanyl]-N³-methyl-2,3-diaminobutyramido]-3',5'-dideoxy-α-D-ribofuranosyl]uracil (Compound 172)

Compound 172 was prepared using Fmoc-L-alanine, (2S, 3S)-3-methylamino-2-(tert-butoxyformamido)butyric acid 10, 1-[5'-amino-3',5'-dideoxy-β-D-ribofuranosyl]uracil 18 and N-[(1S)-1-[(pentafluorophenoxy))-carbonyl]ethyl] carbamoyl]-L-tryptophane, tert-butyl ester 29.

Mass calculated for $C_{32}H_{43}N_9O_{10}$: 713.8; mass found $(M+H)^+$: 714.4.

Biological Evaluation

It will be appreciated that, in any given series of compounds, a spectrum of biological activity will be observed. In its presently preferred embodiment, this invention relates to novel dihydro uridyl peptide antibiotic compounds expected to exhibit superior characteristics regarding the establishment of resistance within a population of bacteria to the compounds or this invention and/or the appearance of cross-resistance by populations of bacteria resistant to other antibiotics to the compound of this invention.

The following assays are employed to select those compounds demonstrating the optimal degree of the desired characteristics. Results obtained with representative, but by no means limiting, compounds of this invention are shown in Tables 4, 6, 8 and 10.

Compounds of this invention were evaluated for antimicrobial acitivity against several bacterial strains using a broth microdilution assay or an agar dilution assay, both of which were performed in the manner recommended by the National Committee for Clinical Laboratory Standards (NCCLS), Methods for Dilution of Antimicrobial Susceptibility Tests for Bacteria that grow aerobically—$4^{th}$ ed., NCCLS Document M7-A4, Vol. 17, No. 2, which is incorporated by reference as if fully set forth herein.

Results are reported in terms of the minimum inhibitory concentration (MIC) which is defined herein as the lowest concentration of the test compound at which the visible growth of the target bacteria is completely inhibited.

Compounds were tested against several panels of bacteria. In a first panel, Table 3, several strains of *Pseudomonas aeruginosa, Escherichia coli* and *Staphylococcus aureus* were employed as the target bacteria.

TABLE 3

| Bacteria | Strain | Characteristic |
|---|---|---|
| *Pseudomonas aeruginosa* | PAM 1020 | Wild type |
| *Pseudomonas aeruginosa* | PAM 1154 | OprM::Hg |
| *Pseudomonas aeruginosa* | PAM 1135 | High Level UPA resistance |
| *Pseudomonas aeruginosa* | PAM 1323 | Medium Level UPA resistance |
| *Escherichia Coli* | MC 4100 | Wild Type |
| *Escherichia Coli* | MC 4100 AcrAB | ΔAcrAB |
| *Escherichia Coli* | MC 4100 AcrAB UPA3r | ΔAcrAB, UPA resistant |
| *Staphylococcus aureus* | ATCC 29213 | Wild Type |
| *Staphylococcus aureus* | 8325-4 | Wild Type |
| *Pasteurella multocida* | pm002 | Wild Type |

For the bacteria in Table 3, the assay was performed in Mueller-Hinton Broth (MHB) with a final bacterial inoculum of $5\times10^5$ CFU/ml and a final volume of 100 μl. Control drugs, including imipenem and pacidimycin 4, and the test compounds were prepared at a concentration which was twice the desired final concentration (256 μg/ml). Dilution of the controls and the test compounds was accomplished directly on the test plates by serial 2-fold dilution using a multi-channel pipette. Both a positive and a negative growth control was included in each plate.

The bacterial inocula were prepared as follows. Bacterial strains were grown overnight at 35° C. in MHB. For each strain, one isolated colony was used to inoculate a volume of 8 ml of MHB and these cultures were incubated overnight (approximately 20 hours) at 35° C. in a shaking incubator. The culture was then diluted 1:10 and allowed to grow for an additional one hour at 35° C. in a shaking incubator. The inocula were then prepared by diluting the early log phase (one hour) cultures 1:2000 with fresh MHB. A volume of 50 μl of the inocula was added to each well, resulting in an inoculum of approximately $5\times10^5$ CFU/ml. The exact inocula were determined by putting 10 μl of 10-fold serial dilution of the bacterial suspensions onto TSA. After overnight incubation at 35° C., colony-forming units were counted manually.

The microtiter plates were incubated for 20 hours at 35° C. and were then read using a microtiterplate reader (Molecular Devices) at 650 nm as well as being visually observed using a microtiterplate reading mirror. The results with this panel of bacteria using the compounds of this invention are shown in Table 4. It is to be understood that the compounds tested in this panel and the results obtained are not to be construed as limiting the scope of this invention in any way.

TABLE 4

| MIC (μg/ml) Broth microdilution | | | | | | |
|---|---|---|---|---|---|---|
| Microorganism | PAC4 | 100 | 101 | 102 | 103 | 104 |
| P. aeruginosa PAM1020 | 64 | 32 | 128 | 32 | 16 | 32 |
| P. aeruginosa PAM 1154 OprM::Hg | 8 | 8 | 8 | 8 | 8 | 4 |
| P. aeruginosa PAM 1135 UPA1r | >256 | >512 | >512 | >512 | >512 | >512 |
| P. aeruginosa PAM 1323 | >256 | >512 | >512 | 512 | 512 | <512 |
| E. coli MC 4100 | 256 | 8 | >512 | 512 | 512 | <512 |
| E. coli AcrAB | 2 | <1 | 2 | <1 | 2 | 16 |
| E. coli AcrAB UPA3r | 128 | 2 | 128 | 16 | 32 | 128 |
| S. aureus ATCC 29213 | 256 | >512 | >512 | >512 | 512 | >512 |
| S. aureus 8325-4 | 256 | 512 | >512 | 512 | 256 | >512 |
| P. multocida pm002 | 128 | 256 | >512 | 256 | 256 | 256 |
| Microorganism | 105 | 106 | 107 | 108 | 109 | 110 |
| P. aeruginosa PAM 1020 | 256 | 32 | 256 | 256 | 4 | 64 |
| P. aeruginosa PAM 1154 OprM::Hg | 64 | 64 | 64 | 32 | <1 | 32 |
| P. aeruginosa PAM 1135 UPA1r | 256 | 256 | >512 | >512 | >512 | 256 |
| P. aeruginosa PAM 1323 | 256 | 256 | >512 | 512 | 128 | 256 |
| E. coli MC 4100 | 512 | 512 | 16 | 256 | 128 | 512 |
| E. coli AcrAB | 16 | 8 | <1 | <1 | <1 | 16 |
| E. coli AcrAB UPA3r | 512 | 512 | 8 | 16 | 8 | 512 |
| S. aureus ATCC 29213 | >512 | >512 | >512 | >512 | >512 | >512 |
| S. aureus 8325-4 | >512 | >512 | >512 | >512 | >512 | >512 |
| P. multocida pm002 | 512 | 512 | >512 | 512 | 128 | 512 |
| Microorganism | 111 | 112 | 113 | 114 | 115 | 116 |
| P. aeruginosa PAM 1020 | 128 | 16 | 64 | 16 | 4 | 32 |
| P. aeruginosa PAM 1154 OprM::Hg | 16 | 4 | 64 | 16 | 2 | 8 |
| P. aeruginosa PAM 1135 UPA1r | 256 | >512 | >512 | 256 | >512 | >512 |
| P. aeruginosa PAM 1323 | 256 | 256 | >512 | 256 | 256 | 512 |
| E. coli MC 4100 | 512 | >512 | >512 | 512 | >512 | 256 |
| E. coli AcrAB | 8 | 2 | 8 | 8 | 8 | <1 |
| E. coli AcrAB UPA3r | 512 | 16 | 64 | 512 | 32 | 16 |
| S. aureus ATCC 29213 | >512 | >512 | >512 | >512 | >512 | 512 |
| S. aureus 8325-4 | >512 | >512 | >512 | >512 | >512 | 256 |
| P. multocida pm002 | 512 | 128 | 512 | 256 | 128 | 128 |
| Microorganism | 117 | 118 | 119 | 120 | 121 | 122 |
| P. aeruginosa PAM 1020 | 64 | 128 | 64 | 16 | 64 | 64 |
| P. aeruginosa PAM 1154 OprM::Hg | 64 | 128 | 32 | 4 | 4 | 16 |
| P. aeruginosa PAM 1135 UPA1r | >512 | 256 | >512 | >512 | >512 | >512 |
| P. aeruginosa PAM 1323 | >512 | 256 | >512 | 512 | >512 | >512 |
| E. coli MC 4100 | >512 | 512 | >512 | >512 | >512 | >512 |
| E. coli AcrAB | <1 | 8 | 4 | 8 | 2 | 4 |
| E. coli AcrAB UPA3r | 32 | 256 | 64 | 128 | 16 | 64 |
| S. aureus ATCC 29213 | >512 | >512 | >512 | >512 | >512 | >512 |
| S. aureus 8325-4 | >512 | >512 | >512 | >512 | >512 | 512 |
| P. multocida pm002 | 256 | 256 | >512 | 512 | >512 | >512 |
| Microorganism | 123 | 124 | 125 | 126 | 127 | 128 |
| P. aeruginosa PAM 1020 | 32 | 512 | 64 | 128 | >512 | 8 |
| P. aeruginosa PAM 1154 OprM::Hg | 16 | 128 | 8 | 16 | 512 | <1 |
| P. aeruginosa PAM 1135 UPA1r | 256 | >512 | >512 | >512 | >512 | >512 |
| P. aeruginosa PAM 1323 | 256 | >512 | >512 | >512 | >512 | >512 |
| E. coli MC 4100 | 512 | 256 | >512 | 16 | >512 | 256 |
| E. coli AcrAB | 4 | 2 | 8 | <1 | 4 | 2 |
| E. coli AcrAB UPA3r | 512 | 128 | 64 | 4 | 32 | 16 |
| S. aureus ATCC 29213 | >512 | >512 | >512 | 512 | >512 | 512 |
| S. aureus 8325-4 | >512 | >512 | >512 | 256 | 256 | 256 |
| P. multocida pm002 | >512 | >512 | >512 | 512 | >512 | 64 |

TABLE 4-continued

| MIC (μg/ml) Broth microdilution | | | | | | |
|---|---|---|---|---|---|---|
| Microorganism | 129 | 130 | 131 | 132 | 133 | 134 |
| P. aeruginosa PAM 1020 | 32 | 64 | 512 | 128 | 64 | 256 |
| P. aeruginosa PAM 1154 OprM::Hg | 8 | 16 | 512 | 32 | 32 | 32 |
| P. aeruginosa PAM 1135 UPA1r | >512 | >512 | >512 | >512 | >512 | >512 |
| P. aeruginosa PAM 1323 | >512 | >512 | >512 | >512 | >512 | >512 |
| E. coli MC 4100 | 8 | 64 | >512 | 256 | 256 | 128 |
| E. coli AcrAB | <1 | 8 | 16 | 8 | <1 | <1 |
| E. coli AcrAB UPA3r | 2 | 16 | 512 | 32 | 32 | 32 |
| S. aureus ATCC 29213 | >512 | 128 | 512 | >512 | 256 | 512 |
| S. aureus 8325-4 | 512 | 256 | >512 | >512 | 128 | 512 |
| P. multocida pm002 | 256 | 512 | >512 | >512 | 256 | >512 |
| Microorganism | 135 | 136 | 137 | 138 | 139 | 140 |
| P. aeruginosa PAM 1020 | 64 | 128 | 64 | 32 | 64 | 64 |
| P. aeruginosa PAM 1154 OprM::Hg | 16 | 64 | 128 | 8 | 8 | 4 |
| P. aeruginosa PAM 1135 UPA1r | >512 | >512 | >512 | >512 | >512 | >512 |
| P. aeruginosa PAM 1323 | >512 | >512 | >512 | >512 | 512 | 512 |
| E. coli MC 4100 | 8 | >512 | 512 | 512 | >512 | 64 |
| E. coli AcrAB | <1 | 4 | 16 | 2 | 2 | <1 |
| E. coli AcrAB UPA3r | 2 | 64 | 256 | 256 | 64 | 8 |
| S. aureus ATCC 29213 | 512 | >512 | >512 | >512 | 256 | 512 |
| S. aureu 8325-4 | >512 | >512 | >512 | >512 | 256 | 512 |
| P. multocida pm002 | 512 | >512 | >512 | >512 | 256 | >512 |
| Microorganism | 141 | 142 | 143 | 144 | 145 | 146 |
| P. aeruginosa PAM 1020 | >512 | 512 | 128 | 64 | 256 | 256 |
| P. aeruginosa PAM 1154 OprM::Hg | 512 | 64 | 16 | 8 | 32 | 32 |
| P. aeruginosa PAM 1135 UPA1r | >512 | >512 | >512 | >512 | >512 | >512 |
| P. aeruginosa PAM 1323 | >512 | >512 | >512 | >512 | >512 | >512 |
| E. coli MC 4100 | >512 | 512 | 256 | 4 | 512 | 512 |
| E. coli AcrAB | 16 | 4 | <1 | <1 | 4 | 2 |
| E. coli AcrAB UPA3r | >512 | 32 | 16 | <1 | 128 | 64 |
| S. aureus ATCC 29213 | >512 | >512 | 512 | >512 | >512 | 512 |
| S. aureus 8325-4 | >512 | >512 | 256 | 512 | >512 | 256 |
| P. multocida pm002 | >512 | >512 | 128 | 256 | 512 | 64 |
| Microorganism | 147 | 148 | 149 | 150 | 151 | 152 |
| P. aeruginosa PAM 1020 | 32 | 128 | 512 | 256 | 256 | 256 |
| P. aeruginosa PAM 1154 OprM::Hg | 16 | 8 | 8 | 64 | 32 | 64 |
| P. aeruginosa PAM 1135 UPA1r | >512 | >512 | >512 | 256 | 256 | >512 |
| P. aeruginosa PAM 1323 | — | >512 | >512 | 256 | 256 | >512 |
| E. coli MC 4100 | >512 | >512 | 512 | 512 | 512 | 256 |
| E. coli AcrAB | >512 | >512 | 16 | 8 | 4 | 2 |
| E. coli AcrAB UPA3r | >512 | >512 | 64 | 512 | 128 | 64 |
| S. aureus ATCC 29213 | >512 | >512 | >512 | >512 | >512 | >512 |
| S. aureus 8325-4 | >512 | >512 | >512 | >512 | >512 | >512 |
| P. multocida pm002 | — | >512 | 256 | 512 | 256 | >512 |
| Microorganism | 153 | 154 | 155 | 156 | 157 | 158 |
| P. aeruginosa PAM 1020 | 128 | 64 | 256 | 32 | 128 | 64 |
| P. aeruginosa PAM 1154 OprM::Hg | 16 | 8 | 64 | 32 | 16 | 8 |
| P. aeruginosa PAM 1135 UPA1r | >512 | >512 | 512 | 256 | >512 | 256 |
| P. aeruginosa PAM 1323 | >512 | >512 | 256 | 256 | >512 | 256 |
| E. coli MC 4100 | 512 | >512 | 512 | 512 | 4 | 512 |
| E. coli AcrAB | 2 | 8 | 8 | 4 | <1 | <1 |
| E. coli AcrAB UPA3r | 128 | 128 | 512 | 512 | <1 | 32 |
| S. aureus ATCC 29213 | 512 | >512 | >512 | >512 | >512 | 512 |
| S. aureus 8325-4 | 256 | >512 | 512 | >512 | 512 | 512 |
| P. multocida pm002 | 64 | >512 | 32 | 256 | 256 | 64 |

TABLE 4-continued

| | MIC (μg/ml) Broth microdilution | | | | | |
|---|---|---|---|---|---|---|
| Microorganism | 159 | 160 | 161 | 162 | 163 | 164 |
| P. aeruginosa PAM 1020 | 128 | 16 | 16 | 64 | 16 | 16 |
| P. aeruginosa PAM 1154 OprM::Hg | 8 | 8 | 8 | 16 | 16 | 4 |
| P. aeruginosa PAM 1135 UPA1$^r$ | 256 | >512 | >512 | 256 | 256 | 256 |
| P. aeruginosa PAM 1323 | 256 | >512 | 256 | 256 | 256 | 256 |
| E. coli MC 4100 | >512 | 32 | >512 | 512 | 512 | 512 |
| E. coli AcrAB | 2 | <1 | 32 | 16 | 4 | <1 |
| E. coli AcrAB UPA3$^r$ | 64 | 4 | 256 | 512 | 512 | 64 |
| S. aureus ATCC 29213 | >512 | 512 | >512 | >512 | >512 | 256 |
| S. aureus 8325-4 | >512 | 512 | >512 | >512 | >512 | 128 |
| P. multocida pm002 | 128 | 256 | 512 | 512 | 256 | 128 |
| Microorganism | 165 | 166 | 167 | 168 | 169 | 170 |
| P. aeruginosa PAM 1020 | >512 | >512 | 512 | 64 | 128 | 64 |
| P. aeruginosa PAM 1154 OprM::Hg | 128 | >512 | 256 | 8 | 128 | 4 |
| P. aeruginosa PAM 1135 UPA1$^r$ | >512 | >512 | >512 | >512 | >512 | >512 |
| P. aeruginosa PAM 1323 | >512 | >512 | 512 | >512 | 64 | — |
| E. coli MC 4100 | >512 | >512 | 512 | >512 | 256 | 128 |
| E. coli AcrAB | 4 | 16 | 4 | 4 | 2 | 2 |
| E. coli AcrAB UPA3$^r$ | 128 | 256 | 128 | 256 | 32 | 1 |
| S. aureus ATCC 29213 | >512 | >512 | >512 | >512 | >512 | >512 |
| S. aureus 8325-4 | >512 | >512 | >512 | >512 | >512 | >512 |
| P. multocida pm002 | 256 | 512 | 128 | 256 | 128 | — |
| Microorganism | 171 | 172 | 173 | 2 | 3 | 4 |
| P. aeruginosa PAM 1020 | 512 | 64 | 512 | 64 | 16 | 8 |
| P. aeruginosa PAM 1154 OprM::Hg | 32 | 4 | 32 | 4 | 8 | 4 |
| P. aeruginosa PAM 1135 UPA1$^r$ | >512 | >512 | >512 | 512 | >512 | 512 |
| P. aeruginosa PAM 1323 | — | — | — | — | — | — |
| E. coli MC 4100 | >512 | 16 | >512 | 256 | 128 | 256 |
| E. coli AcrAB | 16 | 128 | 16 | 4 | 2 | 2 |
| E. coli AcrAB UPA3$^r$ | 128 | 16 | 128 | 16 | 32 | 64 |
| S. aureus ATCC 29213 | >512 | 512 | >512 | >512 | 512 | >512 |
| S. aureus 8325-4 | >512 | >512 | >512 | >512 | 256 | >512 |
| P. multocida pm002 | — | — | — | — | — | — |
| Microorganism | | | | | 5 | 34 |
| P. aeruginosa PAM 1020 | | | | | 64 | 64 |
| P. aeruginosa PAM 1154 OprM::Hg | | | | | 16 | 4 |
| P. aeruginosa PAM 1135 UPA1$^r$ | | | | | >512 | >512 |
| P. aeruginosa PAM 1323 | | | | | — | — |
| E. coli MC 4100 | | | | | 512 | 128 |
| E. coli AcrAB | | | | | 8 | 2 |
| E. coli AcrAB UPA3$^r$ | | | | | 32 | 16 |
| S. aureus ATCC 29213 | | | | | >512 | 512 |
| S. aureus 8325-4 | | | | | >512 | >512 |
| P. multocida pm002 | | | | | — | — |

In a second panel, Table 5, compounds of this invention were tested for their antimicrobial activity against the bacterial strains H. influenzae hf032 and S. pneumoniae ATCC 49629.

TABLE 5

| Bacteria | Strain | Characteristic |
|---|---|---|
| Haemophilus influenzae | hf032 | Wild type |
| Streptococcus pneumoniae | ATCC 49619 | Intermediate susceptibility to Penicillin |

As above, a broth microdilution assay was used but the culture media were varied according to the specific growth requirements of each bacteria according to the recommendations of the NCCLS. For instance, susceptibility testing for H. influenzae was performed using Haemophilus test medium (HTM-Remel, cat. #20-042). For S. pneumoniae, cation adjusted MHB (CAMHB) containing 4% lysed horse blood was used. MICs were determined as described above. The result using a representative compound of this invention against this panel is shown in Table 6. As above, the compound shown in Table 6 and the result obtained are not to be construed as limiting the scope of this invention in any manner whatsoever.

TABLE 6

| | MIC (μg/ml) Broth microdilution | |
|---|---|---|
| Microorganism: | H. influenzae | S. pneumoniae |
| Compound Number 115 | 16 | >512 |

In a third panel, the antimicrobial activity of the compounds of this invention was tested against Mycobacteria (Table 7) again using the broth microdilution technique discussed above. Imipenem, ciprofloxacin and pacidamycin 4 were used as controls.

TABLE 7

| Bacteria | Strain | Characteristic |
|---|---|---|
| Mycobacterium smegmatis | ATCC 19420 | Recommended control |
| Mycobacterium fortuitum | ATCC 6841 | Recommended control, rifampicin-resistant |

In this panel, to promote growth of the bacteria, M. smegmatis and M. fortuitum were first streaked onto Lowenstein-Jensen slants and incubated at 37° C. for three days in an atmosphere of 95% air and 5% $CO_2$. The mycobacteria were then grown overnight (approximately 20 hours) at 35° C. in MHB supplemented with 0.02% Tween-80 to prevent clumping of newly formed cells. To prepare the inocula, the overnight cultures were diluted 1:1000 using CAMHB which gave inocula of approximately $10^5$ to $10^6$ CFU/ml. Microtiter plates were incubated for 72 hours at 35° C. and MICs were then determined as previously described. Results are shown in Table 8; the results and compounds shown are likewise not to be construed as limiting the scope of this invention in any manner.

TABLE 8

| | MIC (μg/ml) Broth microdilution | |
|---|---|---|
| Microorganism: | M. fortuitum ATCC 6841 | M. smegmatis ATCC19420 |
| Compound Number | | |
| 160 | 128 | 16 |
| 159 | 64 | 8 |
| 158 | 32 | 1 |
| 156 | 256 | 16 |
| 155 | 32 | 4 |
| 136 | 128 | 8 |
| 135 | 64 | 16 |
| 134 | 32 | 16 |
| 133 | 32 | 8 |
| 130 | 32 | 8 |
| 128 | 64 | 4 |
| 117 | 64 | 8 |

Finally, compounds of this invention were tested against a panel of Mycobacterium tuberculosis strains of differing susceptibility profiles to known anti-mycobacterial drugs (Table 9).

TABLE 9

| Bacteria | Strain | Characteristic |
|---|---|---|
| Mycobacterium tuberculosis | H37Rv | Susceptible to all anti-mycobacterial drugs |
| Mycobacterium tuberculosis | TN913 | Clinical isolates susceptible to all anti-mycobacterial drugs |
| Mycobacterium tuberculosis | TN565 | Clinical isolates, W strain, MDR* |
| Mycobacterium tuberculosis | TN1618 | Clinical isolates, P strain, MDR** |

*Multidrug resistant strain: resistant to rifampicin, isoniazid, ethambutol, streptomycin, ethionamide, ciprofloxacin, kanamycin
**Multidrug resistant strain: resistant to rifampicin, isoniazid, streptomycin, ethionamide, ciprofloxacin The antimicrobial activity against *M. tuberculosis* was tested using an agar dilution assay using Middlebrook 7H10 agar. Quadrant petri dishes were prepared with each quadrant containing agar with 0, 1, 10 and 30 µl/ml of the test compound (or control). Bacteria were inoculated on the surface of the agar and the appearance of colonies of bacteria was monitored during four weeks of incubation at 35° C. in an atmosphere of 95% Air and 5% $CO_2$. The MIC was recorded as the lowest concentration of compound which copntinued to prevent growth of the bacteria at the end of the incubation period. Results using several compounds of this invention are shown in Table 10. As before, the compounds shown and the results obtained are not to be construed as limiting the scope of this invention in any manner.

TABLE 10

| | MIC (µg/ml) | | | |
|---|---|---|---|---|
| Compound Number | H37RV (SENSITIVE) | TN913 (SENSITIVE) | TN565 (RESISTANT) | TN1618 (RESISTANT) |
| 164 | 10 | 10 | 10 | 10 |
| 159 | 30 | 30 | 30 | 10 |
| 158 | 10 | 10 | 10 | 10 |
| 157 | 10 | 10 | 10 | 10 |
| 146 | 10 | 10 | 10 | 10 |
| 155 | 10 | 10 | 10 | 10 |
| 133 | 30 | 30 | 30 | 10 |
| 115 | >30 | >30 | >30 | 30 |
| 109 | >30 | 30 | 10 | 10 |
| Pacidamycin 4 | >30 | >30 | >30 | >30 |

Conclusion

Thus, it will be appreciated that the compounds, methods and pharmaceutical compositions of the present invention are effective as antibacterial compounds particularly against several bacterial strains which are resistant to currently employed therapeutic antibiotics.

One skilled in the art would readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. Al]patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.
What is claimed is:
1. A compound having the chemical structure:

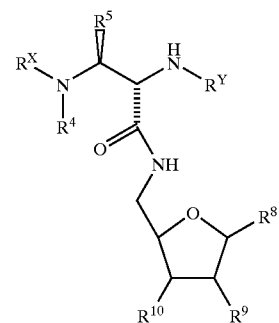

wherein,
R and R' are independently selected from the group consisting of hydrogen, alkyl, alkenyl, alkynyl, aryl, heteroaryl, heteroalicyclic, —C(=O)R", —C(=O)OR" and R"C(=O)O—, R" being selected from the group consisting of hydrogen, alkyl, cycloalkyl, aryl, heteroaryl (bonded through a ring carbon) and heteroalicyclic (bonded through a ring carbon).
2. The compound of claim 1, wherein said compound inhibits growth of bacteria.
3. The compound of claim 2, wherein said inhibition is selective.
4. The compound of claim 3, wherein said selective inhibition comprises inhibition of bacterial translocase I.

5. The compound of claim 2, wherein said bacteria are selected from the group consisting of Pseudomonas, Escherichia, Staphylococcus, Streptococcus, Enterococcus, Mycobacteria and Haemophilus.

6. A compound having the chemical structure:

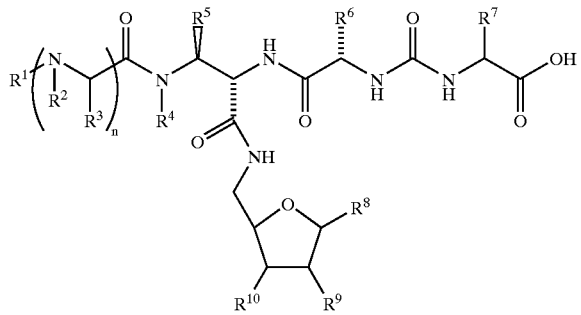

wherein,

- $R^1$ and $R^2$ are independently selected from the group consisting of hydrogen, alkyl, cycloalkyl, alkenyl, alkynyl, aryl, heteroaryl, heteroalicyclic, —C(=O)R", —S(=O)$_2$R", X$_3$CS(=O)$_2$R", —C(=O)OR", R"C(=O)O—, —C(=O)NRR', cyano, hydroxy, alkoxy, —NRR', amino acid, peptide of 2–4 amino acid residues, or, $R^1$ and $R^2$, taken together with the nitrogen atom to which they are bonded, form a heteroaryl or a heteroalicyclic, or $R^1$ or $R^2$, with the nitrogen to which it is bonded, combined with $R^3$, forms a heteroaryl, a heteroalicyclic, a heteroaryl/aryl bicyclic, a heteroalicyclic/aryl bicyclic, a heteroaryl/heteroaryl bicyclic or a heteroalicyclic/heteroaryl bicyclic;
- $R^3$ is selected from the group consisting of hydrogen, optionally substituted alkyl, cycloalkyl, alkenyl, alkynyl, aryl, heteroaryl, heteroalicyclic, —C(=O)OR", —C(=O)NRR' and, combined with $R^1$ or $R^2$, with the nitrogen to which $R^1$ or $R^2$ is bonded, a heteroaryl, a heteroalicyclic, a heteroaryl/aryl bicyclic, a heteroalicyclic/aryl bicyclic, a heteroaryl/heteroaryl bicyclic or a heteroalicyclic/heteroaryl bicyclic;
- $R^4$ and $R^5$ are independently selected from the group consisting of hydrogen, alkyl, alkenyl, alkynyl, aryl and heteroaryl;
- $R^6$ and $R^7$ are independently selected from the group consisting of hydrogen, optionally substituted alkyl, cycloalkyl, alkenyl, alkynyl, aryl, heteroaryl, heteroalicyclic, —C(=O)OR" and —C(=O)NRR';
- $R^8$ is uracil or dihydrouracil optionally substituted with a group selected from the group consisting of alkyl, alkenyl, alkynyl, aryl, heteroaryl, heteroalicyclic, halo, cyano, nitro and —NRR';
- $R^9$ and $R^{10}$ are independently selected from the group consisting of hydrogen, halo, cyano, hydroxy, alkoxy, mercapto, alkylthio and —NRR';
- n is 0 or 1;
- R and R' are independently selected from the group consisting of hydrogen, alkyl, cycloalkyl, alkenyl, alkynyl, aryl, —C(O)R", S(=O)$_2$R", and, combined, a five-member or a six-member heteroalicyclic ring; and,
- R" is selected from the group consisting of hydrogen, alkyl, cycloalkyl, aryl, heteroaryl (bonded through a ring carbon) and heteroalicyclic (bonded through a ring carbon).

7. The compound of claim 6, wherein
- n is 1; and,
- $R^1$ and $R^2$ are independently selected from the group consisting of hydrogen, dipeptidyl, tripeptidyl, tetrapeptidyl and, combined with $R^3$, a heteroalicyclic/aryl bicyclic or a heteroalicyclic/heteroaryl bicyclic.

8. The compound of claim 7, wherein $R^3$ is selected from the group consisting of hydrogen, lower alkyl, monocyclic aryl, bicyclic aryl and, combined with $R^2$ a heteroalicyclic/aryl bicyclic or a heteroalicyclic/heteroaryl bicyclic.

9. The compound of claim 8, wherein $R^4$ and $R^5$ are independently selected from the group consisting of hydrogen and alkyl.

10. The compound of claim 9, wherein $R^6$ and $R^7$ are independently selected from the group consisting of hydrogen, lower alkyl, monocyclic aryl and bicyclic aryl.

11. The compound of claim 10, wherein $R^8$ is uracil or dihydrouracil optionally substituted with a group selected from the group consisting of lower alkyl, lower alkenyl, lower alkynyl, halo, cyano, nitro and NRR' wherein R and R' are independently selected from th group consisting of hydrogen and lower alkyl.

12. The compound of claim 11, wherein $R^9$ is selected from the group consisting of hydrogen, halo, hydroxy, lower alkoxy, mercapto and (lower alkyl)thio.

13. The compound of claim 12, wherein $R^{10}$ is selected from the group consisting of hydrogen and hydroxy.

14. The compound of claim 6, wherein
- n is 1; and,
- $R^1$ and $R^2$ are independently selected from the group consisting of hydrogen, dipeptidyl, and combined with $R^3$, a heteroalicyclic/aryl bicyclic.

15. The compound of claim 14, wherein $R^3$ is selected from the group consisting of
- hydrogen;
- lower alkyl optionally substituted with a group selected from the group consisting of (loweralky)thio, —NH$_2$ and optionally substituted aryl and, combined with $R^2$, six-member heteroalicyclic/six-member aryl bicyclic.

16. The compound of claim 15, wherein $R^4$ and $R^5$ are independently selected from the group consisting of hydrogen and lower alkyl.

17. The compound of claim 16, wherein $R^6$ and $R^7$ are independently selected from the group consisting of
- hydrogen; and,
- lower alkyl optionally substituted with a group selected from the group consisting of (lower alky)thio, —NH$_2$, optionally substituted aryl and heteroaryl.

18. The compound of claim 17, wherein $R^8$ is uracil or dihydrouracil optionally substituted with a group selected from the group consisting of lower alkyl, lower alkenyl and halo.

19. The compound of claim 18, wherein $R^9$ is selected from the group consisting of hydrogen, halo and hydroxy.

20. The compound of claim 19, wherein $R^{10}$ is selected from the group consisting of hydrogen and hydroxy.

21. The compound of claim 6, wherein:
- n is 1;
- $R^1$ and $R^2$ are both hydrogen or $R^1$ is hydrogen and $R^2$ is combined with $R^3$ to form a 6-hydroxytetrahydroisoquinolin-3-yl or 1-methyl-6-hydroxytetrahydroisoquinoline-3-yl:

$R^3$ is selected from the group consisting of:
  hydrogen,
  lower alkyl optionally substituted with a group selected from the group consisting of:
    hydroxy,
    mercapto,
    lower alkoxy,
    (lower alkyl)thio,
    halo,
    —NRR',
  aryl, optionally substituted with one or more groups selected from the group consisting of:
    lower alkyl,
    trihalomethyl,
    hydroxy,
    lower alkoxy,
    (lower alkyl)thio,
    halo,
    nitro and
    —NRR'; and,
  combined with $R^2$, 6-hydroxyisoquinolin-3-yl or 1-methyl-6-hydroxyisoquinoline-3-yl;
$R^4$ and $R^5$ are methyl;
$R^6$ is selected from the group consisting of:
  lower alkyl optionally substituted with a group selected from the group consisting of:
    hydroxy,
    lower alkoxy,
    (lower alkyl)thio,
    halo,
    —NRR',
  cyclohexyl,
  aryl, optionally substituted with one or more groups selected from the group consisting of:
    hydroxy,
    lower alkoxy,
    (lower alkyl)thio,
    halo,
    trihalomethyl,
    nitro,
    —NRR',
    and phenyl, and,
  heteroaryl, optionally substituted with one or more groups selected from the group consisting of hydroxy, lower alkoxy, (lower alkyl)thio, halo, trihalomethyl, nitro, —NRR', and phenyl;
$R^7$ is selected from the group consisting of:
  lower alkyl optionally substituted with a group selected from the group consisting of:
    aryl, optionally substituted with one or more groups selected from the group consisting of:
      hydroxy,
      lower alkoxy,
      (lower alkyl)thio,
      halo,
      trihalomethyl,
      nitro,
      —NRR' and
      phenyl;
    heteroaryl, optionally substituted with one or more groups selected from the group consisting of:
      hydroxy,
      lower alkoxy,
      (lower alkyl)thio,
      halo,
      trihalomethyl,
      nitro,
      —NRR' and
      phenyl, and
    aryl, optionally substituted with one or more groups selected from the group consisting of hydroxy, lower alkoxy, (lower alkyl)thio, halo, trihalomethyl, nitro, —NRR' and phenyl;
$R^8$ is uracil or dihydrouracil;
$R^9$ is hydroxy;
$R^{10}$ is hydrogen; and,
R and R' are independently selected from the group consisting of hydrogen and lower alkyl.

22. The compound of claim 21, wherein said aryl group is phenyl or naphthyl.

23. The compound of claim 21, wherein said heteroaryl group is selected from the group consisting of indol-3-yl, thien-2-yl, benzothien-3-yl, thiazol-4-yl, imidazol-2-yl and imidazol-4-yl.

24. The compound of claim 6, wherein
  n is 0; and,
  $R^1$ is selected from the group consisting of
    lower alkyl substituted with one or more groups selected from the group consisting of
      —NRR',
      N-piperazinyl,
      aryl substituted with one or more groups selected from group consisting of
        —NRR' and
        lower alkyl substituted with one or more —NRR' groups; and,
  R and R' are independently selected from the group consisting of hydrogen and lower alkyl.

25. A compound selected from the group consisting of:

1-[5'-[(2S,3S)-N²-[N-[[(1S)-1-Carboxy-4-hydroxyphenethyl]carbamoyl]-L-phenylalanyl]-N³-L-phenylalanyl-N³-methyl-2,3-diaminobutyramido]-3',5'-dideoxy-α-L-arabinofuranosyl]uracil (Compound 100), 1-[5'-[(2S,3S)-N²-[N-[[(1S)-1-Carboxy-4-hydroxyphenethyl]carbamoyl]-L-phenylalanyl]-N³-L-leucyl-N³-methyl-2,3-diaminobutyramido]-3,5-dideoxy-α-L-arabinofuranosyl]uracil (Compound 101), 1-[5'-[(2S,3S)-N²-[N-[[(1S)-1-Carboxy-4-hydroxyphenethyl]carbamoyl]-L-phenylalanyl]-N³-glycyl-N³-methyl-2,3-diaminobutyramido]-3',5'-dideoxy-α-L-arabinofuranosyl]uracil (Compound 102), 1-[5'-[(2S,3S)-N²-[N-[[(1S)-1-Carboxy-2-indol-3-ylethyllcarbamoyl]-L-alanyl]-N³-L-3-hydroxyphenylalanyl-N³-methyl-2,3-diaminobutyramidol-3',5'-dideoxy-α-L-arabinofuranosyl]uracil (Compound 103), 1-[5'[(2S,3S)-N²-[N-[[(1S)-1-Carboxy-4-hydroxyphenethyl]carbamoyl]-L-methionyl]-N³-glycyl-N³-methyl-2,3-diaminobutyramidol-3',5'-dideoxy-α-L-arabinofuranosyl]uracil (Compound 104), 1-[5'[(2S,3S)-N²-[N-[[(1S)-1-Carboxy-4-hydroxyphenethyl]carbamoyl]-L-4-fluorophenylalanyl]-N³-L-4-fluorophenylalanyl-N³-methyl-2,3-diaminobutyramido]-3',5'-dideoxy-α-L-arabinofuranosyl]uracil (Compound 105), 1-[5'[(2S,3S)-N²-[N-[[(1S)-1-Carboxy-4-hydroxyphenethyl]carbamoyl]-L-4-fluorophenylalanyl)-N³-L-phenylalanyl-N³-methyl-2,3-diaminobutyramido]-3',5'-dideoxy-α-L-arabinofuranosyl]uracil (Compound 106), 1-[5'[(2S,3S)-N²-[N-[[((1S)-1-Carboxy-4-hydroxyphenethyl]carbamoyl]-L-4-fluorophenylalanyl]-

N³-L-leucyl-N³-methyl-2,3-diaminobutyramido]-3',5'-dideoxy-α-L-arabinofuranosyl]uracil (Compound 107), 1-[5'[(2S,3S)-N²-[N-[[(1S)-1-Carboxy-2-indol-3-ylethyl]carbamoyl]-L-leucyl]-N³-L-leucyl-N³-methyl-2,3-diaminobutyramido]-3',5'-dideoxy-α-L-arabinofuranosyl]uracil (Compound 108), 1-[5'-[(2S,3S)-N²-[N-[[(1S)-1-Carboxy-2-indol-3-ylethyl]carbamoyl]-L-leucyl]-N³-glycyl-N³-methyl-2,3-diaminobutyramido]-3',5'-dideoxy-α-L-arabinofuranosyl]uracil (Compound 109), 1-[5'-[(2S,3S)-N²-[N-[[(1S)-1-Carboxy-2-indol-3-ylethyl]carbamoyl]-L-methionyl]-N³-L-4-fluorophenylalanyl-N³-methyl-2,3-diaminobutyramido]-3',5'-dideoxy-α-L-arabinofuranosyl]uracil (Compound 110), 1-[5'-[(2S,3S)-N²-[N-[[(1S)-1-Carboxy-2-indol-3-ylethyl]carbamoyl]-L-methionyl]-N³-L-phenylalanyl-N³-methyl-2,3-diaminobutyramido]-3',5'-dideoxy-α-L-arabinofuranosyl]uracil (Compound 111), 1-[5'-[(2S,3S)-N²-[N-[[(1S)-1-Carboxy-2-indol-3-ylethyl]carbamoyl]-L-methionyl]-N³-glycyl-N³-methyl-2,3-diaminobutyramido]-3',5'-dideoxy-α-L-arabinofuranosyl]uracil (Compound 112), 1-[S-[(2S,3S)-[N-[[(1S)-1-Carboxy-2-indol-3-ylethyl]carbamoyl]-L-4-fluorophenylalanyl]-N³-L-phenylalanyl-N³-methyl-2,3-diaminobutyramido]-3,5-dideoxy-α-L-arabinofuranosyl]uracil (Compound 113), 1-[5-((2S,3S)-N²-[N-[[(1S)-1-Carboxy-2-indol-3-ylethyl]carbamoyl]-L-phenylalanyl]-N³-L-4-fluorophenylalanyl-N³-methyl-2,3-diaminobutyramido]-3,5-dideoxy-α-L-arabinofuranosyl]uracil (Compound 114), 1-[5'[(2S,3S)-N³-L-Alanyl-N²-[N-[[(1S)-1-carboxy-4-hydroxyphenethyl]carbamoyl]-L-methionyl]-N³-methyl-2,3-diaminobutyramido]-3',5'-dideoxy-α-L-arabinofuranosyl](Compound 115), 1-[5'-[(2S,3S)-N²-[N-[[(1S)-1-Carboxy-2-indol-3-ylethyl]carbamoyl]-L-4-fluorophenylalanyl]-N³-glycyl-N³-methyl-2,3-diaminobutyramido]-3',5'-dideoxy-α-L-arabinofuranosyl]uracil (Compound 116), 1-[5'-[(2S,3S)-N²-[N-[[(1S)-1-Carboxy-2-indol-3-ylethyl]carbamoyl]-L-4-fluorophenylalanyl]-N³-L-leucyl-N³-methyl-2,3-diaminobutyramido]-3',5'-dideoxy-α-L-arabinofuranosyl]uracil (Compound 117), 1-[5'-[(2S,3S)-N²-[N-[[(1S)-1-Carboxy-2-indol-3-ylethyl]carbamoyl]-L-4-fluorophenylalanyl]-N³-L-4-fluorophenylalanyl-N³-methyl-2,3-diaminobutyramido]-3',5'-dideoxy-α-L-arabinofuranosyl]uracil (Compound 118), 1-[5'-[(2S,3S)-N³-L-Alanyl-N²-[N-[[(1S)-1-Carboxy-4-hydroxyphenethyl]carbamoyl]-L-3-(2-thienyl)alanyl]-N³-methyl-2,3-diaminobutyramido]-3',5'-dideoxy-α-L-arabinofuranosyl]uracil (Compound 119), 1-[5'-[(2S,3S)-N²-[N-[[(1S)-1-Carboxy-4-hydroxyphenethyl]carbamoyl]-L-leucyl]-N³-glycyl-N³-methyl-2,3-diaminobutyramido]-3',5'-dideoxy-α-L-arabinofuranosyl]uracil (Compound 120), 1-[5'-[(2S,3S)-N²-[N-[[(1S)-1-Carboxy-2-indol-3-ylethyl]carbamoyl]-L-alanyl]-N³-glycyl-N³-methyl-2,3-diaminobutyramido]-3',5'-dideoxy-α-L-arabinofuranosyl]uracil (Compound 121), 1-[5'-[[(2S,3S)-L-Alanyl-N²-[N-[[(1S)-1-carboxy-phenethyl]carbamoyl]-L-phenylalanyl]-N³-methyl-2,3-diaminobutyramido]-3',5'-dideoxy-α-L-arabinofuranosyl]uracil (Compound 122), 1-[5'-[(2S,3S)-N³-5-Aminopentanoyl-N²-[N-[[(1S)-1-carboxy-2-indol-3-ylethyl]carbamoyl]-L-phenylalanyl]-N³-methyl-2,3-diaminobutyramido]-3',5'-dideoxy-α-L-arabinofuranosyl]uracil (Compound 123), 1-[5'-[(2S,3S)-N³-5-Aminopentanoyl-N²-[N-[[(1S)-1-Carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 124), 1-[5'-[(2S,3S)-N³-L-Alanyl-N²-[N-[[(1S)-1-carboxy-2-(2-thienyl)ethyl]carbamoyl]-L-phenylalanyl]-N³-methyl-2,3-diaminobutyramido]-3',5'-dideoxy-α-L-arabinofuranosyl]uracil (Compound 125), 1-[5'-[(2S,3S)-N³-L-Alanyl-N²-[N-[[(1S)-1-carboxy-4-hydroxyphenethyl]carbamoyl]-L-4-nitrophenylalanyl]-N³-methyl-2,3-diaminobutyramido]-3',5'-dideoxy-α-L-arabinofuranosyl]uracil (Compound 126), 1-[5'-[(2S,3S)-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 127), 1-[5'-[(2S,3S)-N²-[N-[[(1S)-1-Carboxy-2-indol-3-ylethyl]carbamoyl]-L-phenylalanyl]-N³-glycyl-N³-methyl-2,3-diaminobutyramido]-3',5'-dideoxy-α-L-arabinofuranosyl]uracil (Compound 128), 1-[5'-[(2S,3S)-N²-[N-[[(1S)-1-carboxy-4-hydroxyphenethyl]carbamoyl]-L-4-fluorophenylalanyl]-N³-glycyl-N³-methyl-2,3-diaminobutyramido]-3',5'-dideoxy-α-L-arabinofuranosyl]uracil (Compound 129), 1-[5'-[(2S,3S)-N³-L-alanyl-N²-[N-[[(1S)-1-carboxy-4-hydroxyphenethyl]carbamoyl]-L-benzothiophenylalanyl]-N³-methyl-2,3-diaminobutyramido]-3',5'-dideoxy-α-L-arabinofuranosyl]uracil (Compound 130), 1-[5'-[(2S,3S )-N³-3-Aminobenzoyl-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 131), 1-[5'-[(2S,3S)-N³-L-Alanyl-N²-[N-[[(1S)-1-carboxy-4-hydroxyphenethyl]carbamoyl]-L-thiazolylalanyl]-N³-methyl-2,3-diaminobutyramido]-3',5'-dideoxy-α-L-arabinofuranosyl]uracil (Compound 132), 1-[5'-[(2S,3S)-N³-L-Alanyl-N²-[N-[[(1S)-1-carboxy-3-naphtenethyl]carbamoyl]-L-phenylalanyl]-N³-methyl-2,3-diaminobutyramido]-3',5'-dideoxy-α-L-arabinofuranosyl]uracil (Compound 133), 1-[5'-[(2S,3S)-N³-L-Alanyl-N²-[N-[[(1S)-1-carboxy-4-hydroxyphenethyl]carbamoyl]-L-4-iodophenylalanyl]-N³-methyl-2,3-diaminobutyramido]-3',5'-dideoxy-α-L-arabinofuranosyl]uracil (Compound 134), 1-[5'-[(2S,3S)-N³-L-Alanyl-N²-[N-[[(1S)-1-carboxy-4-hydroxyphenethyl]carbamoyl]-L-4-chlorophenylalanyl]-N³-methyl-2,3-diaminobutyramido]-3',5'-dideoxy-α-L-arabinofuranosyl]uracil (Compound 135), 1-[5'-[(2S,3S)-N³-L-Alanyl-N²-[N-[[(1S)-1-carboxy-2-indol-3-carbamoyl]-L-cyclohexylalanyl]-N³-methyl-2,3-diaminobutyramido]-3',5'-dideoxy-α-L-arabinofuranosyl]uracil (Compound 136), 1-[5'-[(2S,3S)-N³-L-Alanyl-N²-[N-[[(1S)-1-carboxy-4-hydroxyphenethyl]carbamoyl]-L-homophenylalanyl]-N³-methyl-2,3-diaminobutyramido]-3',5'-dideoxy-α-L-arabinofuranosyl]uracil (Compound 137), 1-[5'-[(2S,3S)-N³-L-Alanyl-N²-[N-[[(1S)-1-carboxy-2-indol-3-ylethyl]carbamoyl]-L-homophenylalanyl]-N³-methyl-2,3-diaminobutyramido]-3',5'-dideoxy-α-L-arabinofuranosyl]uracil (Compound 138), 1-[S-[(2S,3S)-N³-L-Alanyl-N²-[N-[[(1S)-1-carboxy-2-indol-3-ylethyl]carbamoyl]-L-2-fluorophenylalanyl]-N³-methyl-2,3-diaminobutyramido]-3,5-dideoxy-α-L-arabinouranosyl]uracil (Compound 139), 1-[5-[(2S,3S)-N³-L-Alanyl-N²-[N-[[(1S)-1-carboxy-4-hydroxyphenethyl]carbamoyl]-L-2-fluorophenylalanyl]-N³-methyl-2,3-diaminobutyramido]-3,5-dideoxy-α-L-arabinofuranosyl]uracil (Compound 140), 1-[5'-[(2S,3S)-N³-L-Alanyl-N²-[N-[[α(R,S)-1-carboxyphenylmethyl]carbamoyl]-L-4-fluorophenylalanyl]-N³-methyl-2,3-diaminobutyramido]-3',5'-dideoxy-α-L-arabinofuranosyl!]uracil (Compound 141), 1-[5'-[(2S,3S)-N³-L-Alanyl-N²-[N-[[α(S,R)-1-carboxyphenylmethyl]carbamoyl]-L-4-fluorophenylalanyl]-N³-methyl-2,3-diaminobutyramido]-3',5'-dideoxy-α-L-arabinofuranosyl]uracil (Compound 142), 1-[5'-[(2S,3S)-N³-L-Alanyl-N²-[N-[[(1S)-1-carboxy-2-indol-3-ylethyl]carbamoyl]-L-(3,4)-difluorophenylalanyl]-N³-methyl-2,3-diaminobutyramido]-3',5'-dideoxy-α-L-arabinofuranosyl]uracil (Compound 143), 1-[5'-[(2S,3S)-N³-L-Alanyl-N²-[N-[[(1S)-1-carboxy-4hydroxyphenethyl]carbamoyl]-L-(3,4)-difluorophenylalanyl]-N³-methyl-2,3-diaminobutyramido]-3',5'-dideoxy-α-L-arabinofuranosyl]uracil (Compound 144), 1-[5'-[(2S,3S)-N³-L-Alanyl-N²-[N-[[(1S)-1-carboxy-4-hydroxyphenethyl]carbamoyl]-L-4-(trifluoromethyl)-phenylalanyl]-N³-methyl-2,3-diaminobutyramido]-3',5'-dideoxy-α-L-arabinofuranosyl]uracil (Compound 145), 1-[5'-[(2S,3S)-N³-L-Alanyl-N²-[N-[[(1S)-1-carboxy-2-indol-3-ylethyl]carbamoyl]-L-4-(trifluoromethyl)phenylalanyl]-N³-methyl-2,3-diaminobutyramido]-3',5'-dideoxy-α-L-arabinofuranosyl]uracil (Compound 146), 1-[5'-[(2S,3S)-N²-[N-[[(1S)-1-Carboxy-2-indol-3-ylethyl]carbamoyl]-L-phenylalanyl]-N³-L-lysinyl-N³-methyl-2,3-diaminobutyramido]-3',5'-dideoxy-α-L-arabinofuranosyl]uracil (Compound 147), 1-[5'-[(2S,3S)-N³-L-Alanyl-N²[N-[[(1S)-1-carboxy-2-indol-3-ylethyl]carbamoyl]-L-lysinyl]-N³-methyl-2,3-diaminobutyramido]-3',5'-dideoxy-α-L-arabinofuranosyl]uracil (Compound 148), 1-[5'-[(2S,3S)-N³-L-Alanyl-N²-[N-[[(1S)-1-carboxy-5-imidazylethyl]carbamoyl]-L-phenylalanyl]-N³-methyl-2,3-diaminobutyramido]-3',5'-dideoxy-α-L-arabinofuranosyl]uracil (Compound 149), 1-[5'-[(2S,3S)-N³-(L-O-Benzylserinyl)-N²-[N-[[(1S)-1-carboxy-4-hydroxyphenethyl]carbamoyl]-L-phenylalanyl]-N³-methyl-2,3-diaminobutyramido]-3',5'-dideoxy-α-L-arabinofuranosyl]uracil (Compound 150), 1-[5'-[(2S,3S)-N²-[N-[[(1S)-1-Carboxy-2-indol-3-ylethyl]carbamoyl]-L-phenylalanyl]-N³-methyl-2,3-diaminobutyramido]-3',5'-dideoxy-α-L-arabinofuranosyl]uracil (Compound 151), 1-[5'-[(2S,3S)-N³-L-Alanyl-N²-[N-[[(1S)-1-carboxy-4-hydroxyphenethyl]carbamoyl]-L-3-(2-naphthyl)alanyl]-N³-methyl-2,3-diaminobutyramido]-3',5'-dideoxy-α-L-arabinofuranosyl]uracil (Compound 152), 1-[5'-[(2S,3S)-N³-L-Alanyl-N²-[N-[[(1S)-1-carboxy-2-indol-3-ylethyl]carbamoyl]-L-3-(2-naphthyl)alanyl]-N³-methyl-2,3-diaminobutyramido]-3',5'-dideoxy-α-L-arabinofuranosyl]uracil (Compound 153), 1-[5'-[(2S,3S)-N³-L-Alanyl-N²-[N-[[(1S)-1-carboxy-2-indol-3-ylethyl]carbamoyl]-L-phenylalanyl]-N³-methyl-2,3-diaminobutyramido]-3',5'-dideoxy-α-L-arabinofuranosyl]uracil (Compound 154), 1-[5'-[(2S,3S)-N³-L-Alanyl-N²-[N-[[(1S)-1-carboxy-2-indol-3-ylethyl]carbamoyl]-L-4-biphenylalanyl]-N³-methyl-2,3-diaminobutyramido]-3',5'-dideoxy-α-L-arabinofuranosyl]uracil (Compound 155), 1-[5'-[(2S,3S)-N²-[N-[[(1S)-1-Carboxy-2-indol-3-ylethyl]carbamoyl]-L-phenylalanyl]-N³-L-phenylalanyl-N³-methyl-2,3-diaminobutyramido]-3',5'-dideoxy-α-L-arabinofuranosyl]uracil (Compound 156), 1-[5'-[(2S,3S)-N³-L-Alanyl-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 157), 1-[5'-[(2S,3S)-N³-L-Alanyl-N²-[N-[[(1S)-1-carboxy-2-indol-3-ylethyl]carbamoyl]-L-4-fluorophenylalanyl]-N³-methyl-2,3-diaminobutyramido]-3',5'-dideoxy-α-L-arabinofuranosyl]uracil (Compound 158), 1-[5'-[(2S,3S)-N²-[N-[[(1S)-1-Carboxy-2-indol-3-ylethyl]carbamoyl]-L-phenylalanyl]l-N³-L-leucyl-N³-methyl-2,3-diaminobutyramido]-3',5'-dideoxy-α-L-arabinofuranosyl]uracil (Compound 159), 1-[5'-[(2S,3S)-N³-L-Alanyl-N²-[N-[[(1S)-1-carboxy-4-hydroxyphenethyl]carbamoyl]-L-phenylalanyl]-N³-methyl-2,3-diaminobutyramido]-3',5'-dideoxy-α-L-arabinofuranosyl]uracil (Compound 160), 1-[5'-[(2S,3S)-N³-L-Alanyl-N²-[N-[[(1S)-1-carboxy-4-hydroxyphenethyl]carbamoyl]-L-leucyl]-N³-L-methyl-2,3-diaminobutyramido]-3',5'-dideoxy-α-L-arabinofuranosyl]uracil (Compound 161), 1-[5'-[(2S,3S)-N²-[N-[[(1S)-1-Carboxy-2-indol-3-ylethyl]carbamoyl]-L-methionyl]-N³-L-methionyl-N³-methyl-2,3-diaminobutyramido]-3',5'-dideoxy-α-L-arabinofuranosyl]uracil (Compound 162), 1-[5'-[(2S,3S)-N²-[N-[[(1S)-1-Carboxy-2-indol-3-ylethyl]carbamoyl]-L-phenylalanyl]-N³-L-tyrosyl-N³-methyl-2,3-diaminobutyramido]-3',5'-dideoxy-α-L-arabinofuranosyl]uracil (Compound 163), 1-[5'-[(2S,3S)-N³-L-Alanyl-N²-[N-[[(1S)-1-carboxy-2-indol-3-ylethyl]carbamoyl]-L-phenylalanyl]-N³-methyl-2,3-diaminobutyramido-3',5'-dideoxy-α-L-arabinofuranosyl]uracil (Compound 164), 1-5'-[(2S,3S)-N²-[N-[[(1S)-1-Carboxy-2-indol-3-ylethyl]carbamoyl]-L-alanyl]-N³-methyl-2,3-diaminobutyramido]-3',5'-dideoxy-α-L-arabinofuranosyl]uracil (Compound 165), 1-[5'-[(2S,3S)-N³-L-Alanyl-N²-[N-([(1S)-1-carboxy-2-indol-3-ylethyl]carbamoyl]-L-leucinyl]-N³-methyl-2,3-diaminobutyramido]-3',5'-dideoxy-α-L-arabinofuranosyl]uracil (Compound 166), 1-[5'-[(2S,3S)-N³-L-Alanyl-N²-[N-[[(1S)-1-carboxyphenethyl]carbamoyl]-L-methionyl]-N³-methyl-2,3-diaminobutyramido]-3',5'-dideoxy-α-L-arabinofuranosyl]uracil (Compound 167), 1-5'-[(2S,3S)-N²-[N-[[(1S)-1-Carboxy-2-indol-3-ylethyl]carbamoyl]-L-alanyl]-N³-L-methionyl-N³-methyl-2,3-diaminobutyramido]-3',5'-dideoxy-α-L-arabinofuranosyl]uracil (Compound 168), 1-[5'-[(2S,3S)-N³-L-Alanyl-N²-[N-[[(1S)-1-carboxy-2-indol-3-ylethyl]carbamoyl]-L-valinyl]-N³-methyl-2,3-diaminobutyramido]-3',5'-dideoxy-α-L-arabinofuranosyl]uracil (Compound 169), 1-[5'-[(2S,3S)-N³-L-Alanyl-N²-[N-[[(1S)-1-carboxy-2-indol-3-ylethyl]carbamoyl]-L-leucinyl]-N³-methyl-2,3-diaminobutyramido]-3',5'-dideoxy-α-L-arabinofuranosyl]uracil (Compound 170), 1-[5'-[(2S,3S)-N³-D-Alanyl-N²-[N-[[(1S)-1-carboxy-2-indol-3-ylethyl]carbamoyl]-L-alanyl]-N³-methyl-2,3-diaminobutyramido]-3',5'-dideoxy-α-L-arabinofuranosyl]uracil (Compound 171), and 1-[5'-[(2S,3S)-N³-L-Alanyl-N²-[N-[[(1S)-1-Carboxy-2-indol-3-ylethyl]carbamoyl]-L-alanyl]-N³-methyl-2,3-diaminobutyramido]-3',5'-dideoxy-β-D-ribofuranosyl]uracil (Compound 172).

26. A composition comprising
a compound of any one of claims 1, 6, or 25; and,
a physiologically acceptable carrier.

27. A method for synthesizing a compound of formula I, comprising reacting a compound of formula II with molecular hydrogen in the presence of a hydrogenation catalyst and a solvent for a time and under conditions effective to reduce a carbon-carbon double bond in the compound of formula II, wherein the compound of formula II has the chemical structure:

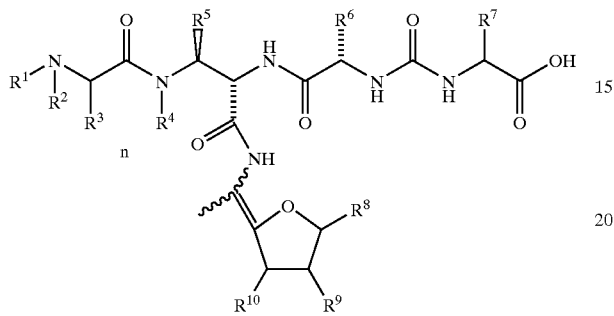

wherein:
R$^1$ and R$^2$ are independently selected from the group consisting of hydrogen, alkyl, cycloalkyl, aryl, heteroaryl, heteroalicyclic, —C(=O)R", —C(=O)OR", R"C(=O)O—, —C(=O)NRR', cyano, hydroxy, alkoxy, —NRR', amino acid, a peptide of 2–4 amino acid residues and, R$^1$ and R$^2$, taken together with the nitrogen atom to which they are bonded, form a heteroaryl or a heteroalicyclic, or R$^1$ or R$^2$, taken with the nitrogen atom to which it is bonded, combined with R$^3$, forms a heteroaryl, a heteroalicyclic, a heteroaryl/aryl bicyclic, a heteroalicyclic/aryl bicyclic, a heteroaryl/heteroaryl bicyclic or a heteroalicyclic/heteroaryl bicyclic;

R$_3$ is selected from the group consisting of hydrogen, alkyl, cycloalkyl, aryl, heteroaryl, heteroalicyclic, —C(=O)OR", —C(=O)NRR' and, combined with R$^1$ or R$^2$, with the nitrogen to which R$^1$ or R$^2$ is bonded, forms a heteroalicyclic, a heteroaryl/aryl bicyclic, a heteroalicyclic/aryl bicyclic, a heteroaryl/heteroaryl bicyclic and a heteroalicyclic/heteroaryl;

R$^4$ and R$^5$ are independently selected from the group consisting of hydrogen, alkyl, aryl and heteroaryl;

R$^6$ and R$^7$ are independently selected from the group consisting of hydrogen, alkyl, cycloakyl, aryl, heteroaryl, heteroalicyclic, —C(=O)OR", —C(=O)NRR';

R$^8$ is uracil or dihydrouracil optionally substituted with a group selected from the group consisting of alkyl, aryl, heteroaryl, heteroalicyclic, halo, cyano, nitro and —NRR';

R$^9$ and R$^{10}$ are selected from the group consisting of hydrogen, halo, cyano, hydroxy, lower alkoxy and —NRR';

n is 0 or 1;

R and R' are independently selected from the group consisting of hydrogen, alkyl, cycloakyl, aryl, —C(=O)R" and, combined, a five-member or a six-member heteroalicyclic; and, R" is selected from the group consisting of hydrogen, alkyl, cycloalkyl, aryl, heteroaryl (bonded through a ring carbon) and heteroalicyclic (bonded through a ring carbon); and, isolating the compound of formula I, which has the chemical structure:

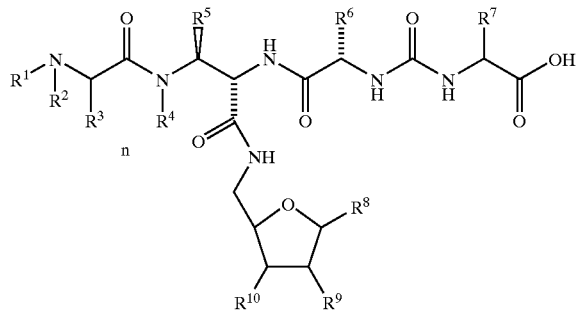

wherein:
R$^1$ and R$^2$ are independently selected from the group consisting of hydrogen, alkyl, cycloalkyl, aryl, heteroaryl, heteroalicyclic, —C(=O)R", —C(=O)OR", R"C(=O)O—, —C(=O)NRR', cyano, hydroxy, alkoxy, —NRR', amino acid, a peptide of 2–4 amino acid residues and, R$^1$ and R$^2$, taken together with the nitrogen atom to which they are bonded, form a heteroaryl or a heteroalicyclic, or R$^1$ or R$^2$, taken with the nitrogen atom to which it is bonded, combined with R$^3$, forms a heteroaryl, a heteroalicyclic, a heteroaryl/aryl bicyclic, a heteroalicyclic/aryl bicyclic, a heteroaryl/heteroaryl bicyclic or a heteroalicyclic/heteroaryl bicyclic;

R$_3$ is selected from the group consisting of hydrogen, alkyl, cycloalkyl, aryl, heteroaryl, heteroalicyclic, —C(=O)OR", —C(=O)NRR' and, combined with R$^1$ or R$^2$, with the nitrogen to which R$^1$ or R$^2$ is bonded, forms a heteroalicyclic, a heteroaryl/aryl bicyclic, a heteroalicyclic/aryl bicyclic, a heteroaryl/heteroaryl bicyclic and a heteroalicyclic/heteroaryl;

R$^4$ and R$^5$ are independently selected from the group consisting of hydrogen, alkyl, aryl and heteroaryl;

R$^6$ and R$^7$ are independently selected from the group consisting of hydrogen, alkyl, cycloakyl, aryl, heteroaryl, heteroalicyclic, —C(=O)OR", —C(=O)NRR';

R$^8$ is uracil or dihydrouracil optionally substituted with a group selected from the group consisting of alkyl, aryl, heteroaryl, heteroalicyclic, halo, cyano, nitro and —NRR';

R$^9$ and R$^{10}$ are selected from the group consisting of hydrogen, halo, cyano, hydroxy, lower alkoxy and —NRR';

n is 0 or 1;

R and R' are independently selected from the group consisting of hydrogen, alkyl, cycloakyl, aryl, —C(=O)R" and, combined, a five-member or a six member heteroalicyclic; and, R" is selected from the group consisting of hydrogen, alkyl, cycloalkyl, aryl, heteroaryl (bonded through a ring carbon) and heteroalicyclic (bonded through a ring carbon).

28. The method of claim 27, wherein aid hydrogenation catalyst is palladium on carbon; and, said solvent is dimethylformamide.

29. A method for inhibiting growth of bacteria comprising contacting said bacteria, for a time and under conditions effective to inhibit bacterial growth, with a compound of Formula I or Formula III, wherein the compound of formula I has the chemical structure

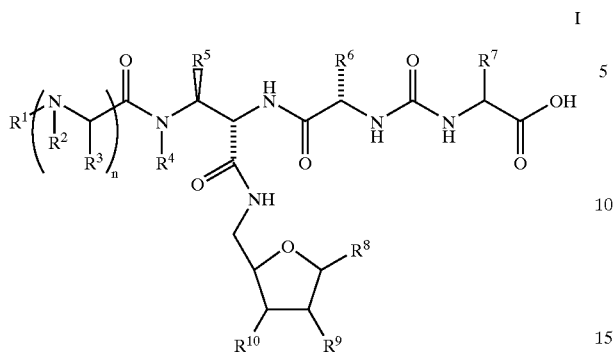

wherein:
R¹ and R² are independently selected from the group consisting of hydrogen, alkyl, cycloalkyl, aryl, heteroaryl, heteroalicyclic, —C(=O)R", —C(=O)OR", R"C(=O)O—, —C(=O)NRR', cyano, hydroxy, alkoxy, —NRR', amino acid, peptide of 2–4 amino acid residues, and, R¹ and R², taken together with the nitrogen atom to which they are bonded, form a heteroaryl or a heteroalicyclic, or R¹ or R², taken with R" is selected from the group consisting of hydrogen, alkyl, cycloalkyl, aryl, heteroaryl (bonded through a ring carbon) and heteroalicyclic (bonded through a ring carbon); and, the compound of formula III has the chemical structure:

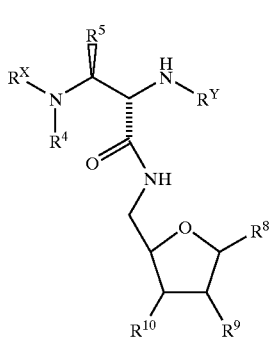

wherein:
R$^x$ is selected from the group consisting of a first amino acid and a first peptide of 2–4 amino acid residues, said first amino acid or said first peptide being optionally substituted with one or more groups independently selected from the group consisting of alkyl, cycloalkyl, alkenyl, alkynyl, aryl, heteroaryl and heteroalicyclic, R$^y$ is selected from the group consisting of a second amino acid and a second peptide of 2–4 amino acid residues, said second amino group or said second peptide being optionally substituted with one or more groups independently selected from the group consisting of alkyl, cycloalkyl, alkenyl, alkynyl, aryl, heteroaryl and heteroalicyclic:

said second amino acid or a terminal amino acid of said second peptide is linked through its α-amino nitrogen atom to an α-amino nitrogen atom of a third amino acid or a third peptide of 2–4 amino acid residues by a carbonyl group, said third amino acid or said third peptide being optionally substituted with one or more groups independently selected from the group consisting of alkyl, cycloalkyl, alkenyl, alkynyl, aryl, heteroaryl and heteroalicyclic;

R⁴ and R⁵ are independently selected from the group consisting of hydrogen, alkyl, cycloalkyl, alkenyl, alkynyl, aryl, heteroaryl and heteroalicyclic:

R⁸ is uracil or dihydrouracil optionally substituted with a group selected from alkyl, cycloalkyl, alkenyl, alkynyl, aryl, heteroaryl, heteroalicyclic, halo, cyano, nitro and —NRR';

R⁹ and R¹⁰ are independently selected from the group consisting of hydrogen, hydroxy, alkoxy, mercapto, alkylthio, halo, cyano, and —NRR'; and, R and R' are independently selected from the group consisting of hydrogen, alkyl, alkenyl, alkynyl, aryl, heteroaryl, heteroalicyclic, —C(=O)R", —C(=O)OR" and R"C(=O)O—, R" being selected from the group consisting of hydrogen, alkyl, cycloalkyl, aryl, heteroaryl (bonded through ring carbon) and heteroalicyclic (bonded through a ring carbon).

30. The method of claim 29, wherein said bacteria are selected from the group consisting of Pseudomonas, Escherichia, Streptococcus, Staphylococcus, Mycobacteria, Enterococcus and Haemophilus.

31. A method for inhibiting growth of bacteria comprising contacting said bacteria, for a time and under conditions effective to inhibit bacterial growth, with a compound selected from the group consisting of:

1-[5'-[(2S,3S)-N²-[N-[[(1S)-1-Carboxy-4-hydroxyphenethyl]carbamoyl]-L-phenylalanyl]-N³-L-phenylalanyl-N³-methyl-2,3-diaminobutyramido]-3',5'-dideoxy-α-L-arabinofuranosyl]uracil (Compound 100), 1-[5'-[(2S,3S)-N²-[N-[[(1S)-1-Carboxy-4-hydroxyphenethyl]carbamoyl]-L-phenylalanyl]-N³-L-leucyl-N³-methyl-2,3-diaminobutyramido]-3,5-dideoxy-α-L-arabinofuranosyl]uracil (Compound 101), 1-[5'-[(2S,3S)-N²-[N-[[(1S)-1-Carboxy-4-hydroxyphenethyl]carbamoyl]-L-phenylalanyl]-N³-glycyl-N³-methyl-2,3-diaminobutyramido]-3',5'-dideoxy-α-L-arabinofuranosyl]uracil (Compound 102), 1-[5'-[(2S,3S)-N²-[N-[[(1S)-1-Carboxy-2-indol-3-ylethyl]carbamoyl]-L-alanyl]-N³-L-3-hydroxyphenylalanyl-N³-methyl-2,3-diaminobutyramidol-3',5'-dideoxy-α-L-arabinofuranosyl]uracil (Compound 103), 1-[5'[(2S,3S)-N²-[N-[[(1S)-1-Carboxy4-hydroxyphenethyl]carbamoyl]-L-methionyl]-N³-glycyl-N³-methyl-2,3-diaminobutyramidol-3',5'-dideoxy-α-L-arabinofuranosyl]uracil (Compound 104), 1-[5'[(2S,3S)-N²-[N-[[(1S)-1-Carboxy-4-hydroxyphenethyl]carbamoyl]-L-4-fluorophenylalanyl]-N³-L-4-fluorophenylalanyl-N³-methyl-2,3-diaminobutyramido]-3',5'-dideoxy-α-L-arabinofuranosyl]uracil (Compound 105), 1-[5'[(2S,3S)-N²-[N-[[(1S)-1-Carboxy-4-hydroxyphenethyl]carbamoyl]-L-4-fluorophenylalanyl)-N³-L-phenylalanyl-N³-methyl-2,3-diaminobutyramido]-3',5'-dideoxy-α-L-arabinofuranosyl]uracil (Compound 106), 1-[5'[(2S,3S)-N²-[N-[[(1S)-1-Carboxy-4-hydroxyphenethyl]carbamoyl]-L-4-fluorophenylalanyl]-N³-L-leucyl-N⁻³-methyl-2,3-diaminobutyramido]-3',5'-dideoxy-α-L-arabinofuranosyl]uracil (Compound 107), 1-[5'[(2S,3S)-N²-[N-[[(1S)-1-Carboxy-2-indol-3-ylethyl]carbamoyl]-L-leucyl]-N³-L-leucyl-N³-methyl-2,3- diaminobutyramido]-3',5'-dideoxy-α-L-arabinofuranosyl]uracil (Compound 108),

1-[5'-[(2S,3S)-N²-[N-[[(1S)-1-Carboxy-2-indol-3-ylethyl]carbamoyl]-L-leucyl]-N³-glycyl-N³-methyl-2,3-diaminobutyramido]-3',5'-dideoxy-α-L-arabinofuranosyl]uracil (Compound, 109), 1-[5'-[(2S,3S)-N²-[N-[[(1S)-1-Carboxy-2-indol-3-ylethyl]carbamoyl]-L-methionyl]-N³-L-4-fluorophenylalanyl-N³-methyl-2,3-diaminobutyramido]-3',5'-dideoxy-α-L-arabinofuranosyl]uracil (Compound 110), 1-[5'-[(2S,3S)-N²-[N-[[(1S)-1-Carboxy-2-indol-3-ylethyl]carbamoyl]-L-methionyl]-N³-L-phenylalanyl-N³-methyl-2,3-diaminobutyramido]-3',5'-dideoxy-α-L-arabinofuranosyl]uracil (Compound 111), 1-[5'-[(2S,3S)-N²-[N-[[(1S)-1-Carboxy-2-indol-3-ylethyl]carbamoyl]-L-methionyl]-N³-glycyl-N³-methyl-2,3-diaminobutyramido]-3',5'-dideoxy-α-L-arabinofuranosyl]uracil (Compound 112), 1-[S-[(2S,3S)-[N-[[(1S)-1-Carboxy-2-indol-3-ylethyl]carbamoyl]-L-4-fluorophenylalanyl]-N³-L-phenylalanyl-N³-methyl-2,3-diaminobutyramido]-3,5-dideoxy-α-L-arabinofuranosyl]uracil (Compound 113), 1-[5-((2S,3S)-N²-[N-[[(1S)-1-Carboxy-2-indol-3-ylethyl]carbamoyl]-L-phenylalanyl]-N³-L-4-fluorophenylalanyl-N³-methyl-2,3-diaminobutyramido]-3,5-dideoxy-α-L-arabinofuranosyl]uracil (Compound 114), 1-[5'[(2S,3S)-N³-L-Alanyl-N²-[N-[[(1S)-1-carboxy-4-hydroxyphenethyl]carbamoyl]-L-methionyl]-N³-methyl-2,3-diaminobutyramido]-3',5'-dideoxy-α-L-arabinofuranosyl](Compound 115), 1-[5'-[(2S,3S)-N²-[N-[[(1S)-1-Carboxy-2-indol-3-ylethyl]carbamoyl]-L-4-fluorophenylalanyl]-N³-glycyl-N³-methyl-2,3-diaminobutyramido]-3',5'-dideoxy-α-L-arabinofuranosyl]uracil (Compound 116), 1-[5'-[(2S,3S)-N²-[N-[[(1S)-1-Carboxy-2-indol-3-ylethyl]carbamoyl]-L-4-fluorophenylalanyl]-N³-L-leucyl-N³-methyl-2,3-diaminobutyramido]-3',5'-dideoxy-α-L-arabinofuranosyl]uracil (Compound 117), 1-[5'-[(2S,3S)-N²-[N-[[(1S)-1-Carboxy-2-indol-3-ylethyl]carbamoyl]-L-4-fluorophenylalanyl]-N³-L-4-fluorophenylalanyl-N³-methyl-2,3-diaminobutyramido]-3',5'-dideoxy-α-L-arabinofuranosyl]uracil (Compound 118), 1-[5'-[(2S,3S)-N³-L-Alanyl-N²-[N-[[(1S)-1-Carboxy-4-hydroxyphenethyl]carbamoyl]-L-3-(2-thienyl)alanyl]-N³-methyl-2,3-diaminobutyramido]-3',5'-dideoxy-α-L-arabinofuranosyl]uracil (Compound 119), 1-[5'-[(2S,3S)-N²-[N-[[(1S)-1-Carboxy-4-hydroxyphenethyl]carbamoyl]-L-leucyl]-N³-glycyl-N³-methyl-2,3-diaminobutyramido]-3',5'-dideoxy-α-L-arabinofuranosyl]uracil (Compound 120), 1-[5'-[(2S,3S)-N²-[N-[[(1S)-1-Carboxy-2-indol-3-ylethyl]carbamoyl]-L-alanyl]-N³-glycyl-N³-methyl-2,3-diaminobutyramido]-3',5'-dideoxy-α-L-arabinofuranosyl]uracil (Compound 121), 1-[5'-[[(2S,3S)-L-Alanyl]-N²-[N-[[(1S)-1-carboxy-phenethyl]carbamoyl]-L-phenylalanyl]-N³-methyl-2,3-diaminobutyramido]-3',5'-dideoxy-α-L-arabinofuranosyl]uracil (Compound 122), 1-[5'-[(2S,3S)-N³-5-Aminopentanoyl-N²-[N-[[(1S)-1-carboxy-2-indol-3-ylethyl]carbamoyl]-L-phenylalanyl]-N³-methyl-2,3-diaminobutyramidol-3',5'-dideoxy-α-L-arabinofuranosyl]uracil (Compound 123), 1-[5'-[(2S,3S)-N³-5-Aminopentanoyl-N²-[N-[[(1S)-1-Carboxy-4-hydroxyphenethyl]carbamoyl-L-4-fluorophenylalanyl]-N³-methyl-2,3-diaminobutyramidol-3',5'-dideoxy-α-L-arabinofuranosyl]uracil (Compound 124), 1-[5'-[(2S,3S)-N³-L-Alanyl-N²-[N-[[(1S)-1-carboxy-2-(2-thienyl)ethyl]carbamoyl]-L-phenylalanyl]-N³-methyl-2,3-diaminobutyramido]-3',5'-dideoxy-α-L-arabinofuranosyl]uracil (Compound 125), 1-[5'-[(2S,3S)-N³-L-Alanyl-N²-[N-[[(1S)-1-carboxy-4-hydroxyphenethyl]carbamoyl]-L-4-nitrophenylalanyl]-N³-methyl-2,3-diaminobutyramido]-3',5'-dideoxy-α-L-arabinofuranosyl]uracil (Compound 126), 1-[5'-[(2S,3S)-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 127), 1-[5'-[(2S,3S)-N²-[N-[[(1S)-1-Carboxy-2-indol-3-ylethyl]carbamoyl]-L-phenylalanyl]-N³-glycyl-N³-methyl-2,3-diaminobutyramido]-3',5'-dideoxy-α-L-arabinofuranosyl]uracil (Compound 128), 1-[5'-[(2S,3S)-N²-[N-[[(1S)-1-carboxy-4-hydroxyphenethyl]carbamoyl]-L-4-fluorophenylalanyl]-N³-glycyl-N³-methyl-2,3-diaminobutyramido]-3',5'-dideoxy-α-L-arabinofuranosyl]uracil (Compound 129), 1-[5'-[(2S,3S)-N³-L-alanyl-N²-[N-[[(1S)-1-carboxy-4-hydroxyphenethyl]carbamoyl]-L-benzothiophenylalanyl]-N³-methyl-2,3-diaminobutyramido]-3',5'-dideoxy-α-L-arabinofuranosyl]uracil (Compound 130), 1-[5'-[(2S,3S)-N³-3-Aminobenzoyl-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 131), 1-[5'-[(2S,3S)-N³-L-Alanyl-N²-[N-[[(1S)-1-carboxy-4-hydroxyphenethyl]carbamoyl]-L-thiazolylalanyl]-N³-methyl-2,3-diaminobutyramidol-3',5'-dideoxy-α-L-arabinofuranosyl]uracil (Compound 132), 1-[5'-[(2S,3S)-N³-L-Alanyl-N²-[N-[[(1S)-1-carboxy-3-naphtenethyl]carbamoyl]-L-phenylalanyl]-N³-methyl-2,3-diaminobutyramido]-3',5'-dideoxy-α-L-arabinofuranosyl]uracil (Compound 133), 1-[5'-[(2S,3S)-N³-L-Alanyl-N²-[N-[[(1S)-1-carboxy-4-hydroxyphenethyl]carbamoyl]-L-4-iodophenylalanyl]-N³-methyl-2,3-diaminobutyramido]-3',5'-dideoxy-α-L-arabinofuranosyl]uracil (Compound 134), 1-[5'-[(2S,3S)-N³-L-Alanyl-N²-[N-[[(1S)-1-carboxy-4-hydroxyphenethyl]carbamoyl]-L-4-chlorophenylalanyl]-N³-methyl-2,3-diaminobutyramido]-3',5'-dideoxy-α-L-arabinofuranosyl]uracil (Compound 135), 1-[5'-[(2S,3S)-N³-L-Alanyl-N²-[N-[[(1S)-1-carboxy-2-indol-3-carbamoyl]-L-cyclohexylalanyl]-N³-methyl-2,3-diaminobutyramido]-3',5'-dideoxy-α-L-arabinofuranosyl]uracil (Compound 136), 1-[5'-[(2S,3S)-N³-L-Alanyl-N²-[N-[[(1S)-1-carboxy4-hydroxyphenethyl]carbamoyl]-L-homophenylalanyl]-N³-methyl-2,3-diaminobutyramido]-3',5'-dideoxy-α-L-arabinofuranosyl]uracil (Compound 137), 1-[5'-[(2S,3S)-N³-L-Alanyl-N²-[N-[[(1S)-1-carboxy-2-indol-3-ylethyl]carbamoyl]-L-homophenylalanyl]-N³-methyl-2,3-diaminobutyramido]-3',5'-dideoxy-α-L-arabinofuranosyl]uracil (Compound 138), 1-[S-[(2S,3S)-N³-L-Alanyl-N²-[N-[[(1S)-1-carboxy-2-indol-3-ylethyl]carbamoyl]-L-2-fluorophenylalanyl]-N³-methyl-2,3-diaminobutyramido]-3,5-dideoxy-α-L-arabinouranosyl]uracil (Compound 139), 1-[5-[(2S,3S)-N³-L-Alanyl-N²-[N-[[(1S)-1-carboxy-4-hydroxyphenethyl]carbamoyl]-L-2-fluorophenylalanyl]-N³-methyl-2,3-diaminobutyramido]-3,5-dideoxy-α-L-arabinofuranosyl]uracil (Compound 140), 1-[5'-[(2S,3S)-N³-L-Alanyl-N²-[N-[[α(R,S)-1-carboxy-phenylmethyl]carbamoyl]-L-4-fluorophenylalanyl]-N³- methyl-2,3-diaminobutyramido]-3',5'-dideoxy-α-L-arabinofuranosyl]uracil (Compound 141), 1-[5'-[(2S,3S)-N³-L-Alanyl-N²-[N-[[α(S,R)-1-carboxy-phenylmethyl]carbamoyl]-L-4-fluorophenylalanyl]-N³-methyl-2,3-diaminobutyramido]-3',5'-dideoxy-α-L-arabinofuranosyl]uracil (Compound 142), 1-[5'-[(2S,3S)-N³-L-Alanyl-N²-[N-[[(1S)-1-carboxy-2-indol-3-ylethyl]carbamoyl]-L-(3,4)-difluorophenylalanyl]-N³-methyl-2,3-diaminobutyramido]-3',5-dideoxy-α-L-arabinofuranosyl]uracil (Compound 143), 1-[5'-[(2S,3S)-N³-L-Alanyl-N²-[N-[[(1S)-1-carboxy-4hydroxyphenethyl]carbamoyl]-L-(3,4)-difluorophenylalanyl]-N³-methyl-2,3-diaminobutyramido]-3',5'-dideoxy-α-L-arabinofuranosyl]uracil (Compound 144), 1-[5'-[(2S,3S)-N³-L-Alanyl-N²-[N-[[(1S)-1-carboxy4-hydroxyphenethyl]carbamoyl]-L-4-(trifluoromethyl)-phenylalanyl]-N³-methyl-2,3-diaminobutyramido]-3',5'-dideoxy-α-L-arabinofuranosyl]uracil (Compound 145), 1-[5'-[(2S,3S)-N³-L-Alanyl-N²-[N-[[(1S)-1-carboxy-2-indol-3-ylethyl]carbamoyl]-L-4-(trifluoromethyl)phenylalanyl]-N³-methyl-2,3-diaminobutyramido]-3',5'-dideoxy-α-L-arabinofuranosyl]uracil (Compound 146), 1-[5'-[(2S,3S)-N²-[N-[[(1S)-1-Carboxy-2-indol-3-ylethyl]carbamoyl]-L-phenylalanyl]-N³-L-lysinyl-N³-methyl-2,3-diaminobutyramido]-3',5'-dideoxy-α-L-arabinofuranosyl]uracil (Compound 147), 1-[5'-[(2S,3S)-N³-L-Alanyl-N²-[N-[[(1S)-1-carboxy-2-indol-3-ylethyl]carbamoyl]-L-lysinyl]-N³-methyl-2,3-diaminobutyramido]-3',5'-dideoxy-α-L-arabinofuranosyl]uracil (Compound 148), 1-[5'-[(2S,3S)-N³-L-Alanyl-N²-[N-[[(1S)-1-carboxy-5-imidazylethyl]carbamoyl]-L-phenylalanyl]-N³-methyl-2,3-diaminobutyramido]-3',5'-dideoxy-α-L-arabinofuranosyl]uracil (Compound 149), 1-[5'-[(2S,3S)-N³-(L-O-Benzylserinyl)-N²-[N-[[(1S)-1-carboxy-4-hydroxyphenethyl]carbamoyl]-L-phenylalanyl]-N³-methyl-2,3-diaminobutyramido]-3',5'-dideoxy-α-L-arabinofuranosyl]uracil (Compound 150), 1-[5'-[(2S,3S)-N²-[N-[[(1S)-1-Carboxy-2-indol-3-ylethyl]carbamoyl]-L-phenylalanyl]-N³-methyl-2,3-diaminobutyramido]-3',5'-dideoxy-α-L-arabinofuranosyl]uracil (Compound 151), 1-[5'-[(2S,3S)-N³-L-Alanyl-N²-[N-[[(1S)-1-carboxy-4-hydroxyphenethyl]carbamoyl]-L-3-(2-naphthyl)alanyl]-N³-methyl-2,3-diaminobutyramido]-3'5'-dideoxy-α-L-arabinofuranosyl]uracil (Compound 152), 1-[5'-[(2S,3S)-N³-L-Alanyl-N²-[N-[[(1S)-1-carboxy-2-indol-3-ylethyl]carbamoyl]-L-3-(2-naphthyl)alanyl]-N³-methyl-2,3-diaminobutyramido]-3',5'-dideoxy-α-L-arabinofuranosyl]uracil (Compound 153), 1-[5'-[(2S,3S)-N³-L-Alanyl-N²-[N-[[(1S)-1-carboxy-2-indol-3-ylethyl]carbamoyl]-L-phenylalanyl]-N³-methyl-2,3-diaminobutyramido]-3',5'-dideoxy-α-L-arabinofuranosyl]uracil (Compound 154), 1-[5'-[(2S,3S)-N³-L-Alanyl-N²-[N-[[(1S)-1-carboxy-2-indol-3-ylethyl]carbamoyl]-L-4-biphenylalanyl]-N³-methyl-2,3-diaminobutyramido]-3',5'-dideoxy-α-L-arabinofuranosyl]uracil (Compound 155), 1-[5'-[(2S,3S)-N²-[N-[[(1S)-1-Carboxy-2-indol-3-ylethyl]carbamoyl]-L-phenylalanyl]-N³-L-phenylalanyl-N³-methyl-2,3-diaminobutyramido]-3',5'-dideoxy-α-L-arabinofuranosyl]uracil (Compound 156), 1-[5'-[(2S,3S)-N³-L-Alanyl-N²-[N-[[(1S)-1-carboxy-4-hydroxyphenethyl]carbamoyl]-L-4-fluorophenylalanyl]-N³-methyl-2,3-diaminobutyramido]-3',5'-dideoxy-α-L-arabinofuranosyl]uracil (Compound 157), 1-[5'-[(2S,3S)-N³-L-Alanyl-N²-[N-[[(1S)-1-carboxy-2-indol-3-ylethyl]carbamoyl]-L-4-fluorophenylalanyl]-N³-methyl-2,3-diaminobutyramidol-3',5'-dideoxy-α-L-arabinofuranosyl]uracil (Compound 158), 1-[5'-[(2S,3S)-N²-[N-[[(1S)-1-Carboxy-2-indol-3-ylethyl]carbamoyl]-L-phenylalanyl]l-N³-L-leucyl-N³-methyl-2,3-diaminobutyramido]-3',5'-dideoxy-α-L-arabinofuranosyl]uracil (Compound 159), 1-[5'-[(2S,3S)-N³-L-Alanyl-N²-[N-[[(1S)-1-carboxy-4-hydroxyphenethyl]carbamoyl]-L-phenylalanyl]-N³-methyl-2,3-diaminobutyramido]-3',5'-dideoxy-α-L-arabinofuranosyl]uracil (Compound 160), 1-[5'-[(2S,3S)-N³-L-Alanyl-N²-[N-[[(1S)-1-carboxy-4-hydroxyphenethyl]carbamoyl]-L-leucyl]-N³-methyl-2,3-diaminobutyramido]-3',5'-dideoxy-α-L-arabinofuranosyl]uracil (Compound 161), 1-[5'-[(2S,3S)-N²-[N-[[(1S)-1-Carboxy-2-indol-3-ylethyl]carbamoyl]-L-methionyl]-N³-L-methionyl-N³-methyl-2,3-diaminobutyramido]-3',5'-dideoxy-α-L-arabinofuranosyl]uracil (Compound 162), 1-[5'-[(2S,3S)-N²-[N-[[(1S)-1-Carboxy-2-indol-3-ylethyl]carbamoyl]-L-phenylalanyl]-N³-L-tyrosyl-N³-methyl-2,3-diaminobutyramido]-3',5'-dideoxy-α-L-arabinofuranosyl]uracil (Compound 163), 1-[5'-[(2S,3S)-N³-L-Alanyl-N²-[N-[[(1S)-1-carboxy-2-indol-3-ylethyl]carbamoyl]-L-phenylalanyl]-N³-methyl-2,3-diaminobutyramido]-3',5'-dideoxy-α-L-arabinofuranosyl]uracil (Compound 164), 1-5'-[(2S,3S)-N²-[N-[[(1S)-1-Carboxy-2-indol-3-ylethyl]carbamoyl]-L-alanyl]-N³-methyl-2,3-diaminobutyramido]-3',5'-dideoxy-α-L-arabinofuranosyl]uracil (Compound 165), 1-[5'-[(2S,3S)-N³-L-Alanyl-N²-[N-([(1S)-1-carboxy-2-indol-3-ylethyl]carbamoyl]-L-leucinyl]-N³-methyl-2,3-diaminobutyramido]-3',5'-dideoxy-α-L-arabinofuranosyl]uracil (Compound 166), 1-[5'-[(2S,3S)-N³-L-Alanyl-N²-[N-[[(1S)-1-carboxy-phenethyl]carbamoyl]-L-methionyl]-N³-methyl-2,3-diaminobutyramido]-3',5'-dideoxy-α-L-arabinofuranosyl]uracil (Compound 167), 1-5'-[(2S,3S)-N²-[N-[[(1S)-1-Carboxy-2-indol-3-ylethyl]carbamoyl]-L-alanyl]-N³-L-methionyl-N³-methyl-2,3-diaminobutyramido]-3',5'-dideoxy-α-L-arabinofuranosyl]uracil (Compound 168), 1-[5'-[(2S,3S)-N³-L-Alanyl-N²-[N-[[(1S)-1-carboxy-2-indol-3-ylethyl]carbamoyl]-L-valinyl]-N³-methyl-2,3-diaminobutyramido]-3',5'-dideoxy-α-L-arabinofuranosyl]uracil (Compound 169), 1-[5'-[(2S,3S)-N³-L-Alanyl-N²-[N-[[(1S)-1-carboxy-2-indol-3-ylethyl]carbamoyl]-L-leucinyl]-N³-methyl-2,3-diaminobutyramido]-3',5'-dideoxy-α-L-arabinofuranosyl]uracil (Compound 170), 1-[5'-[(2S,3S)-N³-D-Alanyl-N²-[N-[[(1S)-1-carboxy-2-indol-3-ylethyl]carbamoyl]-L-alanyl]-N³-methyl-2,3-diaminobutyramido]-3',5'-dideoxy-α-L-arabinofuranosyl]uracil (Compound 171), and 1-[5'-[(2S,3S)-N³-L-Alanyl-N²-[N-[[(1S)-1-Carboxy-2-indol-3-ylethyl]carbamoyl]-L-alanyl]-N³-methyl-2,3-diaminobutyramido]-3',5'-dideoxy- -D-ribofuranosyl]uracil (Compound 172).

\* \* \* \* \*